(12) United States Patent
Dar et al.

(10) Patent No.: US 11,027,117 B2
(45) Date of Patent: Jun. 8, 2021

(54) RESILIENT HEAD MOUNTED DEVICE FOR NEUROSTIMULATION AND SENSING OF BODY PARAMETERS

(71) Applicant: NEUROLIEF LTD., Yokneam Illit (IL)

(72) Inventors: Amit Dar, Kfar-Hess (IL); Amir Cohen, Ra'anana (IL); Ron Belson, Tel Aviv (IL); Jonathan Bar-Or, Pardes Hana Karkur (IL)

(73) Assignee: NEUROLIEF LTD., Yokneam Illit (IL)

( * ) Notice: Subject to any disclaimer, the term of this patent is extended or adjusted under 35 U.S.C. 154(b) by 81 days.

(21) Appl. No.: 16/070,563

(22) PCT Filed: Jan. 26, 2017

(86) PCT No.: PCT/IB2017/050416
§ 371 (c)(1),
(2) Date: Jul. 17, 2018

(87) PCT Pub. No.: WO2017/130133
PCT Pub. Date: Aug. 3, 2017

(65) Prior Publication Data
US 2019/0022372 A1    Jan. 24, 2019

(30) Foreign Application Priority Data
Jan. 27, 2016   (GB) ..................... 1601536

(51) Int. Cl.
*A61B 5/00* (2006.01)
*A61N 1/04* (2006.01)
(Continued)

(52) U.S. Cl.
CPC ............ *A61N 1/0456* (2013.01); *A61B 5/291* (2021.01); *A61B 5/6803* (2013.01);
(Continued)

(58) Field of Classification Search
None
See application file for complete search history.

(56) References Cited

U.S. PATENT DOCUMENTS 4,638,807 A * 1/1987 Ryder ................ A61B 5/04085
600/383
4,979,508 A   12/1990 Beck
(Continued)

FOREIGN PATENT DOCUMENTS

| KR | 101525450 B1 | 6/2015 |
| WO | 2007138598 A2 | 12/2007 |

(Continued)

OTHER PUBLICATIONS

International Search Report for PCT/IB2017/050416 dated Dec. 20, 2015.
(Continued)

*Primary Examiner* — Erica S Lee
(74) *Attorney, Agent, or Firm* — Marc Van Dyke; Momentum IP

(57) ABSTRACT

A headset for use in delivering electrical stimulation to the skin surface of the head or in sensing one or more body parameters of the head of a user.

24 Claims, 21 Drawing Sheets

(51) Int. Cl.
*A61N 1/36* (2006.01)
*A61B 5/291* (2021.01)
*A61B 5/0205* (2006.01)

(52) U.S. Cl.
CPC ......... *A61N 1/0476* (2013.01); *A61N 1/0484* (2013.01); *A61N 1/36025* (2013.01); *A61B 5/02055* (2013.01); *A61B 5/4836* (2013.01); *A61B 5/6814* (2013.01); *A61B 5/6831* (2013.01); *A61N 1/36034* (2017.08)

(56) References Cited

U.S. PATENT DOCUMENTS

| | | | |
|---|---|---|---|
| 6,077,237 A | 6/2000 | Campbell et al. | |
| 2004/0073129 A1* | 4/2004 | Caldwell | A61B 5/0478 600/544 |
| 2011/0319975 A1 | 12/2011 | Ho et al. | |
| 2013/0104288 A1* | 5/2013 | Schlottau | A61B 5/01 2/209.13 |
| 2013/0158626 A1 | 6/2013 | DeGiorgio et al. | |
| 2013/0282095 A1* | 10/2013 | Mignolet | A61N 1/0484 607/139 |
| 2013/0296967 A1 | 11/2013 | Skaribas et al. | |
| 2013/0326790 A1* | 12/2013 | Cauwels | A61B 5/02233 2/170 |
| 2014/0081369 A1 | 3/2014 | Sosa et al. | |
| 2014/0277324 A1 | 9/2014 | DiUbaldi et al. | |
| 2014/0316230 A1 | 10/2014 | Denison et al. | |
| 2015/0088224 A1 | 3/2015 | Goldwasser et al. | |
| 2015/0374971 A1 | 12/2015 | Dar et al. | |
| 2017/0224978 A1* | 8/2017 | Lee | A61N 1/0456 |
| 2017/0296121 A1* | 10/2017 | Dar | A61B 5/6803 |
| 2019/0117976 A1 | 4/2019 | Belson et al. | |

FOREIGN PATENT DOCUMENTS

| | | |
|---|---|---|
| WO | 2014141213 A1 | 9/2014 |
| WO | 2016017954 A1 | 2/2016 |
| WO | 2016155773 A1 | 10/2016 |

OTHER PUBLICATIONS

Written Opinion for PCT/IB2017/050416 dated Dec. 20, 2015.
Machine Translation (by Google Patents) for KR10152545 published on Jun. 3, 2015.
Machine Translation (by Google Patents) for WO2016017954 published on Feb. 4, 2016.

* cited by examiner

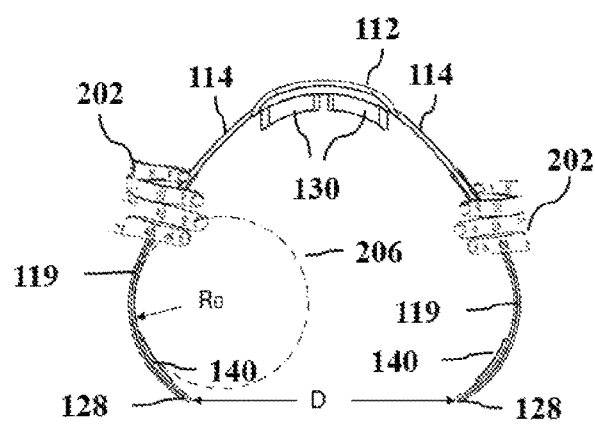
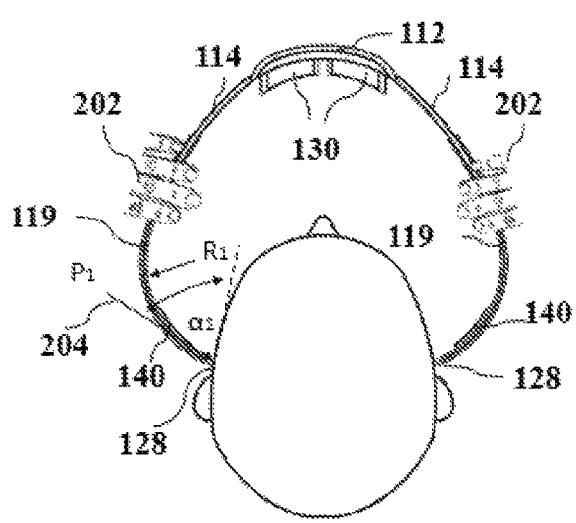
Fig. 3A  Fig. 3B
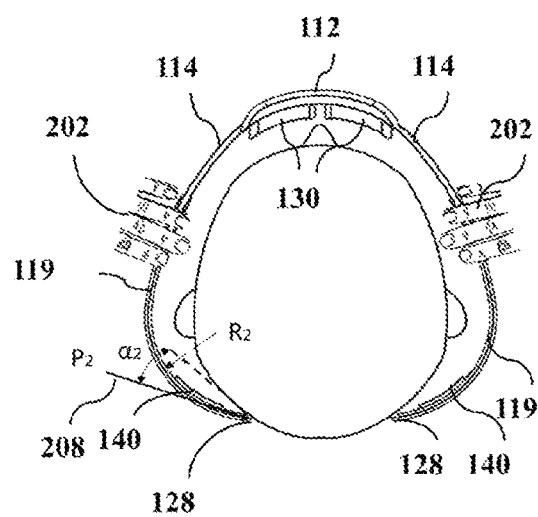
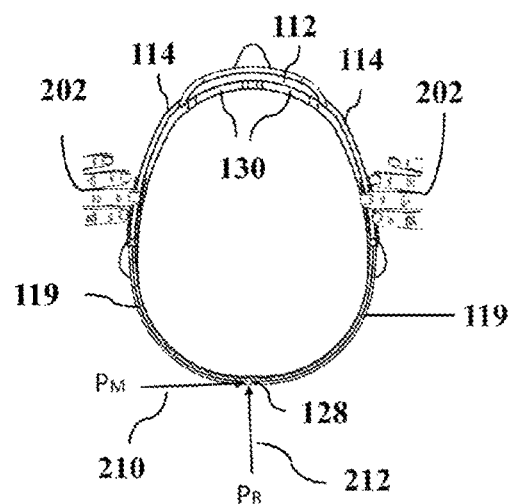
Fig. 3C  Fig. 3D

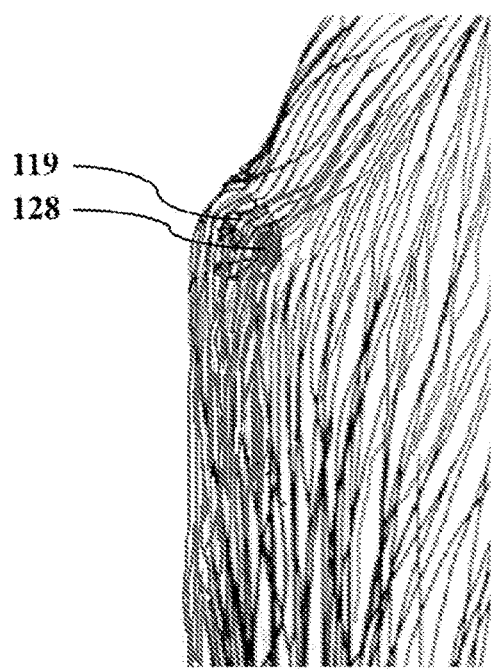
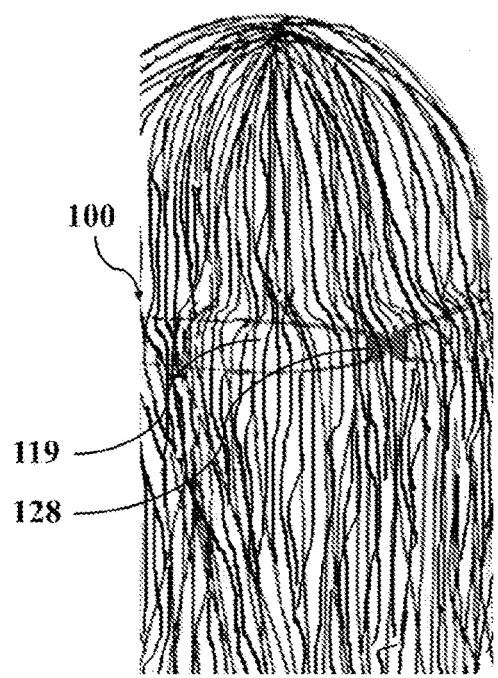
Fig. 4A                      Fig. 4B
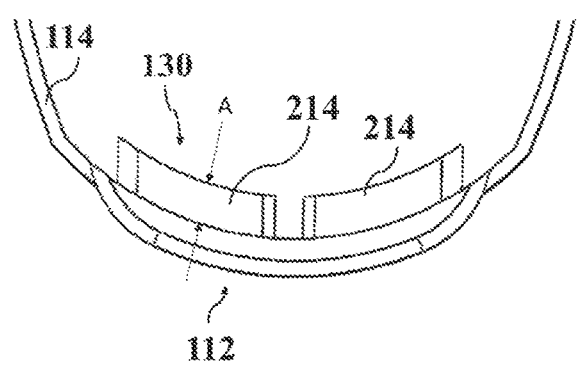
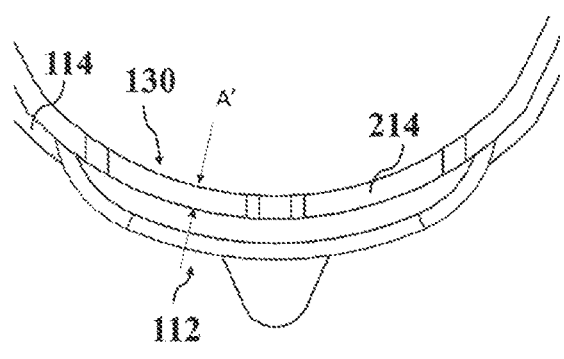
Fig. 5A                      Fig. 5B

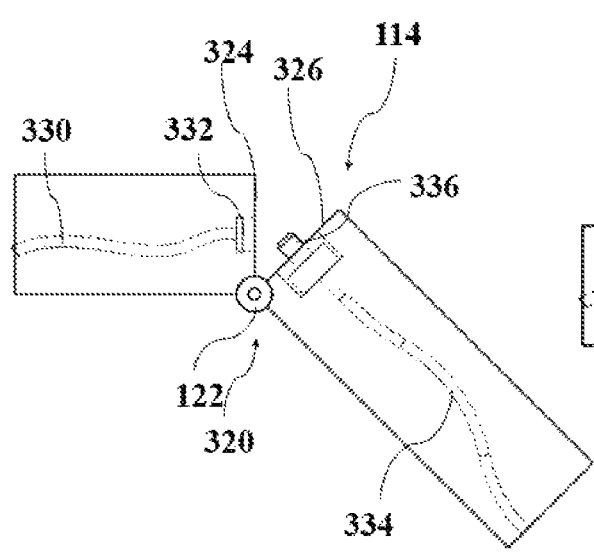 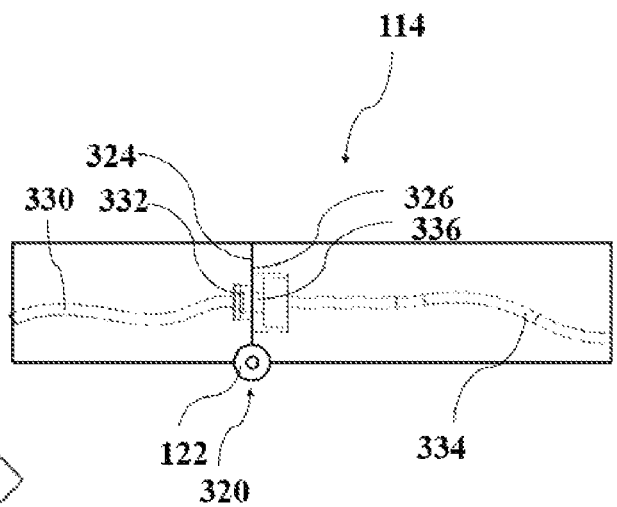
Fig. 18A    Fig. 18B
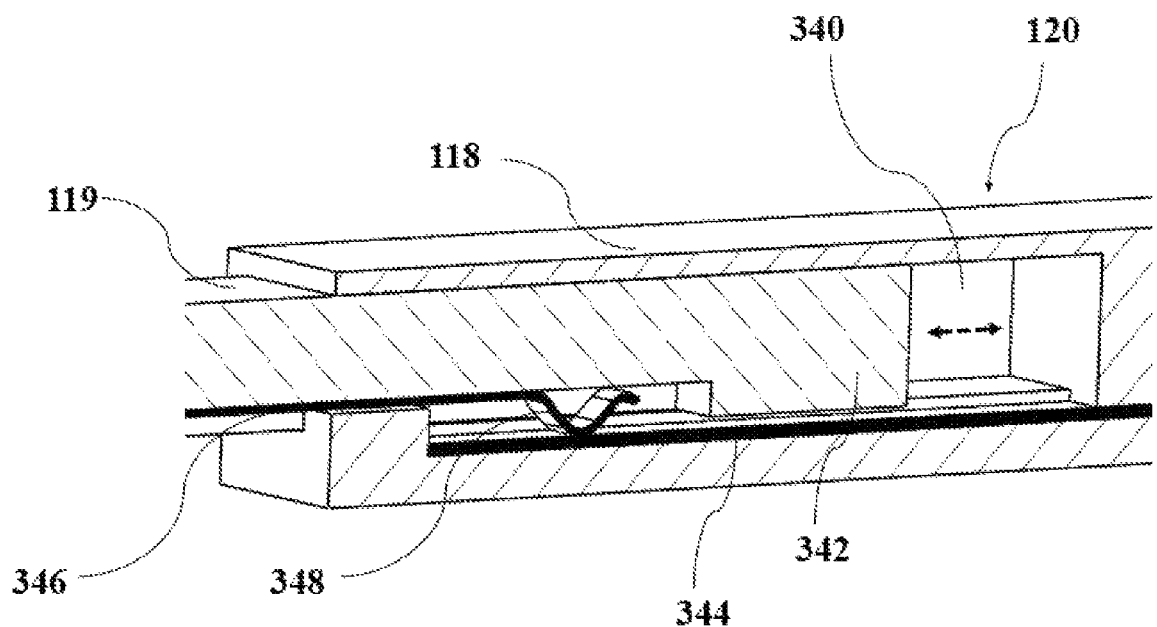
Fig. 19

RESILIENT HEAD MOUNTED DEVICE FOR NEUROSTIMULATION AND SENSING OF BODY PARAMETERS The present application is a national phase filing of PCT Patent Application No. PCT/IB2017/050416 filed Jan. 26, 2017 and entitled RESILIENT HEAD MOUNTED DEVICE FOR NEUROSTIMULATION AND SENSING OF BODY PARAMETERS, which gains priority from GB Patent Application Number 1601536.4 filed Jan. 27, 2016 and entitled RESILIENT HEAD MOUNTED DEVICE FOR NEUROSTIMULATION AND SENSING OF BODY PARAMETERS, both of which are incorporated herein by reference as if fully set forth herein.

FIELD OF THE INVENTION

The present invention relates to apparatus and methods for applying electrical stimulation to the head region, to headsets having electrodes for treatment of medical conditions using non-invasive electrical stimulation, to headsets adapted to assess medical conditions, and to electrode arrangements for use with such headsets.

BACKGROUND OF THE INVENTION

The present invention relates to apparatus and methods for applying electrical stimulation to the head region. The disclosed apparatus may be used for stimulation of peripheral and cranial nerves, for transcranial stimulation of brain regions, and for sensing various body parameters.

Peripheral and cranial nerves in the head region may be stimulated to treat various conditions such as chronic pain, migraine, tension headaches, cluster headaches, fibromyalgia, depression, post-traumatic stress syndrome, anxiety, stress, bipolar disorder, schizophrenia, obsessive compulsive disorder (OCD), insomnia, epilepsy, attention deficit disorder (ADD), attention deficit hyperactivity disorder (ADHD), Parkinson's disease, Alzheimer's disease, multiple sclerosis, and brain injuries such as stroke and traumatic brain injury (TBI). The anatomy of peripheral and cranial nerves in the head region, such as that of the occipital and trigeminal nerves, and their projections to brainstem regions such as the locus coeruleus and nucleus raphe magnus as well as to higher brain regions such as the thalamus and the cortex, may be advantageous when stimulating these nerves for treatment of such conditions.

Neurostimulation of superficial peripheral and cranial nerves in the head region, such as the occipital and trigeminal nerve branches, can be applied either invasively or non-invasively. Invasive procedures of peripheral nerve stimulation include occipital nerve stimulation which has shown to provide relief for chronic migraine in numerous clinical trials. Another more recent procedure for treatment of migraine combines stimulation of both occipital nerve branches (greater and lesser) and trigeminal nerve branches (mostly supraorbital and supratrochlear and occasionally also/or zygomaticotemporal and auriculotemporal). Recent clinical results support the expectation that applying peripheral nerve stimulation to a combination of the occipital and trigeminal nerve branches may result in a better outcome compared to stimulation of the occipital nerve or the trigeminal nerve alone. Indeed, the response rate for patients with head-wide pain who were treated with implanted peripheral nerve stimulation to the occipital and trigeminal nerves is reported to be better than 70%. This is an improvement from using stimulation to the occipital or trigeminal nerves only which is reported to bring about just a 40% response rate. However, implanted peripheral nerve stimulation remains an invasive and costly procedure with a high rate of complications including infection, bleeding or fluid collection under the skin, as well as hardware-related malfunctions such as migration and breakage of the implanted leads and pulse generator failure.

Non-invasive stimulation of trigeminal nerve branches, such as the supraorbital and supratrochlear, was found to be safe as a preventive therapy for migraine and as treatment for other conditions such as seizures and depression. Due to the challenge of transferring current through the hair, stimulation of the occipital nerve (greater, lesser and third occipital branches) is mostly performed with implanted nerve stimulators. In spite of that, the occipital nerve branches may also be stimulated transcutaneously. When passing at approximately the anatomical height of the superior nuchal line of the occipital bone, the occipital nerve lies superficially under the skin and if electrodes are placed under the hair and close enough to the scalp, effective nerve excitation can be reached, achieving similar clinical benefits to those of implanted stimulation, without the risks associated with an invasive procedure.

Transcranial direct current stimulation (tDCS) is another modality that has been studied for treatment of various medical and/or physiological conditions such as chronic pain, migraine, depression, post-traumatic stress disorder, bipolar disorder, schizophrenia, epilepsy, attention deficit disorder (ADD), attention deficit hyperactivity disorder (ADHD), Parkinson's disease, and Alzheimer's disease, as well as for assistance in recovery from stroke and traumatic brain injury and in cognitive learning. tDCS typically refers to the application of constant, low current stimulation in the range of 1-2 mA, delivered directly to an area of the brain, thereby to modulate the activity of targeted neurons. Typically, the electrode associated with the positive pole, or anode, causes an increase in activity of the target nerve, while the electrode associated with the negative pole, or cathode, causes a decrease in nerve activity.

SUMMARY OF THE INVENTION

According to some teachings of the present invention there is provided a headset including:

an elongate body member sufficiently long to encircle the head of a user, the elongate body member having a closed state and including an anterior section and a pair of arm sections, each arm section extending away from the anterior section and terminating in a posterior end;

a closure mechanism associated with the posterior ends of the arm sections, the closure mechanism having an open position and a closed position, wherein, when the closure mechanism is in the closed position, the body member is in the closed state whereby the headset is fully circumferential; and at least one electrode or at least one sensor, mounted on an inner surface of the body member, the at least one electrode or at least one sensor adapted to electrically communicate with a processing unit, wherein the headset is configured, when the headset is donned on the head of the user, to urge the at least one electrode or the at least one sensor to be positioned against the skin of the head of the user, and wherein the arm sections are resilient and have a predefined preload such that when the arm sections are outwardly displaced the preload drives the arm sections toward each other.

According to some teachings of the present invention there is also provided a headset including:

an elongate body member sufficiently long to encircle the head of a user, the elongate body member having a closed state and including an anterior section and a pair of arm sections, each arm section extending away from the anterior section and terminating in a posterior end;

a closure mechanism associated with the posterior ends of the arm sections, the closure mechanism having an open position and a closed position, wherein, when the closure mechanism is in the closed position, the body member is in the closed state whereby the headset is fully circumferential; and at least one electrode or at least one sensor, mounted on an inner surface of the body member, the at least one electrode or at least one sensor adapted to electrically communicate with a processing unit, wherein the headset is configured, when the headset is donned on the head of the user, to urge the at least one electrode or the at least one sensor to be positioned against the skin of the head of the user, wherein the arm sections are resilient and have a predefined preload such that when the arm sections are outwardly displaced the preload drives the arm members toward each other, and wherein, throughout donning of the headset by the user, the posterior ends are configured to apply a force to the head such that the posterior ends continuously engage the head.

In some embodiments, the user is a human user. In some such embodiments, the length of the elongate body member is smaller than 700 mm, 680 mm, or 660 mm.

In some embodiments, the body member has a rest state, and wherein, in the rest state, at least part of one of the arm sections overlaps at least part of the other of the arm sections.

In some embodiments, the force has a magnitude not greater than 20 N, 15 N, or 10 N. In some embodiments, the preload drives the arm sections toward the closed state. In some embodiments, the preload drive the arm sections toward the rest state.

In some embodiments, the predefined preload is adapted to ensure that the posterior ends of the arm sections engage the scalp of the user and plow between the hair during donning of the headset, such that when the headset is donned the at least one electrode or the at least one sensor is at least in direct physical contact with the scalp of the user.

In some embodiments, when the headset is donned, the at least one electrode or the at least one sensor is also in direct electrical contact with the scalp of the user.

In some embodiments, the arm sections are configured such that during donning of the headset, the posterior ends engage the sides of the head of the user forming an angle between the ends of the arm sections and the sides of the head of the user, which angle contributes to contact between the posterior ends and the scalp throughout donning of the headset. In some embodiments, the angle is in the range of 90 degrees to 20 degrees.

In some embodiments, the anterior section includes an anterior member, and the arm sections include arm members, distinct from the anterior member and connected thereto.

In some embodiments, the headset further includes at least one size-adjustment mechanism configured to enable adjustment of the circumference of the body member to comfortably fit circumferentially about heads having different circumferences. In some embodiments, the at least one size-adjustment mechanism includes a rigid size-adjustment mechanism. In some embodiments, the at least one size-adjustment mechanism includes two size-adjustment mechanisms, each associated with one of the arm sections. In some embodiments, the size-adjustment mechanism includes a ratcheting mechanism or a sliding mechanism.

In some embodiments, the body member includes at least one flexible temple arm portion, a pair of flexible posterior portions adjacent the posterior end of each of the arm sections, and the at least one size-adjustment mechanism.

In some embodiments, the body member includes a single flexible temple arm portion extending along the anterior section of the headset, and a pair of the flexible posterior portions.

In some embodiments, each of the arm sections includes a flexible temple arm portion adjacent the anterior section, and a flexible posterior portion adjacent the end of the arm section.

In some embodiments, a degree of flexibility of the at least one temple arm portion determines the resiliency of the arm sections.

In some embodiments, the posterior portion of each of the arm sections is curved, and curvature of the posterior portions are configured to contribute to continuous contact between the ends of the arm sections and the scalp throughout donning of the headset. In some embodiments, the posterior portions have a first curvature in the rest state and a second curvature during donning of the headset. In some embodiments, a first radius corresponding to the first curvature is smaller than a second radius corresponding to the second curvature. In some embodiments, the first radius is not greater than 150 mm. In some embodiments, in the closed state, curvature of the posterior portions conforms to curvature of the head of the user.

In some embodiments, during donning of the headset, the predefined preload acts mostly on the posterior ends of the arm sections.

In some embodiments, the size-adjustment mechanism is configured to be adjusted when the user first dons the headset, and subsequently to retain the size defined by the user, without requiring additional adjustment.

In some embodiments, the closure mechanism includes a magnetic closure mechanism including a magnetically attractable element at each of the posterior ends of the arm sections, the magnetically attractable elements being adapted to attract and engage one another, thereby to close the headset. In some embodiments, one of the magnetically attractable elements is a magnet and the other is formed of a magnetically attractable metal. In other embodiments, both the magnetically attractable elements are magnets.

In some embodiments, each of the magnetically attractable elements has at least a portion which defines a spherical surface and is disposed in a housing, wherein the spherical surfaces of the magnetically attractable elements are adapted to engage one another at a single point, thereby to close the headset. In some embodiments, the magnetically attractable elements are rotatably disposed in the housing and are adapted to automatically orient in an optimally polar orientation given a specific alignment of the posterior ends of the headset.

In some embodiments, the magnetically attractable elements are adapted to attract one another so as to close the headset when the magnetically attractable elements are at a distance not greater than 10 mm, not greater than 20 mm, or not greater than 30 mm.

In some embodiments, the at least one electrode has a resilient, flexible, sealing rim disposed therearound, such that when the at least one electrode engages a skin surface of the user, the sealing rim seals around the at least one electrode.

In some embodiments, the at least one electrode includes at least one anterior electrode mounted on an inner surface of the anterior section. In some embodiments, at least one of the at least one anterior electrode configured, when the headset is donned, to be disposed above at least one of the supratrochlear nerves and the supraorbital nerves of the user. In some embodiments, at least one of the at least one anterior electrode including a transcranial stimulation electrode configured, when the headset is donned, to be disposed above an anterior brain region of the user.

In some embodiments, the at least one anterior electrode includes a first anterior electrode and a second anterior electrode, each of the first and second anterior electrodes having a first end, a second end, a height, and a length, the heights of the first and the second anterior electrodes, at a maximal point thereof, being in the range of 10 mm to 40 mm, the first and second anterior electrodes arranged horizontally alongside one another on the elongate body member such that the second end of the first anterior electrode is adjacent the first end of the second anterior electrode with a distance therebetween, the distance being in the range of 1 mm to 15 mm, and a length consisting of the length of the first electrode, the length of the second electrode, and the distance, is in the range of 20 mm to 55 mm.

In some embodiments, the first anterior electrode is configured, when the headset is donned, to be disposed above the supratrochlear nerve on one side of the user's head, and the second anterior electrode is configured, when the headset is donned, to be disposed above the supraorbital nerve on the one side of the user's head, In some embodiments, each of the first and second anterior electrodes includes a liquid-absorbent layer having a biocompatible contact surface, the contact surface adapted to be juxtaposed against the skin surface and an electrode backing, attached to the liquid-absorbent layer, the backing containing at least one electrically conductive material or element, the conductive material or element being electrically connected with the liquid-absorbent layer, when the liquid-absorbent layer is filled with liquid.

In some embodiments, the first and second anterior electrodes are disposed on a joint substrate, the shared substrate including a first contact portion in electrical contact with the electrode backing of the first anterior electrode and a second contact portion in electrical contact with the electrode backing of the second anterior electrode.

In some embodiments, the ratio between an area of the first anterior electrode and an area of the second anterior electrode is in the range of 0.5-2. In some such embodiments, the area of the first electrode is equal to the area of the second electrode. In some embodiments, the first and second anterior electrodes have an identical contour.

In some embodiments, the first and second anterior electrodes extending, at a lower end thereof, along a single concave contour defined between first and second boundary points disposed at opposite ends of the concavity and adapted to generally follow the outline of the user's eyebrows,
wherein:

$A/L \geq 0.5$ mm

A being an area bounded by a line between the boundary points of the concavity, and the concavity;
L being a length of the line between the boundary points;
the length (L) being at least 10 mm;

wherein a line disposed between a first point on the concave contour and a second point on the perimeter, on a side opposite the concave contour, and aligned in perpendicular fashion with respect to the contour at the first point, has a length H,
wherein, over an entirety of the concave contour, $H_{max}/H_{min} \leq 2.5$, $H_{max}$ being a maximum value of H over the entirety; and
$H_{min}$ being a minimum value of H over the entirety.

In some embodiments, an angle between the line and the second end of the first anterior electrode adjacent the distance is in the range of 45-110 degrees.

In some embodiments, the headset further includes at least one compressible portion mounted onto an inner surface of the body member and adapted to engage the skin of the user, the compressible portion extending radially toward the center of the headset. In some embodiments, the at least one compressible portion is adapted, when the headset is donned by the user, to be urged against skin of the user and to compress against the skin, such that the compressible portion extends radially toward the center of the headset to a greater degree when the headset is not donned by the user, than when the headset is donned by the user. In some embodiments, the at least one compressible portion is mounted on an inner surface of the anterior section.

In some embodiments, the at least one compressible portion comprises a compressible portion mounted onto a flexible leaf connected to the anterior section, the flexible leaf having a rest state and an extended state. In some such embodiments, in the extended state, a curvature of the flexible leaf corresponds to a curvature of the scalp of a user donning the headset. In some embodiments, the at least one compressible portion includes the at least one electrode and an electrode housing surrounding the at least one electrode, the electrode housing including at least one hollow chamber adapted for trapping liquid emitted from the at least one electrode when the at least one compressible portion and the at least one electrode are compressed.

In some embodiments, the anterior section including at least one positioning indicator enabling the user, during donning of the headset, to center the anterior section on the head of the user such that the at least one electrode or the at least one sensor is accurately positioned when the headset is donned.

In some embodiments, the body member further includes at least one posterior section disposed adjacent the posterior ends of the arm members. In some embodiments, the at least one posterior section includes an at least partially tapered section, tapering from a first portion having a first width to a second portion having a second width, smaller than the first width. In some embodiments, the at least partially tapered section terminates, at the second portion, in the closure mechanism.

In some embodiments, the at least one electrode includes at least one posterior electrode at least partially mounted on the posterior section. In some embodiments, at least one of the at least one posterior electrode being configured, when the headset is donned, to be disposed above at least one occipital nerve branch of the user. In some embodiments, at least one of the at least one posterior electrode including a transcranial stimulation electrode configured, when the headset is donned, to be disposed above an occipital brain region of the user.

In some embodiments, the at least one posterior electrode includes a first posterior electrode and a second posterior electrode, each of the first and second posterior electrodes having a first end, a second end, a height, and a length, the heights of the first and the second posterior electrodes being in the range of 5 mm to 35 mm, the first and second posterior electrodes arranged horizontally alongside one another on the elongate body member such that the second end of the first posterior electrode is adjacent the first end of the second posterior electrode with a distance therebetween, the distance being in the range of 1 mm to 10 mm, and a length consisting of the length of the first electrode, the length of the second electrode, and the distance, is in the range of 10 mm to 55 mm.

In some embodiments, the first posterior electrode is configured, when the headset is donned, to be disposed above a first occipital nerve branch on one side of the user's head, and the second posterior electrode is configured, when the headset is donned, to be disposed above a second occipital nerve branch on the one side of the user's head, In some embodiments, each of the first and second posterior electrodes includes a liquid-absorbent layer having a biocompatible contact surface, the contact surface adapted to be juxtaposed against the skin surface, and an electrode backing, attached to the liquid-absorbent layer, the backing containing at least one electrically conductive material or element, the conductive material or element being electrically connected with the liquid-absorbent layer, when the liquid-absorbent layer is filled with liquid.

In some embodiments, the first and second posterior electrodes are disposed on a joint substrate, the joint substrate including a first contact portion in electrical contact with the electrode backing of the first posterior electrode and a second contact portion in electrical contact with the electrode backing of the second posterior electrode.

In some embodiments, the ratio between an area of the first posterior electrode and an area of the second posterior electrode is in the range of 0.5-2. In some such embodiments, the area of the first posterior electrode is equal to the area of the second posterior electrode.

In some embodiments, a joint contact surface including the contact surfaces of the first and second posterior electrodes has a generally frusto-conical outline defining a base and a curved tip, connected by a pair of side curves, and the first posterior electrode and the second posterior electrode are mirror image symmetrical about a horizontal axis of symmetry. In some embodiments, a curvature of the tip corresponds to that of a circle having a radius not greater than 10 mm, a curvature of the side curves corresponds to that of a circle having a radius of at least 50 mm, and an angle between the second end of the first posterior electrode and the horizontal axis of symmetry is in the range of 75-105 degrees.

In some embodiments, the posterior section includes a posterior section housing having at least one flexible surface and having the posterior electrode housed therein. In some such embodiments, the at least one flexible surface is adapted such that, when the headset is donned by a user and the at least one posterior electrode engages the scalp of the user, pressure applied to the at least one flexible surface causes deformation of the at least one flexible surface resulting in a conductive fluid being emitted from the at least one posterior electrode toward the scalp of the user, thereby to reduce the impedance between the at least one posterior electrode and the scalp of the user. In some embodiments, the processing unit is disposed within the anterior section. In other embodiments, the processing unit is disposed within one of the arm sections.

In some embodiments, the processing unit includes a control element, functionally associated with the at least one electrode or with the at least one sensor, and configured to control operation of the at least one electrode or of the at least one sensor.

In some embodiments, the processing unit includes a receiver, functionally associated with the at least one electrode or with the at least one sensor, and configured to receive input from the at least one electrode or from the at least one sensor.

In some embodiments, the processing unit includes a transceiver, functionally associated with the at least one electrode or with the at least one sensor, and configured to control operation of and to receive input from the at least one electrode or the at least one sensor. In some embodiments, the transceiver includes a wireless communication transceiver configured to receive control instructions from a remote control device using a wireless communication protocol.

In some embodiments, the processing unit is mounted on the body member and communicates with the at least one electrode or at least one sensor via at least one electrical conductor. In some embodiments, the at least one electrical conductor extends along at least one of the arm sections.

In some embodiments, the at least one of the arm sections includes a hinge adapted for folding the arm section, and wherein the at least one electrical conductor extends through the hinge. In some embodiments, when the at least one arm section is folded at the hinge, current cannot be conducted through the hinge.

In some embodiments, at least one of the arm sections includes a size-adjustment mechanism, and wherein the electrical conductor extends through the size-adjustment mechanism.

In some embodiments, the headset further includes a power supply, functionally associated with the at least one electrode or with the at least one sensor, providing electrical current to the at least one electrode or to the at least one sensor for operation thereof. In some embodiments, the power supply also being functionally associated with the processing unit for providing electrical current thereto for operation thereof. In some embodiments, the power supply is disposed within or on the anterior section. In other embodiments, the power supply is disposed within or on one of the arm sections.

In some embodiments, the at least one electrode including a stimulating electrode configured to deliver electrical stimulation to a skin surface of the head of the user. In some embodiments, the stimulating electrode is disposed, when the headset is donned, above a nerve or nerve junction and being configured to deliver the electrical stimulation to the nerve or nerve junction. In some embodiments, the stimulating electrode is configured to deliver the electrical stimulation to at least one brain region of the user.

In some embodiments, the at least one electrode includes a sensing electrode configured to sense at least one electrical parameter of a body portion of the user.

In some embodiments, at least one of the at least one electrode includes at least one side electrode mounted on an inner surface of the body member. In some embodiments, the at least one side electrode configured to be disposed, when the headset is donned, above at least one of the zygomaticotemporal nerve and the auriculotemporal nerve of the user. In some embodiments, the at least one side electrode includes a transcranial stimulation electrode configured to be disposed, when the headset is donned, above the temple of the user and anterior to the ear of the user or immediately behind the ear of the user.

In some embodiments, the headset further includes a nose bridge portion, attached to the body member at a center thereof, and positionable on a nose bridge of the user during donning the headset. In some embodiments, the nose bridge portion is removably and replaceably attached to the body member. In some embodiments, the nose bridge portion includes at least one pliable portion adapted to contact the user's nose or nose bridge and to follow the contours thereof.

In some embodiments, the headset further includes at least one of an optical member and an ocular member, attached to the body member at a center thereof, and positionable over eyes of the user during donning of the headset. In some embodiments, the at least one of an optical member and an ocular member is removably and replaceably attached to the body member.

In some embodiments, the headset further includes a nose bridge portion and an optical member, both removably and replaceably attachable to the body member via the same attachment point.

In some embodiments, the at least one sensor includes a spatial orientation sensor configured to sense an angular position of the headset, when donned. In some embodiments, the sensor includes a sensor selected from the group consisting of a temperature sensor, an orientation sensor, a blood pressure sensor, a pulse oximetry sensor, an electrical conductivity sensor, a sensor for measuring skin conductance response (SCR), a sensor for measuring impedance plethysmograph (IPG), a sensor for measuring electroencephalogram (EEG), and a sensor for measuring electromyograph (EMG).

In accordance with some teachings of the present invention there is provided a method of donning a headset on the head of a user, the method including:

providing a headset as described herein, the headset being in a rest state;

positioning the headset adjacent the head of the user, such that the posterior ends of the arm members engage sides of the head of the user, while the body member is in an open state; and pushing the headset rearward, until the closure mechanism closes the body member into the closed state, such that the headset fully encircles the head of the user while the anterior section engages the forehead of the user.

In some embodiments, pushing further includes, during motion of the headset rearward, the posterior ends of the arm sections plowing through the hair and clearing an area of the scalp of the user for physical contact of the at least one electrode or the at least one sensor therewith.

In some embodiments, the method further includes, when the body member is in the closed state, adjusting a size of the body member by simultaneously pushing against the anterior section and a section of the body member adjacent the closure mechanism, so as to adjust the length of at least one size-adjustment mechanism of the headset.

In some embodiments the method further comprises, subsequent to pushing the headset rearward, applying pressure to a flexible surface adjacent the at least one electrode and compressing the at least one electrode to release a conductive fluid from the electrode to an area between the at least one electrode and the scalp of the user, thereby to reduce the impedance between the at least one electrode and the scalp.

In accordance with additional teachings of the present invention there is provided an electrode system for stimulation of the anterior portion of the head of a user, the system including a first anterior electrode and a second anterior electrode, each of the first and second anterior electrodes having a first end, a second end, a height, and a length, wherein:

the heights of the first and the second anterior electrodes, at a maximal point thereof, being in the range of 10 mm to 40 mm, the first and second anterior electrodes are configured to be arranged, when disposed on the user's head, horizontally alongside one another, such that the second end of the first anterior electrode is adjacent the first end of the second anterior electrode with a distance therebetween, the distance being in the range of 1 mm to 15 mm, and a length consisting of the length of the first electrode, the length of the second electrode, and the distance, is in the range of 20 mm to 55 mm.

In some embodiments, the first anterior electrode is configured, when the headset is donned, to be disposed above the supratrochlear nerve on one side of the user's head, and the second anterior electrode is configured, when the headset is donned, to be disposed above the supraorbital nerve on the one side of the user's head, In some embodiments, each of the first and second anterior electrodes includes a liquid-absorbent layer having a biocompatible contact surface, the contact surface adapted to be juxtaposed against the skin surface, and an electrode backing, attached to the liquid-absorbent layer, the backing containing at least one electrically conductive material or element, the conductive material or element being electrically connected with the liquid-absorbent layer, when the liquid-absorbent layer is filled with liquid.

In some embodiments, the first and second anterior electrodes are disposed on a joint substrate, the shared substrate including a first contact portion in electrical contact with the electrode backing of the first anterior electrode and a second contact portion in electrical contact with the electrode backing of the second anterior electrode.

In some embodiments, the ratio between an area of the first anterior electrode and an area of the second anterior electrode is in the range of 0.5-2. In some such embodiments, the area of the first anterior electrode is equal to the area of the second anterior electrode. In some embodiments, a contour of the first anterior electrode is identical to a contour of the second anterior electrode.

In some embodiments, the first and second anterior electrodes extending, at a lower end thereof, along a single concave contour defined between first and second boundary points disposed at opposite ends of the concavity and adapted to generally follow the outline of the user's eyebrows, wherein:

$$A/L \geq 0.5 \text{ mm}$$

A being an area bounded by a line between the boundary points of the concavity, and the concavity;
L being a length of the line between the boundary points;
the length (L) being at least 10 mm;

wherein a line disposed between a first point on the concave contour and a second point on the perimeter, on a side opposite the concave contour, and aligned in perpendicular fashion with respect to the contour at the first point, has a length H, wherein, over an entirety of the concave contour, $$H_{max}/H_{min} \leq 2.5,$$

$H_{max}$ being a maximum value of H over the entirety; and
$H_{min}$ being a minimum value of H over the entirety.

In some embodiments, an angle between the line and the second end of the first anterior electrode adjacent the distance is in the range of 40-110 degrees.

In accordance with additional aspects of the teachings herein, there is provided an electrode system for stimulation of the occipital portion of the head of a user, the system including a first posterior electrode and a second posterior electrode, each of the first and second posterior electrodes having a first end, a second end, a height, and a length, wherein:

the heights of the first and the second posterior electrodes being in the range of 5 mm to 35 mm, the first and second posterior electrodes are configured to be arranged, which disposed on the user's head, horizontally alongside one another, such that the second end of the first posterior electrode is adjacent the first end of the second posterior electrode with a distance therebetween, the distance being in the range of 1 mm to 10 mm, and a length consisting of the length of the first electrode, the length of the second electrode, and the distance, is in the range of 10 mm to 55 mm.

In some embodiments, the first posterior electrode is configured, when the headset is donned, to be disposed above a first occipital nerve branch on one side of the user's head, and the second posterior electrode is configured, when the headset is donned, to be disposed above a second occipital nerve branch on the one side of the user's head, In some embodiments, each of the first and second posterior electrodes includes a liquid-absorbent layer having a biocompatible contact surface, the contact surface adapted to be juxtaposed against the skin surface, and an electrode backing, attached to the liquid-absorbent layer, the backing containing at least one electrically conductive material or element, the conductive material or element being electrically connected with the liquid-absorbent layer, when the liquid-absorbent layer is filled with liquid.

In some embodiments, the first and second posterior electrodes are disposed on a joint substrate, the joint substrate including a first contact portion in electrical contact with the electrode backing of the first posterior electrode and a second contact portion in electrical contact with the electrode backing of the second posterior electrode.

In some embodiments, the ratio between an area of the first posterior electrode and an area of the second posterior electrode is in the range of 0.5-2. In some such embodiments, the area of the first posterior electrode is equal to the area of the second posterior electrode.

In some embodiments, a joint contact surface including the contact surfaces of the first and second posterior electrodes has a generally frusto-conical outline defining a base and a curved tip, connected by a pair of side curves, and wherein the first posterior electrode and the second posterior electrode are mirror image symmetrical about a horizontal axis of symmetry. In some such embodiments, a curvature of the tip corresponds to that of a circle having a radius not greater than 10 mm, a curvature of the side curves corresponds to that of a circle having a radius of at least 50 mm, and an angle between the second end of the first posterior electrode and the horizontal axis of symmetry is in the range of 75-105 degrees.

BRIEF DESCRIPTION OF THE FIGURES

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like functionalities, but not necessarily identical elements.

In the drawings:

FIGS. 3A, 3B, 3C, and 3D are planar top view illustrations of steps of a method of donning the inventive headset of FIGS. 1A and 1B on a head of a user;

FIGS. 4A and 4B are perspective views of steps of a method of donning the inventive headset of FIGS. 1A and 1B, FIG. 4A corresponding to the donning step shown in FIG. 3C, and FIG. 4B corresponding to the donning step shown in FIG. 3D;

FIGS. 5A and 5B are planar top view illustrations of an anterior member of the inventive headset of FIGS. 1A and 1B in a rest state and a donned state respectively;

FIGS. 18A and 18B are schematic illustrations of an embodiment of electrical conductors embedded in a hinged arm member, which electrical conductors are suitable for use in inventive headsets according to the teachings herein, FIG. 18A illustrating the arm member in a folded position, and FIG. 18B illustrating the arm member in an open position, respectively;

FIG. 19 is schematic illustrations of an embodiment of electrical conductors embedded in a size adjustment mechanism, which electrical conductors are suitable for use in inventive headsets according to the teachings herein;

DETAILED DESCRIPTION

Device and methods are described herein that include a headset with one or more integrated electrodes for applying electrical stimulation to peripheral nerves, cranial nerves and brain regions. The inventive headset is a head mounted construction that can be served as a platform for applying electrical stimulation to treat various conditions such as migraine and tension type headaches, cluster headache, fibromyalgia, anxiety, depression, post-traumatic stress disorder (PTSD), anxiety, obsessive compulsive disorder (OCD), insomnia, epilepsy, attention deficit hyperactivity disorder (ADHD), Parkinson's disease, Alzheimer's disease, obesity, multiple sclerosis, Traumatic brain injury (TBI) and stroke. The inventive headset may facilitate motor and cognitive learning and may induce relaxation. The inventive headset may also serve as a platform for various sensors, in order to detect and/or assess various conditions.

The stimulation electrodes and the quality of its contact with the scalp are a fundamental aspect in the functionality of the invented apparatus. Ensuring optimal conductivity between the electrodes and the scalp is essential for proper transfer of the electrical current to the target tissues, which is the basis for an effective treatment. Improper conductivity may result in failure of the therapy, unpleasant sensation and even skin irritation due to "hot spots" of high current density. The inventors have also found that non-invasive application of electrical current to the head region, no matter which indication it is applied for, poses numerous challenges including stimulation in the presence of hair, extremely high sensory sensitivity of the scalp, criticality of robust contact and optimal electrical conductivity between the electrodes and the scalp despite variations in head size and contours, and need for precise placement of the stimulating electrodes above the target nerve branches and brain regions.

Several aspects of the present invention relate to features that are aimed at ensuring that the electrical current is properly delivered from the electrodes to the target tissues and for treating and assessing the head region in an effective and comfortable manner.

Figure 1A:
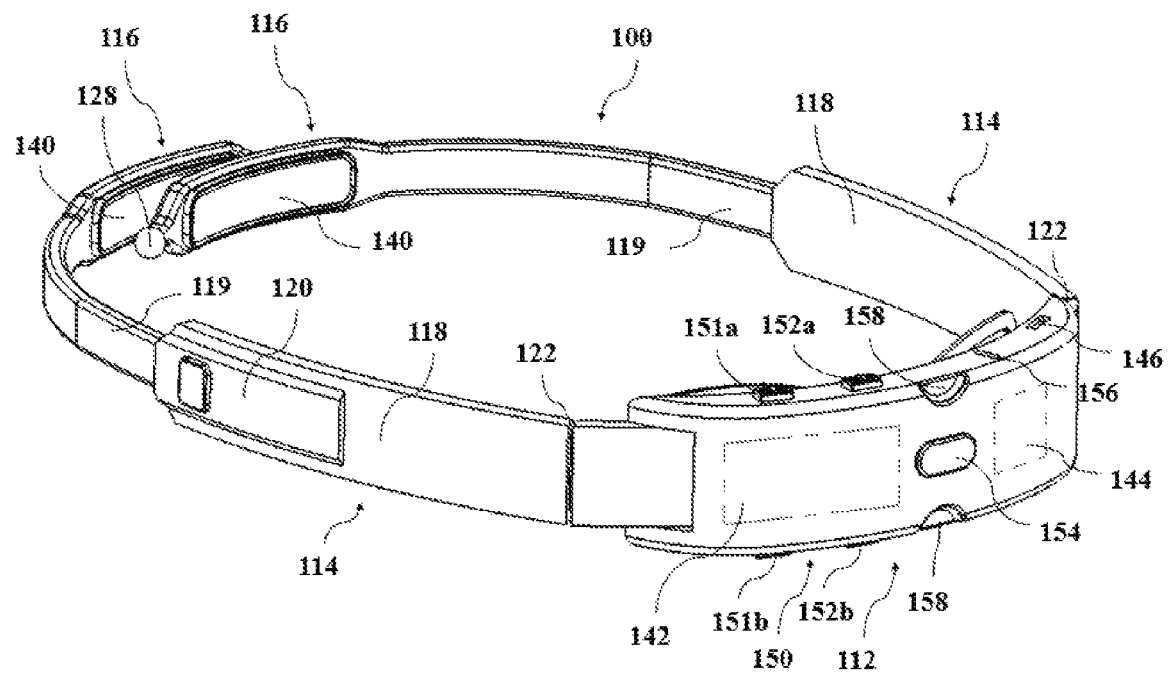
FIGS. 1A and 1B are perspective view illustrations of an embodiment of an inventive headset according to the teachings herein, the headset being in a rest state.
Figure 1B:
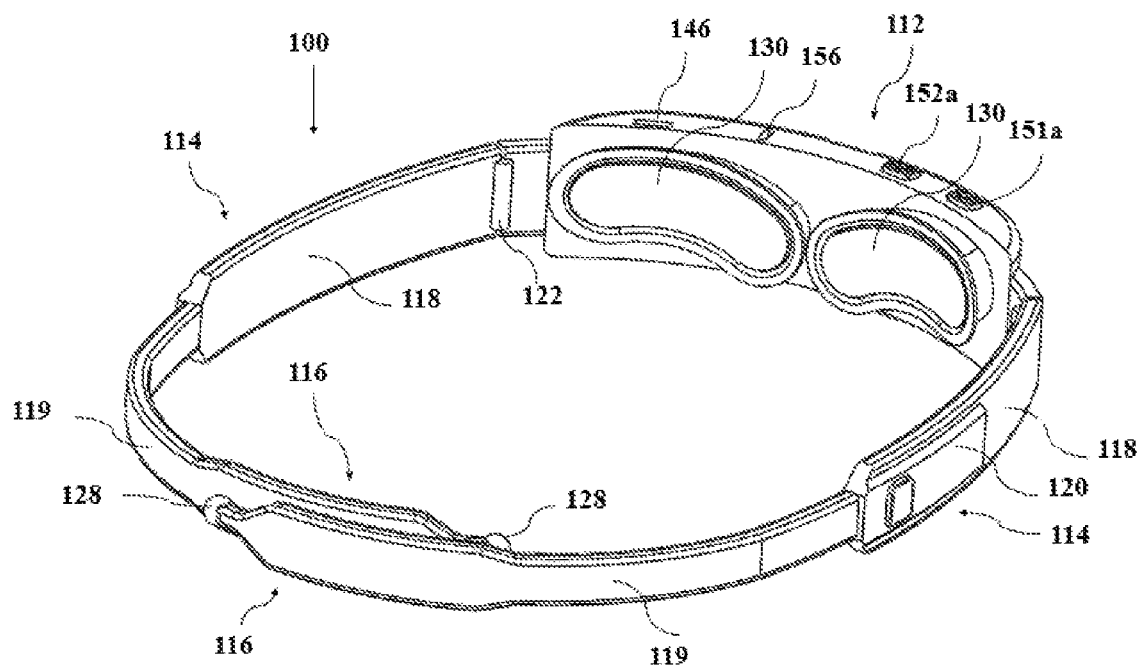
Figure 1C:
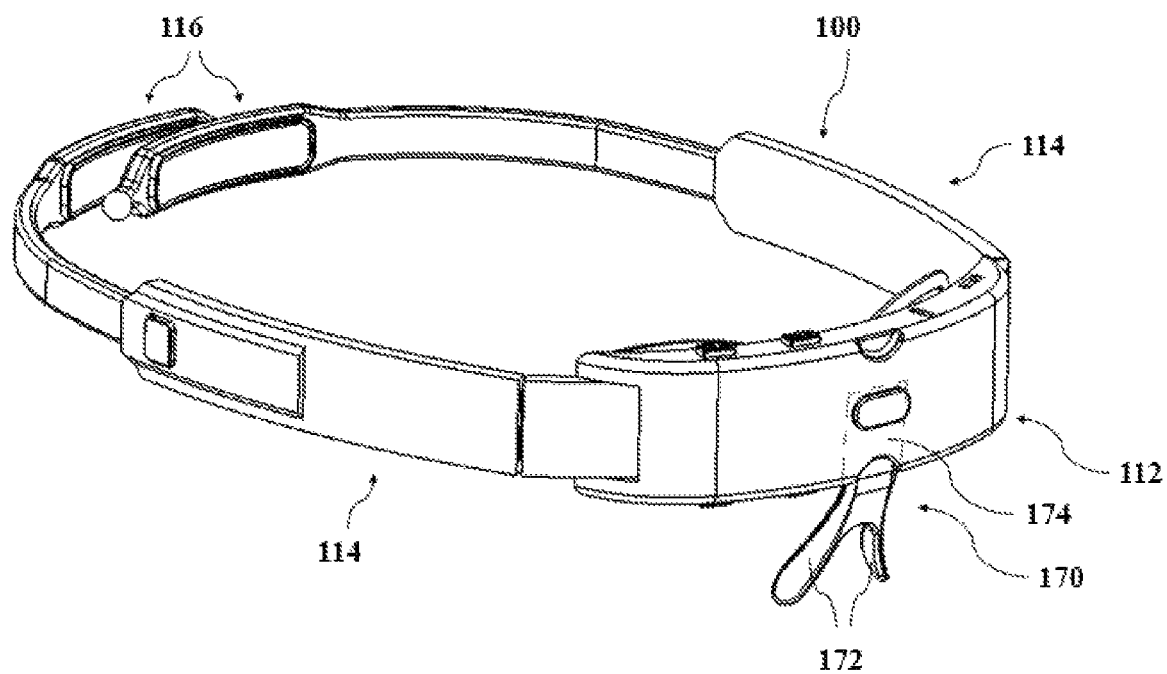
FIG. 1C is a perspective view illustration of an embodiment of the inventive headset of FIGS. 1A and 1B, including a nose bridge support member.

Reference is now made to FIGS. 1A and 1B, which are perspective view illustrations of an embodiment of an inventive headset according to the teachings herein, the headset being in a rest state, and to FIG. 1C, which is a perspective view illustration of an embodiment of the inventive headset of FIGS. 1A and 1B, including a nose bridge support member.

As seen, an inventive headset 100 according to an embodiment of the teachings herein may be configured to include an anterior member 112 connected to a pair of flexible arm members 114, each terminating in a posterior member 116. Anterior member 112, flexible arm members 114, and posterior members 116 together form the headset body.

It is appreciated that in some embodiments, the inventive headset may comprise an elongate member formed of a flexible material, and including an anterior section, arm member sections, and posterior sections, without including explicitly identified anterior member, arm members, and posterior members. However, for the ease of description, the following description relates to an embodiment including a clearly defined anterior member, flexible arm members, and posterior members comprising end sections of the arm members.

In some embodiments, anterior member 112 is typically rigid, but in some embodiments may be at least partially flexible, or at least semi-rigid. In some embodiments, the anterior member 112 may be flexible and may include a rigid or semi-rigid member connected thereto, such that a degree of freedom exists between the flexible anterior member 112 and the rigid member connected to it that allows the flexible anterior member 112 to flex. In some embodiments, anterior member 112 may be rigid or semi-rigid, and may house a flexible member therein, such that the flexible member may be able to flex within the anterior member 112, for example as described hereinbelow with reference to FIG. 14B. The anterior member 112 may be formed of plastic or of any other suitable material. The anterior member 112 is suited to encompass the forehead region of a person, and thus has a curvature generally suited to the shape of a human head.

As described in further detail hereinbelow with reference to FIGS. 14A to 14C, each of arm members 114 comprises a flexible or semi rigid material, for example a metal such as stainless steel, a plastic such as polypropylene, polyurethane, or polyethylene, or a combination of metal and plastic sections. In some embodiments, each arm member 114 comprises a flexible temple arm portion 118 adjacent the anterior member 112, a posterior arm portion 119 including the posterior member 116, and a size adjustment mechanism 120 disposed between the temple arm portion 118 and the posterior arm portion 119. In some embodiments, anterior member 112, arm members 114, and posterior members 116, together form a monolithic structure. As seen in FIGS. 1A and 1B, in the rest state, the posterior arm portions 119 have a rest state curvature.

It is a particular feature of the teachings herein that arm members 114 are resilient, and have a predefined preload pushing the arm members toward each other, such that when the headset is in the open state, as shown in FIG. 3A, the arm members 114 drive the headset to the closed or rest states, as explained in further detail hereinbelow with reference to FIGS. 14A to 14C.

Arm members 114 are semi-rigid, and not fully rigid, so as to allow the arm members 114 to conform to the user's head shape and/or to absorb pressure applied to different locations on the arm members without resulting in movement of treating portions of the device, described hereinbelow, from their correct positions. For example, when the user lies down and the side of the user's head is supported, or engages a surface on which the user is lying down, pressure is applied to arm members 114, and the partial flexibility of the arm members absorbs this pressure and ensures that the treating and/or sensing components of headset 100 remain properly positioned.

In some embodiments, each temple arm portion 118 includes a hinge 122, useful for folding the arm members 114 to lie parallel to the anterior member 112, as described hereinbelow with reference to FIGS. 17A and 17B.

In some embodiments, each posterior member 116 comprises a terminal portion of the posterior arm portion 119 having a tapered end terminating in a closure mechanism 128, described in further detail hereinbelow with reference to FIGS. 16A and 16B.

Anterior member 112 may be configured to contain, or to have removably attached thereto, on an interior surface thereof, one or more anterior electrode systems 130, and each of posterior members 116 may be configured to contain, on an interior surface thereof, one or more posterior electrode systems 140. Each of electrode systems 130 and 140 comprises an electrode base and a disposable electrode unit, which may, in some embodiments, be structured and functional as described hereinbelow with reference to FIGS. 6A to 9B.

In some embodiments, electrode systems 130 may comprise anterior electrodes adapted to be located at the supraorbital region of the head, over the trigeminal nerve branches for stimulation thereof, which may be structured and functional as described hereinbelow with reference to FIGS. 10A and 10B, or may be electrodes suitable for transcranial stimulation of the frontal and prefrontal region of the brain.

In some embodiments, electrode systems 140 may comprise posterior electrodes adapted to be located at the occipital region of the head, over the occipital nerve branches for stimulation thereof, which may be structured and functional as described hereinbelow with reference to FIGS. 11A to 13B, or may be electrodes suitable for transcranial stimulation of the occipital region of the brain.

In some embodiments, one or more of electrode systems 130 and 140 may comprise sensing electrodes, configured to sense at least one electrical parameter of a body portion of said user, such as, for example, electroencephalogram (EEG), skin conductance response (SCR), impedance plethysmograph (IPG), electromyograph (EMG), and the like.

It is appreciated that headset 100 may include additional electrodes, as shown in FIGS. 22A to 23B, the additional electrodes having similar structure and/or functionality to those of electrode systems 130 and 140. It is further appreciated that electrode systems 130 and/or 140 may be obviated, or moved to other locations on headset 100, as suitable for stimulating specific nerves or nerve sets, specific brain regions, or for sensing specific parameters. For example, electrode systems 140 may be moved to be along the flexible arm members 114. As another example, the headset 100 may include only a single pair of electrode systems located on arm members 114, which electrodes may be configured to be positioned, when the headset is donned, under the hair, while electrode systems 130 and 140 may be obviated.

Anterior member 112 may be configured to contain an electronic circuit 142, which may be configured to be electrically coupled by conductive wires (not shown) to a power source 144, such as a battery, and to electrodes systems 130 and 140. As described hereinbelow with reference to FIGS. 18A to 19, in some embodiments, at least a portion of the conductive wires extends to posterior electrode systems 140 via arm members 114.

In some embodiments, the electronic circuit 142 and/or the battery 144 may be external to headset 100, and/or may communicate remotely with headset 100.

The electronic circuit 142 may be configured to include a stimulation circuit, a microprocessor, a charging circuit and a user interface as described hereinbelow with reference to FIG. 24.

The stimulation circuit may be configured to produce biphasic, charged balanced electrical pulses, mono-phasic electrical pulses, and/or direct current stimulation.

According to still further features of the described preferred embodiments, the stimulation circuit may be configured to produce electrical stimulation within an intensity range of 0-60 mA, 0-40 mA, 0-20 m, or 0-15 mA.

According to still further features of the described preferred embodiments, the stimulation circuit may be configured to produce stimulation pulses with a duration of 10-1000 μsec, 50-500 μsec, 100-500 μsec, 100-450 μsec, 150-400 μsec or 200-450 μsec.

According to still further features of the described preferred embodiments, the stimulation circuit may be configured to produce stimulation pulses at a frequency of 1-20,000 Hz, 1-10,000 Hz, 1-500 Hz, 10-300 Hz, 10-250 Hz, 20-180 Hz, 30-180 Hz or 40-100 Hz.

According to still further features of the teachings herein, headset 100, and specifically the electronic circuit 142, may be suited for applying transcranial electrical stimulation using suitable methods such as Transcranial Direct Current Stimulation (tDCS), Transcranial Alternating Current Stimulation (tACS), and Transcranial Random Noise Stimulation (tRNS), as described hereinabove in the Background section.

Specifically, use of a headset for transcranial electrical stimulation requires a higher depth of penetration of the stimulation current through tissues of the head in order to directly affect brain regions. In order to achieve such deeper current penetration, combinations of electrodes located distantly to one another may be activated simultaneously. For example, an anterior electrode may be activated simultaneously with a posterior electrode. Additionally, the locations of the electrodes may be modified so as to increase the distance between adjacent electrodes, thereby to provide deeper penetration of current.

According to still further features of embodiments of the teachings herein, headset 100 may be configured to connect to an external electronic circuit and/or stimulation circuit, and thereby to transfer electrical current from an external stimulator to the electrode systems 130 and/or 140. In some embodiments, headset 100 may be configured to connect to at least one external electrode that may be located at various areas of the body. In some embodiments, headset 100 may be configured to connect to an external electronic circuit and processor in order to transfer signals from sensors disposed on the headset 100 to the external processor.

In some embodiments, battery 144 may be disposed within anterior member 112, and may be recharged by plugging a charger into charging port 146 located, according to certain embodiments, on anterior member 112.

Anterior member 112 may also be configured to include, on an external surface thereof, user controls and interface 150. That said, in some embodiments, other portions of the inventive headset 100, such as posterior members 116 or arms 114, may be configured to include user interface 150. In some embodiments, user interface 150, or an additional user interface (not shown) may be external to headset 100 and may communicate with headset 100 remotely, using wired or wireless communication, as explained hereinbelow with reference to FIG. 24.

As explained hereinabove, electronic circuit 142 and user interface 150 are configured to control and/or activate electrodes included in headset 100. In some embodiments, user interface 150 is configured to control and/or activate at least two, and in some embodiments more than two, pairs of electrodes. As such, in some embodiments, the stimulation circuit and/or user interface 150 are configured to enable activation of a specific electrode or of a specific pair, or channel, of electrodes, as well as adjustment of the intensity of current supplied by the activated electrodes or of other stimulation parameters of the activated electrodes. In some embodiments, any subset of the electrodes may be activated simultaneously, and in some embodiments specific subsets are predefined, for example during manufacture of the electronic circuit 142. In some such embodiments, user interface 150 enables control not only of a specific electrode or of a specific channel, but also of activated subsets of the electrodes.

In some embodiments, user controls and interface 150 includes a pair of anterior intensity buttons 151*a* and 151*b* for respectively increasing and decreasing the intensity of stimulation provided by anterior electrode systems 130, and a pair of posterior intensity buttons 152*a* and 152*b* for respectively increasing and decreasing the intensity of stimulation provided by posterior electrode systems 140. It is appreciated that user control and interface 150 may include similar intensity buttons for each electrode included in the headset 100.

The user controls and interface 150 may further include a mode changing button 154 for activating and disabling the electronic circuit 142, as well as for changing between modes of operation of headset 100. For example, headset 100 may have multiple preset modes of operation, such as a sleep mode, a maintenance mode, and a treatment mode, and repeated operation of button 154 may switch between these modes, in addition to turning the headset on and off.

An operation indicator 156, such as an LED light, may form part of user controls and interface 150 and may be disposed on an exterior surface of anterior member 112. Indicator 156 may indicate to a user when the headset 100 is turned on and/or when the electrode systems 130 and/or 140 are active, thereby helping the user prevent unwanted contact with the electrodes when these are operative.

In some embodiments, the user controls and interface 150 may further include an audio element (not shown), such as a speaker or buzzer, for providing to the user an audible indication of use of the headset 100, such as an indication of activation of the headset, shutting down of the headset, pressing a button on interface 150, changing the stimulation mode, and the like.

In some embodiments, the user controls and interface 150 may further include at least one positioning indicator 158, for example in the form of notches in the center of anterior member 112. The positioning indicator 158 assists the user in donning the headset correctly by providing verification for headset placement, for example by helping the user confirm that the positioning indicator 158 is aligned with the user's nose.

As explained hereinabove, the electronic circuit and the user interface are configured to control and/or activate electrodes included in headset 100. In some embodiments, the user interface is configured to control and/or activate at least two, and in some embodiments more than two, pairs of electrodes. As such, in some embodiments, the stimulation circuit and/or the user interface are configured to enable activation of a specific electrode or of a specific pair, or channel, of electrodes, as well as adjustment of the intensity of current supplied by the activated electrodes or of other stimulation parameters of the activated electrodes. In some embodiments, any subset of the electrodes may be activated simultaneously, and in some embodiments specific subsets are predefined, for example during manufacture of the electronic circuit. In some such embodiments, the user interface enables control not only of a specific electrode or of a specific channel, but also of activated subsets of the electrodes.

Figures 2A, 2B:
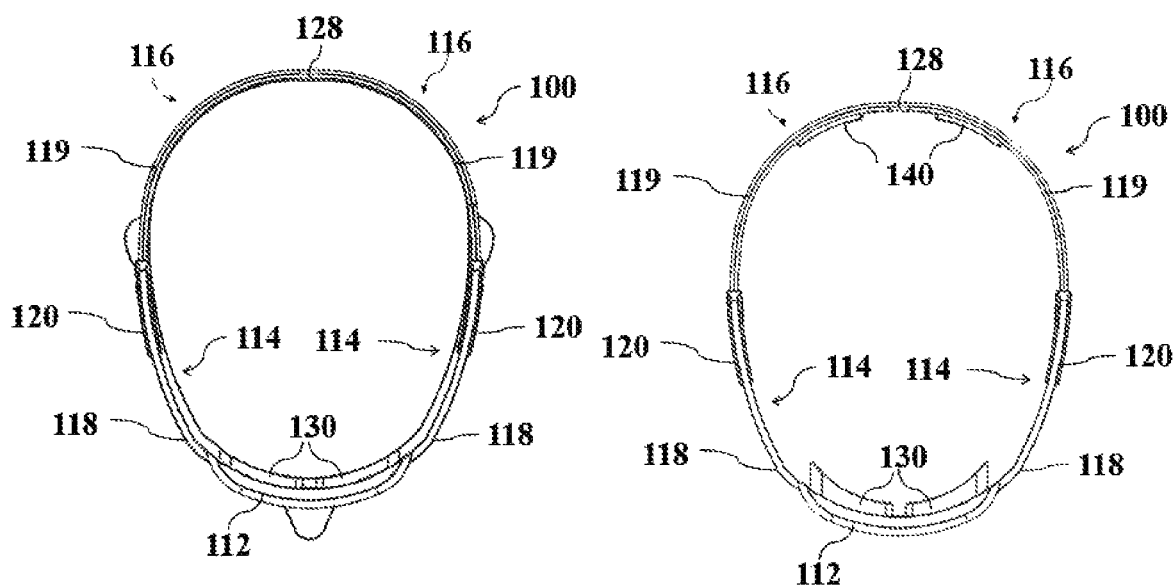
FIGS. 2A and 2B are planar top view illustrations of the inventive headset of FIGS. 1A and 1B in a closed state, FIG. 2A being positioned on the head of a user and FIG. 2B being free, respectively.

As seen from comparison of FIGS. 1A to 2B, headset 100 has a fixed length in the rest state, open state, and closed state. In some embodiments, the circumference of headset 100 in the closed state, illustrated in FIGS. 2A and 2B, is not greater than 65 cm, not greater than 63 cm, or not greater than 61 cm. In some embodiments, the circumference of headset 100 in the closed state, illustrated in FIGS. 2A and 2B, is not less than 30 cm, not less than 35 cm, or not less than 40 cm.

Turning specifically to FIG. 1C, it is seen that in some embodiments anterior member 112 may further include a nose bridge support member 170, which may be configured to be located in the central area of anterior member 112. Nose bridge support member 170 may be rigid or semi-rigid, and may have two elongate portions 172 adapted to be aligned at both sides of the upper part of the nose and the nose bridge. Positioning the nose bridge support member 170 over the nose may allow the user to determine the rotational and longitudinal placement of headset 100, for example while donning the headset.

Nose bridge support member 170 may also be configured to further support anterior member 112 against gravity, thereby enabling the user to more easily don headset 100 and preventing the anterior member 112 from applying pressure, in a downward direction, on the eyebrows of the user.

In some embodiments, nose bridge support member 170 is removably and replaceably attached to anterior member 112 by one or more tabs 174, configured to be inserted into corresponding slots in anterior member 112, and may be detached from the anterior member 112 by pulling tabs 174 out of the slots in which they are housed. In some embodiments, the slot for housing tab 174 is located at the center of anterior member 112.

A nose bridge support member 170 of various sizes and shapes may be selected for individual users. In some embodiments, nose bridge support member 170 is sufficiently flexible and/or pliable so as to allow the user to manually adjust the nose bridge for optimal adjustment to the nose of the user.

Reference is now made to FIGS. 2A and 2B, which are planar top view illustrations of the inventive headset of FIGS. 1A and 1B in a closed state, FIG. 2A being positioned on the head of a user and FIG. 2B being free, respectively.

A seen in FIGS. 2A and 2B, in the closed state of headset 100 the arm members 114, which were pulled apart to open and/or don the headset 100, as described hereinbelow with reference to FIG. 3A, return inward toward each other, such that closure mechanism 128 is in the closed position and the headset 100 forms a circumferential headset suitable for encircling the user's head. As described in further detail hereinbelow with reference to FIGS. 3A to 3D, the curvature of arm members 114, and specifically of posterior arm portions 119, while the headset 100 is closed on a user's head, is dependent on the anatomical curvature of the user's head, and is adapted to conform thereto.

Figure 8A:
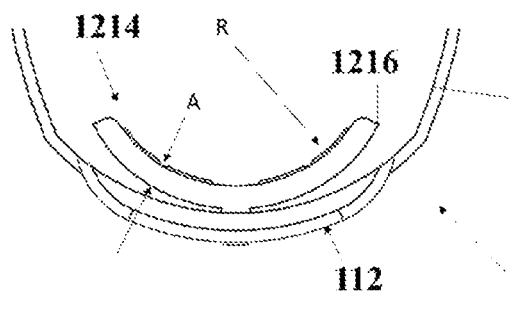
FIGS. 8A and 8B are planar top view illustrations of an inventive anterior member suitable for use with the inventive headset of FIGS. 1A and 1B according to another embodiment of the teachings herein, in a rest state and a donned state respectively.
Figure 8B:
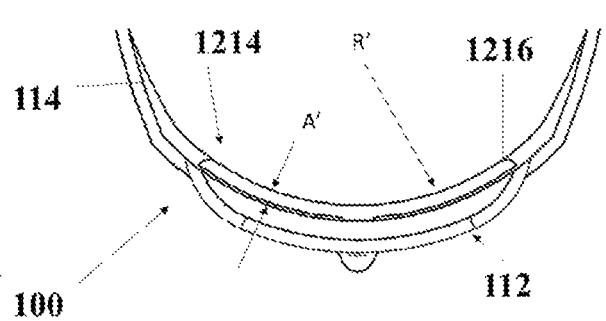

As described in further detail hereinbelow with reference to FIGS. 5A and 5B as well as FIGS. 8A and 8B, in the closed state pressure is applied to the forehead of the user by compression, flexing, and/or resilience of portions forming part of anterior member 112, such as, for example, compressible electrode systems 130, as seen from comparison of FIGS. 2A and 2B, or flexible electrode systems 130, as seen in FIGS. 8A and 8b.

Reference is now made to FIGS. 3A, 3B, 3C, and 3D, which are planar top view illustrations of steps of a method of donning the inventive headset of FIGS. 1A and 1B on a head of a user, and to FIGS. 4A and 4B, which are perspective views of steps of a method of donning the inventive headset of FIGS. 1A and 1B, FIG. 4A corresponding to the donning step shown in FIG. 3C, and FIG. 4B corresponding to the donning step shown in FIG. 3D.

As seen in FIG. 3A, in an initial step of donning headset 100, the user holds the headset with fingers 202 at arm members 114, and pulls arm members 114 away from each other so as to form a distance D therebetween and transition the headset 100 to an open state. In pulling the arm members 114 apart from each other, the user opposes the predefined preload on arm members 114. It is appreciated that the magnitude of the distance D is determined by the flexibility of arm members 114, the preload on the arm members, and the force applied by the user. In some embodiments, the distance D does not exceed the average width of a person's head. In some embodiments, the distance D is not greater than 12 cm, 15 cm, or 20 cm.

In some embodiments, the preload force applied onto the user's head by closure mechanism 128 or the ends of headset 100 may be defined by the following ratio:

$$P \sim EID/L^3 \quad (1)$$

where:

P is the force applied by the ends of headset 100 to the head of the user;

E is Young's modulus of the arm member 114;

I is the moment of inertia of the arm member 114;

D is the displacement of arm 114 relative to an axis of symmetry of the headset; and L is the length of one of arms 114.

As illustrated in FIG. 3A, the curvature of arm member 114, and specifically of posterior arm portion 119 thereof, can be defined by the radius of an imaginary circle, shown in the figure by a dashed line and indicated by reference numeral 206, partially circumscribed by the arm member. In the rest state (shown in FIGS. 1A and 1B), and in the open state prior to application of the headset to the user's head, the radius of such an imaginary circle is marked by reference $R_0$, and may have a length not greater than 15 cm, 13 cm, or 8 cm.

Turning additionally to FIG. 3B, it is seen that the user places the headset 100 such that closure mechanism 128 engages the temple area, in some embodiments, slightly anteriorly to the ears of the user. Due to the predefined preload on arm members 114, the closure mechanism 128, or the ends of headset 100, apply a force to the sides of the head of the user in a direction indicated by arrow 204. In some embodiments, the magnitude of the force is not greater than 20 N, 15 N, or 10 N.

It is a particular feature of the present invention that the curvature of the posterior arm portions 119 of arm members 114 is affected by contact of the arm members with the sides of the user's head, such that the curvature can be defined by a second imaginary circle partially circumscribed by the arm member and similar to circle 206 of FIG. 3A, the second imaginary circle having a radius $R_1$, greater than the radius $R_0$ of the imaginary circle of the rest state and open state of the headset 100, shown in FIG. 3A.

It is a further feature of the present invention that the curvature of the posterior arm portions 119 of arm members 114 is such that, when the closure mechanism 128 engages the sides of the head of the user, an angle $\alpha_1$ is formed between the ends of headset 100 and the head of the user. As described in further detail hereinbelow with reference to FIGS. 3C and 3D, the angle $\alpha_1$, together with the preload force applied by the arm members 114 to the sides of the head of the user, ensure that the ends of headset 100, and particularly the closure mechanism 128, maintains close proximity to the surface of the user's scalp while the user is donning headset 100. In some embodiments, the angle $\alpha_1$ is not greater than 90 degrees, 85 degrees, or 80 degrees, and is not smaller than 20 degrees, 30 degrees, 35 degrees or 40 degrees.

Turning to FIG. 3C, it is seen that the user pushes the headset 100 in a rearward direction, for example by holding arm members 114 in a similar manner to that in which a person dons glasses, or by pushing anterior member 112. Due to the preload of arm members 114, the ends of the headset 100 including closure mechanism 128 remain in close proximity to the surface of the user's scalp during such rearward motion, and plow under and between the user's hairs so as to enable direct contact between the posterior electrodes 140 and the scalp when the headset is donned, as seen clearly in FIG. 4A.

As the user pushes the headset 100 in a rearward direction, due to the engagement between the user's scalp and closure mechanism 128, a change occurs to the curvature of the arm members 114, the angle between the arm members 114 and the user's head, and the force applied to the user's head. Specifically, due to the fact that arm members 114 return toward each other along the curvature of the user's head, the force applied to the user's head in the direction indicated by arrow 208 and computed using ratio (1) above is less than the force applied at the beginning of the donning stage, shown in FIG. 3B and indicated by arrow 204. The angle between the arm members 114 and the user's head also decreases in size, such that angle $\alpha_2$ shown in FIG. 3C is smaller than angle $\alpha_1$ of FIG. 3B.

Additionally, the curvature of the posterior arm portions 119 of arm members 114 is affected by the rearward movement of the headset 100, and can be defined by a third imaginary circle partially circumscribed by the arm member and similar to circle 206 of FIG. 3A, the second imaginary circle having a radius $R_2$, greater than the radius $R_0$ of the imaginary circle of the rest state and open state of the headset 100, shown in FIG. 3A and smaller than the radius $R_1$ shown in FIG. 3B.

In some embodiments, when both parts of the closure mechanism 128 are in close proximity to one another, the two portions of closure mechanism 128 attract one another to close of headset 100, without requiring the user to actively close the headset 100 or manipulate the closure mechanism 128.

In FIGS. 3D and 4B, headset 100 is fully donned on the user's head, and closure mechanism 128 is closed at the rear of the user's head. Anterior member 112 engages the user's forehead such that the anterior electrode systems 130 engage the user's skin in the area of the supraorbital and supratrochlear nerves, and in some embodiments may stimulate these nerves, unilaterally or bilaterally. As seen clearly in FIG. 4B, the posterior electrode systems 140 of posterior members 116 engage the user's scalp, below the hair, at the rear of the user's head in the area of the occipital nerves, and may, in some embodiments, stimulate these nerves.

In some embodiments, in which closure mechanism 128 is a magnetic closure mechanism as described hereinbelow with reference to FIGS. 17A and 17B, a magnetic force $P_M$ is applied between the two portions of closure mechanism 128 as indicated by arrow 210, and may have a force magnitude greater than 0.5 N, 1.0 N, or 2.0 N.

When the headset 100 is donned for the first time, the user may reduce the length of the headset and adjust its size by pushing the posterior arm portions 119 and the anterior member 112 toward one another until the headset is tightened on the user's head, such that the length of size adjustment mechanisms 120 changes and thereby the size of the headset 100 is adjusted to the size of the user's head.

Additionally, in some embodiments, pressure applied to the anterior member 112 by tightening of the headset 100 around the user's head allows compressible components of the anterior member to compress as described hereinbelow with reference to FIGS. 5A to 5C, or flexible components of the anterior member to flex as described hereinbelow with reference to FIGS. 8A to 9B, thereby to ensure that electrodes 130 of the anterior member 112 fully engage the user's forehead, and that sufficient radial pressure is applied by headset 100 to the user's head.

Such radial pressure on anterior member 112 and on posterior members 116, which pushes them toward the user's head, ensures that the anterior and posterior electrode systems 130 and 140 maintain their suitable positions and remain in close contact with the user's skin. Specifically, in some embodiments, the radial pressure $P_R$ applied by the headset 100 on the user's head is in a direction indicated by arrow 212, and may have a force magnitude which is greater than 0 N, 1.0 N, or 3.0 N.

When the headset is in the closed position on the user's head, as shown in FIGS. 3D and 4B, the curvature of arm members 114, and specifically of posterior arm portions 119 thereof, ensures that when headset 100 is closed at the back of the user's head, the curvature aligns with the anatomical curvature of the user's head.

As described hereinabove, in some embodiments, additional electrode systems may be used to stimulate other nerves or nerve junctions, such as the zygomaticotemporal nerve and the auriculotemporal nerve (FIGS. 22A to 23B), or to transcutaneously stimulate brain regions such as the frontal, occipital, parietal and temporal lobes, or some electrodes may comprise sensing electrodes configured to sense electrical parameters of a portion of the user's head.

Figure 5C:
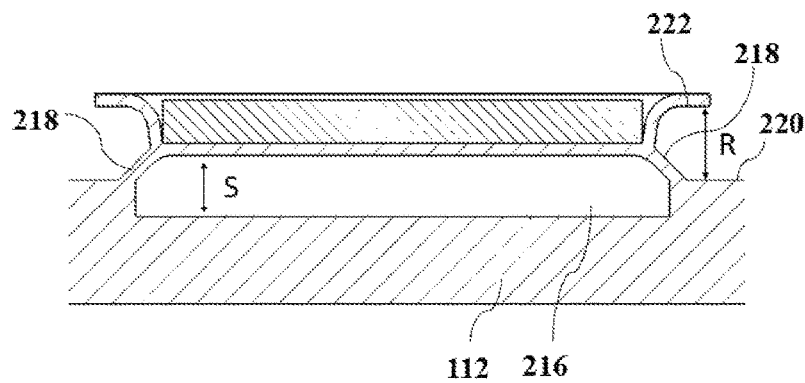
FIG. 5C is a sectional illustration, taken along the width of the anterior member of the inventive headset of FIGS. 1A and 1B, and illustrating the internal structure of the anterior member.

Reference is now made to FIGS. 5A and 5B, which are planar top view illustrations of an anterior member of the inventive headset of FIGS. 1A and 1B in a rest state and a donned state respectively, and to FIG. 5C, which is a sectional illustration, taken along the width of the anterior member of the inventive headset of FIGS. 1A and 1B, and illustrating the internal structure of the anterior member.

As seen, in some embodiments anterior member 112 includes a compressible portion 214, here shown as a compressible gasket surrounding the anterior electrode systems. In the rest state, or when the headset is not donned by the user and pressed against his forehead, the compressible portion extends radially inward from anterior member 112, and has a first radial depth, indicated in FIG. 5A by reference A. When the headset is donned by the user, the compressible portion 214 is compressed, and has a second radial depth, indicated in FIG. 5B by A'. The second radial depth A' is less than the first radial depth A, such that the compressible portion 214 applies pressure to the user's forehead, thereby ensuring that sufficient pressure is present between the headset 100 and the user's head in variable conditions, such that the headset, and treating components thereof, would not move from their intended location during use of the headset even if the user changes his or her position, for example lies down applying pressure to the posterior area of the headset or to a side portion of the headset. Additionally, the pressure applied by compressible portion 214 when it is compressed compensates for differences between the contour of the anterior member 112 and variable forehead contours, such that electrode systems 130 contact the user's forehead regardless of the exact anatomical structure of the user's forehead.

In some embodiments, the degree to which the compressible portion 214 is compressed when the headset 100 is donned, contributes to adjustment of the circumference of headset 100.

Figures 6A, 6B:
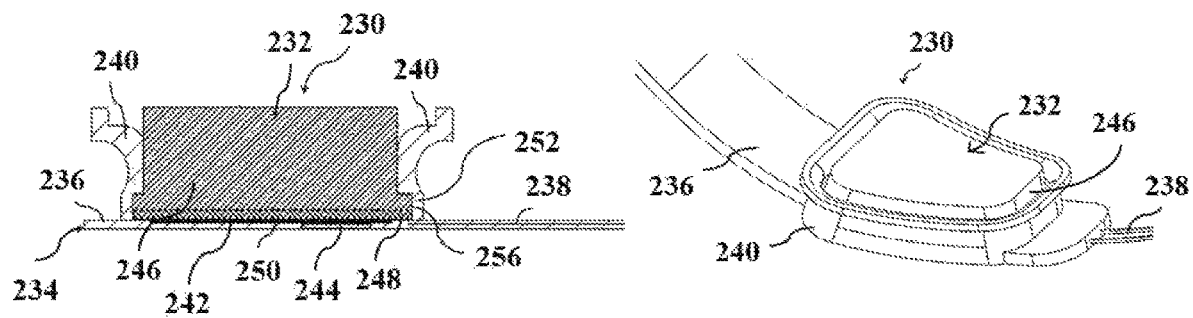
FIG. 6A is a cross-sectional view of an embodiment of an electrode system, including a disposable electrode unit disposed in an electrode base.
FIGS. 6B and 6C are perspective view illustrations of an electrode base with (FIG. 6B) and without (FIG. 6C) a multi-layered disposable electrode unit, according to an embodiment of the present invention.
Figure 6C:
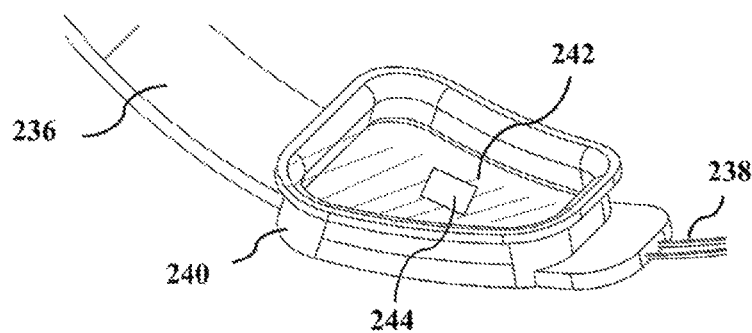

It is appreciated that there are many ways to construct a suitable compressible portion 214. For example, compressible portion 214 may be formed of a flexible and/or resilient rim or sealing arrangement surrounding the anterior electrode system 130, for example as shown in FIGS. 6A to 6C or substantially as described in PCT Application Publication Number WO2014/141213, entitled "HEADSET FOR TREATMENT AND ASSESSMENT OF MEDICAL CONDITIONS", which is hereby incorporated by reference as if fully set forth herein. In some such embodiments, the main purpose of the resilient rim is to seal around the periphery of electrode 130, and additionally, the resilient rim may function as the compressible portion 214.

As another example, compressible portion 214 may include electrode systems 130 that are mounted on a sponge, elastomer, or other compressible material or construction, such that when the anterior member 112 is pressed against the user's head, the sponge or other compressible construction is compressed, and the radial pressure on the user's forehead increases.

Another exemplary structure of compressible portion 214 is shown in FIG. 5C. In the structure shown in FIG. 5C, anterior member 112 includes a hollow portion 216 disposed beneath electrode system 130, and the electrode system 130 is supported by, or includes, an at least partially flexible base surface 218, such that when pressure is applied to the anterior member 112 the electrode systems 130 and/or other components of the anterior member are compressed into the hollow 216, for example by deformation of base surface 218, thereby creating the compressible portion. In some embodiments, the height of hollow 218, indicated in FIG. 5C by distance S, is greater than the distance between an inner surface 220 of anterior member 112 and an inner side 222 of the top surface of electrode system 130, which distance is indicated by R. Such construction enables the entire height of electrode system 130 to be compressed into hollow 216.

It is further appreciated that a compressible portion 214 according to the teachings herein need not necessarily form part of the anterior member, and may be placed in any location on the headset which is adapted to engage the user's skin, such as in posterior members 116 and/or along arm member 114.

Reference is now made to FIG. 6A, which is a cross-sectional view of an embodiment of an electrode system, including a disposable electrode unit disposed in an electrode base, and to FIGS. 6B and 6C, which are perspective view illustrations of an electrode base with (FIG. 6B) and without (FIG. 6C) a multi-layered disposable electrode unit, according to an embodiment of the present invention.

FIG. 6A is a cross section of an electrode system 230, including a disposable electrode unit 232 disposed in an electrode base 234, the combination of disposable electrode unit and electrode base being suitable for use in headsets as described herein, for example as electrodes 130 and/or 140. Electrode base 234 may be configured to be physically coupled to a headset, such as headset 100, by a connecting member 236 and may be electrically coupled to the headset electrical circuit by conductive wire 238. Electrode base 234 may be configured to include at least one electrode base housing 240 which includes elevated circumferential walls surrounding a floor 242, thereby creating a cavity adapted to receive disposable electrode unit 232. According to certain embodiment, electrode base housing 240 is preferably made of a flexible material such as silicon or thermoplastic polyurethane (TPU).

Electrode base housing 240 may be configured to include an electrically conductive material defining a contact portion 244 disposed at least partially above, or within the floor 242 of electrode base housing 240. The conductive layer is adapted to be electrically coupled to an electric circuit by conductive wire 238 and may function as a contact point for the disposable electrode unit 232.

Electrode unit 232 may be configured to be releasably coupled (physically and electrically) to electrode base housing 240.

The electrode unit 232 is a multi-layer unit, which may include liquid absorbent layer, or pad, 246, and a flexible electrically conductive backing layer 248, preferably made of a carbon foil. The two layers may be attached or directly attached. Various manufacturing processes may be used, including heat welding, RF welding, ultrasonic welding, gluing or sewing. In some embodiments, in order to reduce current density at the edges of liquid absorbing layer 246, conductive backing layer 248 may be configured to have a smaller area or "footprint" than layer 246. Consequently, the current density at the edges of layer 246 (which has a lower electrical conductivity with respect to layer 248) will be reduced.

Conductive backing layer 248 may further include a thin electrically conductive layer 250 of conductive paint, which may be printed in a "mesh" pattern and may be configured to cover only the central portion of layer 248. Conductive paint layer 250 may preferably be printed on the bottom surface of layer 248 and may be configured to face contact portion 244 of electrode base housing 240 so as to be electrically coupled when multi-layered electrode unit 232 is attached to electrode base housing 240. Conductive paint layer 250 may be configured to have a higher electrical conductivity compared to layer 248, such that current dispersion over layer 248 is improved while reducing current density at the edges of layer 248.

In some embodiments, the disposable electrode unit 232, including pad 246, may be provided to the user dry, and the user may soak pad 246 with water, saline, conductive gel, or other suitable liquid before use. In other embodiments, the electrode pad 246 of disposable electrode unit 232 may be pre-soaked with conductive gel, such that the gel is mostly absorbed in the pad, and the user need not soak the pad at all. The conductive gel may be any commercially available conductive gel suitable for use with electrodes. It is appreciated that use of conductive gel improves conductivity and reduces dehydration of the pad 246, and that pre-soaked pads 246 may be easier and less messy for the user to handle. In some embodiments, the pad 246 may comprise a self-adhesive hydrogel layer.

Electrode pad 246 of disposable electrode unit 232 may be configured to receive (sense) electrical current or other bio-signals from the skin surface, such as for example electroencephalogram (EEG) and either transfer it via the headset circuit to an electronic circuit that includes a microprocessor or transmit it wirelessly to a remote unit.

As mentioned above, electrode unit 232 may be disposable and may be conveniently replaced by the user.

Electrode unit 232, and particularly electrode pad 246, may be configured to include a peripheral edge 256 that is thinner than the central area of pad 246. Peripheral edge 256 can be made by various manufacturing process such as ultrasonic welding, RF welding or heat compression. By inserting the thin edge 256 into a corresponding groove 252 in housing 240, electrode pad 246 can be reversibly physically coupled to housing 240 and electrically coupled to contact portion 244.

Electrode unit 232 may be configured to have larger area compared to housing 240. It can therefore be squeezed into housing 240 in order to be reversibly (physically an electrically) coupled to housing 240.

Electrode base housing 240 may be configured to include a conducting mechanical snap connector configured to be both physically and electrically reversibly coupled to a corresponding connector attached to electrode unit 232.

Perspective views of an electrode base 234 with and without an inventive, multi-layered disposable electrode unit 232 are provided in FIG. 6B and FIG. 6C.

Additional Electrode configurations are described in PCT Application Publication Number WO2014/141213, entitled "HEADSET FOR TREATMENT AND ASSESSMENT OF MEDICAL CONDITIONS", which is hereby incorporated by reference as if fully set forth herein.

Figure 7A:
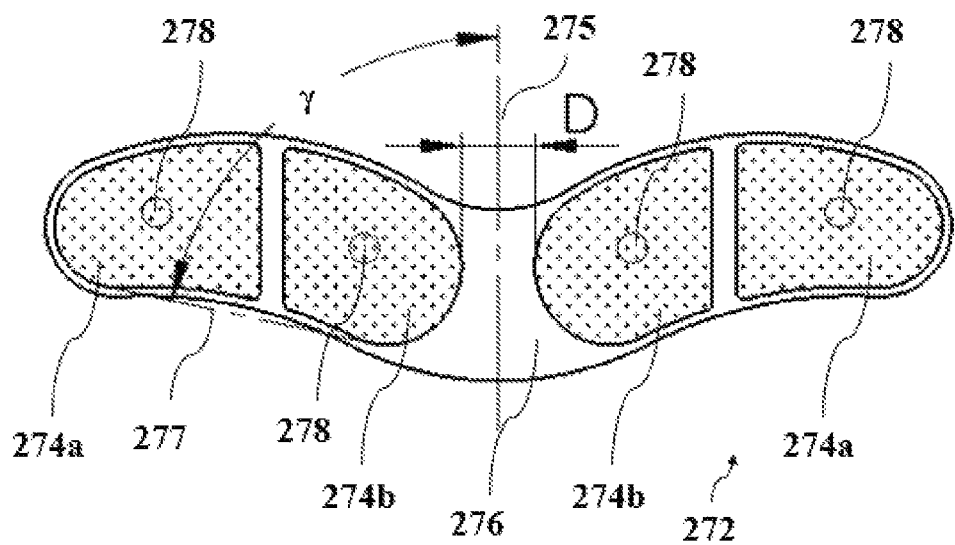
FIG. 7A is a planar top view illustration of a disposable electrode unit including multiple electrodes mounted on a single electrode substrate.
Figure 7B:
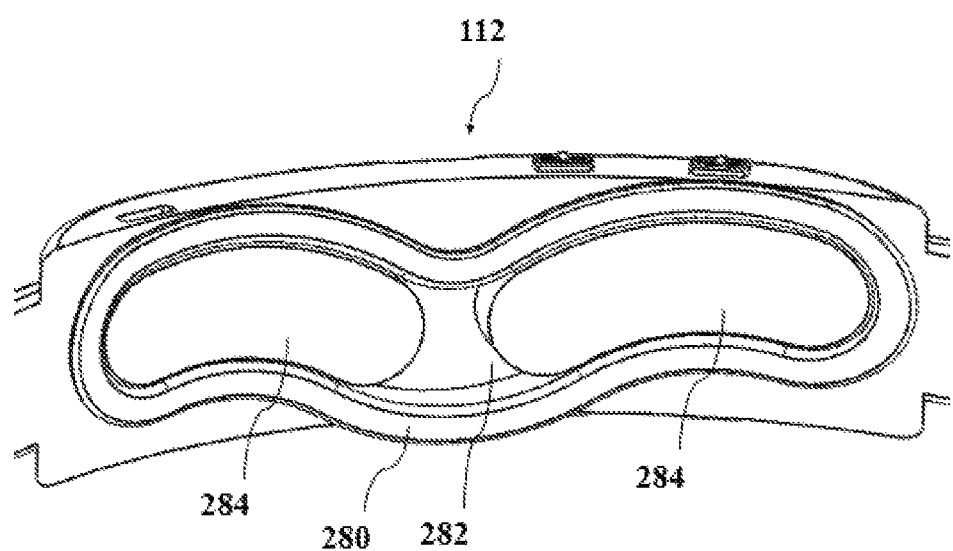
FIG. 7B is a perspective view illustration of an electrode receiving unit suitable for use in the inventive headset of FIGS. 1A and 1B, including a single electrode base housing a single disposable electrode unit including a plurality of electrodes.

Reference is now made to FIG. 7A, which is a planar top view illustration of a disposable electrode unit including multiple electrodes mounted on a single electrode substrate, and to FIG. 7B, which is a perspective view illustration of an electrode receiving unit suitable for use in the inventive headset of FIGS. 1A and 1B, including a single electrode base housing a single disposable electrode unit including a plurality of electrodes.

As seen in FIG. 7A, a disposable electrode unit 272 includes two pairs of electrode pads 274a and 274b, which may be similar to electrode pads 246 and electrode backing 248 of FIGS. 6A to 6C, mounted onto a single non-conductive electrode substrate 276. Each of the electrode pads 274 has a dedicated electrical contact 278 associated therewith, which electrical contact facilitates electrical connection between the electrode pad 274 and a conductive portion of an electrode base (not shown) into which the disposable electrode unit 272 is inserted. As seen, in some embodiments, the two pairs of electrodes 274a and 274b are mirror image symmetrical.

In some embodiments, the dimensions and spatial relationship of electrode pads 274a and 274b are substantially as described hereinbelow with reference to FIGS. 10B to 10D.

An angle γ characterizes the angular placement of the electrode pair 274a, 274b relative to an axis of symmetry of the disposable electrode unit 272, indicated by reference numeral 275. Angle γ is defined between a line connecting two boundary points of the contour 277 at the base of the electrode pair 274a, 274b, similar to line K of FIG. 10B, and the axis of symmetry 275, and, in some embodiments, is not greater than 90 degrees, not greater than 80 degrees, or not greater than 70 degrees.

As mentioned hereinabove, the distance D between the two pairs of electrodes 274a, 274b, may be in a range of 4-35 mm, 6-25 mm, or 8-15 mm.

It is appreciated that mounting of multiple electrode pads on a single electrode substrate ensures that the relative distances and angular relationships between the electrodes are maintained, even if the electrodes need to be squeezed into the electrode base, for example as described hereinabove with reference to FIGS. 6A to 6C. Furthermore, multiple electrodes on a single structure allow the user to have to manage fewer disposable items, and increase the ease of use of the electrodes and the headset.

Figure 10A:
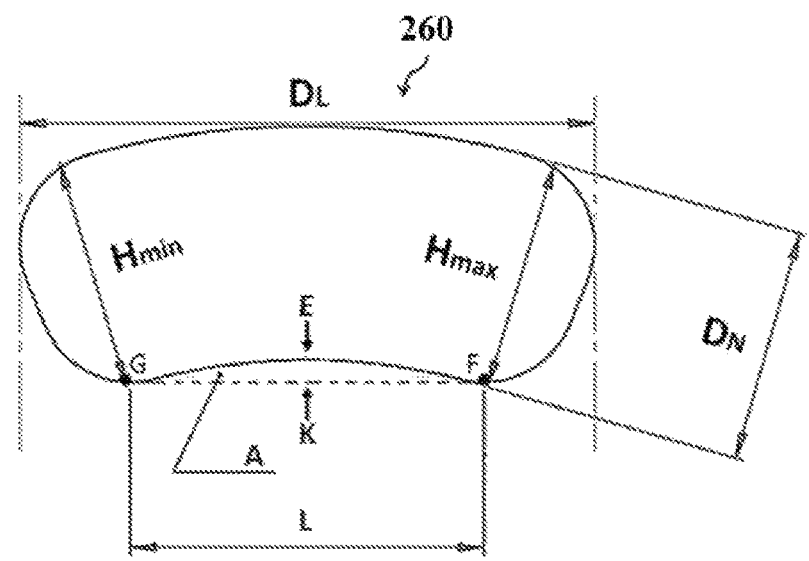
FIG. 10A is a schematic illustration of the dimensions of a singular inventive electrode configured to selectively stimulate nerve branches in the supraorbital region.
Figure 10B:
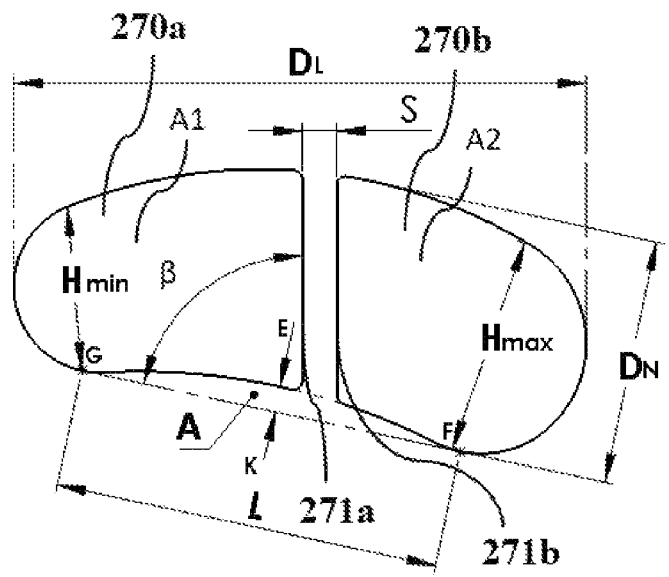
FIGS. 10B and 10C are schematic illustrations of the dimensions of two embodiments of split inventive electrodes, configured to selectively stimulate nerve branches in the supraorbital region.
Figure 10C:
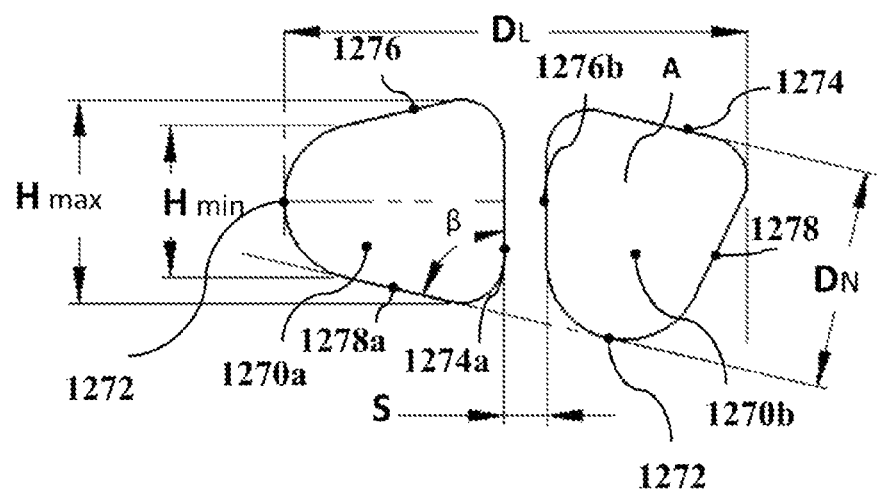

Though the electrode unit 272 shown in FIG. 7A includes two pairs of electrodes, a structure may be used for mounting a single pair of electrodes for unilateral stimulation of the trigeminal nerve branches at either the left or right side of the forehead, similar to the structure shown in FIGS. 10B and 10C. In other embodiments, two electrodes may be used, each comprising a single electrode and having dimensions and spatial relationships similar to the embodiment shown in FIG. 10A.

Reference is now made to FIG. 7B, which is a perspective view illustration of an electrode receiving unit suitable for use in the inventive headset of FIGS. 1A and 1B, including a single electrode base housing a single disposable electrode unit including a plurality of electrodes.

As seen in FIG. 7B, an anterior member 112, similar to that described hereinabove with reference to FIGS. 1A and 1B, includes a single electrode housing 280, which may be similar to electrode housing 240 described hereinabove with reference to FIGS. 6A to 6C. The electrode housing 280 is configured to span a large portion of the user's forehead when the headset is donned, and to receive therein a disposable electrode unit 282 including a plurality of electrode pads 284, and to provide a seal around all of electrode pads 284.

In the illustrated embodiment, the electrode unit 282 includes a single substrate and a pair of electrode pads 284, adapted to stimulate trigeminal nerves in the supraorbital region of the user's head. However, in some embodiments, the electrode unit 282 may include more than two electrodes, for example similar to electrode unit 272 described hereinabove with reference to FIG. 7A.

In some embodiments, the single electrode housing 280 may receive one or more disposable electrode units, each including one or more electrode pads, and need not necessarily receive only an electrode unit perfectly suited to the contours of housing 280.

Figure 9A:
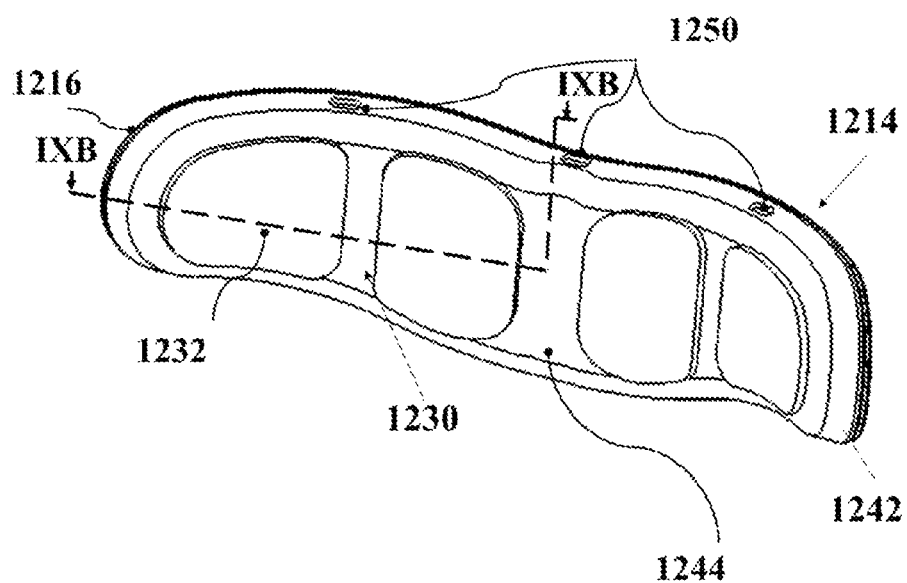
FIG. 9A is a perspective view illustration of an inventive electrode unit according to another embodiment of the teachings herein, the electrode unit forming part of the inventive anterior member of FIGS. 8A and 8B, the electrode unit including multiple electrodes mounted on a flexible leaf.
Figure 9B:
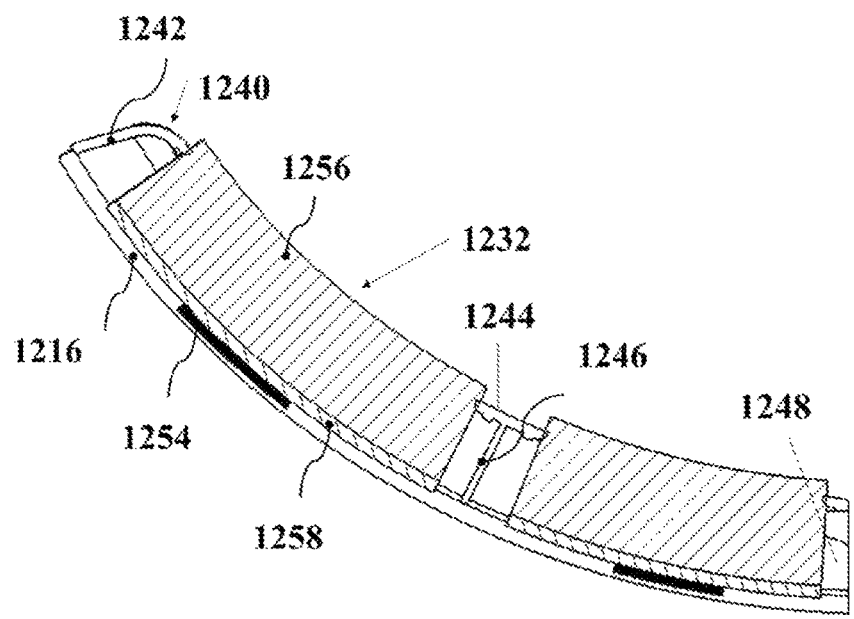
FIG. 9B is a sectional illustration of the inventive electrode unit of FIG. 9A, the sectional illustration taken along section lines IXB-IXB in FIG. 9A.

Reference is now made to FIGS. 8A and 8B, which are planar top view illustrations of an inventive anterior member suitable for use with the inventive headset of FIGS. 1A and 1B according to another embodiment of the teachings herein, in a rest state and a donned state respectively, to FIG. 9A which is a perspective view illustration of an inventive electrode unit according to another embodiment of the teachings herein, the electrode unit forming part of the inventive anterior member of FIGS. 8A and 8B, the electrode unit including multiple electrodes mounted on a single flexible leaf, and to FIG. 9B which is a sectional illustration of the inventive electrode unit of FIG. 9A, the sectional illustration taken along section lines IXB-IXB in FIG. 9A.

As seen in FIGS. 8A and 8B, in some embodiments anterior member 112 includes a flexible portion 1214, here shown as a flexible leaf 1216 having mounted thereon the anterior electrode systems. In the rest state, or when the headset is not donned by the user and pressed against his forehead, the flexible portion extends radially inward from anterior member 112, and has a first radius indicated in FIG. 8A by R and a first radial depth, indicated in FIG. 8A by reference A. When the headset is donned by the user, the flexible portion 1214 is extended radially outwardly, and has a radius indicated in FIG. 8B by R' and a second radial depth, indicated in FIG. 8B by A'. The second radius R' is greater than the first radius R, and the second radial depth A' is smaller than the first radial depth A, such that the flexible portion 1214 conforms in shape to the contour of the user's forehead and applies pressure thereto, thereby ensuring that sufficient pressure is present between the headset 100 and the user's head in variable conditions, such that the headset, and treating components thereof, would not move from their intended location during use of the headset even if the user changes his or her position, for example lies down applying pressure to the posterior area of the headset or to a side portion of the headset. Additionally, the flexibility of flexible portion 1214 and the pressure applied thereby when it is extended radially outwardly compensates for differences between the contour of the anterior member 112 and variable forehead contours, such that electrode systems 130 contact the user's forehead regardless of the exact anatomical structure of the user's forehead.

In some embodiments, the degree to which the flexible portion 1214 is extended when the headset 100 is donned, contributes to adjustment of the circumference of headset 100.

It is appreciated that there are many ways to construct a suitable flexible portion 1214, one of which is described hereinbelow with reference to FIGS. 9A and 9B.

It is further appreciated that a flexible portion 1214 according to the teachings herein need not necessarily form part of the anterior member 112, and may be removably connectable thereto, for example using a snap fit connection, or may be placed in any location on the headset which is adapted to engage the user's skin, such as in posterior members 116 and/or along arm member 114.

Turning now to FIGS. 9A and 9B, it is seen that an electrode system 1230 is mounted onto flexible leaf 1216. The electrode system 1230 includes one or more electrode units 1232 for which leaf 1216 functions as an electrode base. Leaf 1216 is configured to be physically coupled to the anterior member 112 of a headset, such as headset 100, by a connecting member (not shown) and may be electrically coupled to the headset electrical circuit by conductive wire (not shown) or conductive connector. Electrode units 1232 are surrounded by at least one electrode housing 1240.

Electrode housing 1240 includes side walls 1242 arranged about the circumference of leaf 1216, and an anterior wall portion 1244 arranged at an anterior portion of the electrode system 1230 and adapted to engage the skin of the user, when the electrode system is in use, as seen in FIG. 8B. Intermediate wall portions 1246 separate between electrode units 1232, such that the leaf 1216 together with electrode housing 1240 creates cavities 1248 adapted to receive the electrode units 1232. According to certain embodiment, electrode housing 1240 is preferably made of a flexible material such as silicon or thermoplastic polyurethane (TPU).

The electrode housing 1240, and specifically the cavities 1248, are adapted to retain fluid released from electrode units 1232 when the leaf 1216 is extended and the electrode system 1230 is compressed against the user's forehead, as shown in FIG. 8B. In some embodiments, side walls 1242 include one or more air vents 1250, adapted to allow removal of air from cavities 1248 when the electrode system 1230 is compressed against the user's forehead or when fluid is released from electrode units 1232 into cavities 1248.

Flexible leaf 1216 may include an electrically conductive material defining a contact portion 1254 disposed at least partially above, or within the leaf 1216. The conductive layer is adapted to be electrically coupled to an electric circuit by the conductive wire (not shown) and may function as a contact point for the electrode unit 1232.

Electrode unit 1232 may be configured to be releasably coupled (physically and electrically) to leaf 1216 within electrode housing 1240.

The electrode unit 1232 is a multi-layer unit, which may include liquid absorbent layer, or pad, 1256, and a flexible electrically conductive backing layer 1258, preferably made of a carbon foil, substantially as described hereinabove with reference to FIGS. 6A to 6C. Conductive backing layer 1258 may further include a thin electrically conductive layer of conductive paint substantially as described hereinabove with reference to FIGS. 6A to 6C

In some embodiments, the electrode unit 1232 is disposable, and together with pad 1256, may be provided to the user dry, and the user may soak pad 1256 with water, saline, conductive gel, or other suitable liquid before use. In other embodiments, the electrode pad 1256 of disposable electrode unit 1232 may be pre-soaked with conductive gel, such that the gel is mostly absorbed in the pad, and the user need not soak the pad at all. The conductive gel may be any commercially available conductive gel suitable for use with electrodes. It is appreciated that use of conductive gel improves conductivity and reduces dehydration of the pad 1256, and that pre-soaked pads 1256 may be easier and less messy for the user to handle. In some embodiments, the pad 1256 may comprise a self-adhesive hydrogel layer.

Electrode pad 1256 of electrode unit 1232 may be configured to receive (sense) electrical current or other biosignals from the skin surface, such as for example electroencephalogram (EEG) and either transfer it via the headset circuit to an electronic circuit that includes a microprocessor or transmit it wirelessly to a remote unit.

As mentioned above, in some embodiments, electrode unit 1232 may be disposable and may be conveniently replaced by the user. In some embodiment the contact portion 1254 and/or the backing layer 1258 may be fixed to leaf 1216, whereas in other embodiments one or both of these layers may be attached to pad 1256 and may be replaced therewith by the user. In some such embodiments, leaf 1216 may be configured to include a conducting mechanical snap connector configured to be both physically and electrically reversibly coupled to a corresponding connector attached to electrode unit 1232.

In some embodiments, the electrode units 1232 are permanently attached to electrode housing 1240, and the electrode units 1232 together with housing 1240 are disposable and designed to be replaced by the user after each use or after several uses. In some embodiments, the entire flexible portion 1214, including the leaf 1216 and the electrode system 1230 are disposable, and are designed to be replaced by the user after each use.

Figure 10D:
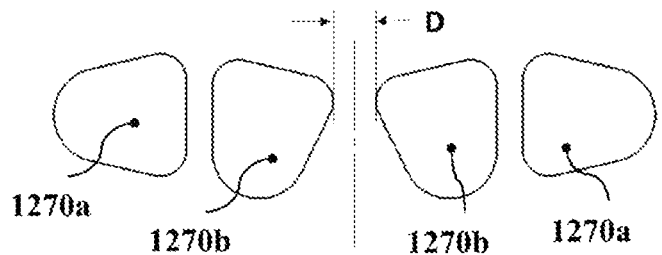
FIG. 10D is a schematic illustration of the arrangement of the electrodes of FIG. 10C, when stimulating nerve branches on both the right and left sides of the supraorbital region.

Reference is now made to FIG. 10A, which is a schematic illustration of the dimensions of a singular inventive electrode configured to selectively stimulate nerve branches in the supraorbital region, to FIGS. 10B and 10C which are schematic illustrations of the dimensions of two embodiments of split inventive electrodes, configured to selectively stimulate nerve branches in the supraorbital region, and to FIG. 10D which is a schematic illustration of the arrangement of the electrodes of FIG. 10C, when stimulating nerve branches on both the right and left sides of the supraorbital region.

FIG. 10A is an illustration of an embodiment of an electrode 260, which may be configured for stimulation of the supraorbital region, such as one or more of electrode systems 130 of FIGS. 1A and 1B. Electrode 260 may include a liquid-absorbent layer having a biocompatible contact surface, the contact surface adapted to be juxtaposed against the skin surface of the user, and an electrode backing attached to the liquid-absorbent layer, the backing containing at least one electrically conductive material or element, the conductive material or element being electrically connected, in an operational mode, with the liquid-absorbent layer, when the liquid-absorbent layer is filled with liquid.

Electrode 260 may be configured to have a conductive contact surface with the following dimensions:
(i) a long dimension ($D_L$) having a length of 20 mm to 55 mm, 25 to 50 mm, or 30 to 45 mm.
(ii) a narrow dimension ($D_N$) having a length of 10 mm to 30 mm, 10 to 25, or 12 to 20 mm.

Concave contour E has a concavity defined by boundary points G and F, which points are disposed at opposite ends of the concavity.

Typically, A/L is at least 0.5 mm,
A being an area bounded by dotted line K and the concavity; L being a length of line K (between boundary points G and F), (L) being at least 10 mm, wherein a line disposed between a first point on the concave contour and a second point on the perimeter of electrode 260, on a side opposite to concave contour E, and aligned in perpendicular fashion with respect to contour E at the first point, has a length H, and wherein, over an entirety of the concave contour, $$H_{max}/H_{min} \leq 2.5$$

$H_{max}$ being a maximum value of H over this entirety; and $H_{min}$ being a minimum value of H over this entirety.

The distance between two electrodes 260 configured to stimulate the supraorbital region may be in a range of 4-35 mm, 6-25 mm, or 8-15 mm.

FIG. 10B is an illustration of an embodiment of a pair of electrodes 270a and 270b, which may be configured for stimulation of the anterior portion of the user's head, such as for stimulation of a specific nerve or nerve branches in the supraorbital region or for transcranial stimulation of the anterior region of the user's brain, such that in some embodiments, electrodes 270a and 270b, together, may be similar in functionality to one or more of electrode systems 130 of FIGS. 1A and 1B.

Each of electrode 270a and 270b may include a liquid-absorbent layer having a biocompatible contact surface, the contact surface adapted to be juxtaposed against the skin surface of the user, and an electrode backing, attached to the liquid-absorbent layer, the backing containing at least one electrically conductive material or element, the conductive material or element being electrically connected, in an operational mode, with the liquid-absorbent layer, when the liquid-absorbent layer is filled with liquid.

In some embodiments, in addition to the existing layers, electrodes 270a and 270b also share an additional non-conductive electrode substrate, the substrate including two contact portions each in electrical contact with the electrode backing of one of electrodes 270a and 270b, substantially as described hereinabove with reference to FIG. 7A.

Electrodes 270a and 270b each have a first end, a second end, a height, and a length, such that the heights of electrodes 270a and 270b, at a maximal point thereof ($D_N$), are in the range of 10 mm to 40 mm, 12 mm to 36 mm, or 20 to 33 mm.

The electrodes 270a and 270b are configured to be arranged, when disposed adjacent the user's skin, horizontally alongside one another, such that a second end 271a of the first electrode is adjacent, and in some embodiments parallel to, a first end 271b of the second electrode with a distance S therebetween, S being in the range of 1-15 mm, 2-10 mm, or 4-8 mm.

A length ($D_L$) consisting of the length of electrode 270a, the length of electrode 270b, and distance S, is in the range of 20 mm to 55 mm, 25 to 50 mm, or 30 to 45 mm. In some embodiments, the area $A_1$ of electrode 270a is equal to the area $A_2$ of electrode 270b. In other embodiments, the ratio of the areas $A_1/A_2$ is in the range of 0.5-2, 0.7-1.5, or 0.8-1.25.

In some embodiments, electrodes 270a and 270b, together, may be defined at a lower end thereof along a single concave contour E having a concavity defined by boundary points F and G, which points are disposed at opposite ends of the concavity, the concavity generally following the outline of the user's eyebrows, such that:

a ratio A/L is at least 0.5 mm, where A is an area bounded by dotted line K and the concavity and L is a length of line K (between boundary points G and F), L being at least 10 mm.

As discussed hereinabove, a line disposed between a first point on the concave contour and a second point on the perimeter of one of electrodes 270a or 270b, on a side opposite to concave contour E, and aligned in perpendicular fashion with respect to contour E at the first point, has a length H, and wherein, over an entirety of the concave contour of both electrodes 270a and 270b, $$H_{max}/H_{min} \leq 2.5$$

$H_{max}$ being a maximum value of H over this entirety; and $H_{min}$ being a minimum value of H over this entirety.

An angle β, defined between edge 271a of electrode 270a and line K, is in the range of 45-110 degrees, 70-90 degrees, or 75-85 degrees. β characterizes the angle of edge 271a relative to the base of the electrode.

It is appreciated that in some embodiments, electrodes 270a and 270b, taken together, may suitable for use in a single anterior electrode system 130 as shown in FIGS. 1A and 1B. Additionally, in embodiments in which the pair of electrodes 270a and 270b are asymmetrical, as a pair, a corresponding pair of electrodes to be used on the symmetrically opposed side of the user's forehead, would be a mirror image replica of electrodes 270a and 270b.

The distance between two pairs of electrodes 270a and 270b configured to stimulate the supraorbital region may be in a range of 4-35 mm, 6-25 mm, or 8-15 mm.

FIG. 10C is an illustration of an embodiment of a pair of electrodes 1270a and 1270b, which may be configured for stimulation of the anterior portion of the user's head, such as for stimulation of a specific nerve or nerve branch in the supraorbital region. Specifically, the electrodes may be configured for stimulation of the supraorbital and supratrochlear nerves, which are branches of the ophthalmic division of the trigeminal nerve, as illustrated hereinbelow with reference to FIG. 23C. In some embodiments, electrodes 1270a and 1270b, together, may be similar in functionality to one or more of electrode systems 130 of FIGS. 1A and 1B.

Each of electrodes 1270a and 1270b may include a liquid-absorbent layer having a biocompatible contact surface, the contact surface adapted to be juxtaposed against the skin surface of the user, and an electrode backing, attached to the liquid-absorbent layer, the backing containing at least one electrically conductive material or element, the conductive material or element being electrically connected, in an operational mode, with the liquid-absorbent layer, when the liquid-absorbent layer is filled with liquid.

In some embodiments, in addition to the existing layers, electrodes 1270a and 1270b also share an additional non-conductive electrode substrate, the substrate including two contact portions each in electrical contact with the electrode backing of one of electrodes 1270a and 1270b, substantially as described hereinabove with reference to FIG. 7A.

In some embodiments, electrodes 1270a and 1270b have a substantially identical contour, and are merely rotated relative to one another to form the general contour shown in FIG. 10C. The identical shape and size of the electrodes simplifies the placement of the electrodes by the user, and simplifies and reduces manufacturing costs. Although the electrodes have the same contour, they are disposed in different angular orientations so as to be accurately placed above the anatomical position of each of the stimulated nerve branches and to prevent undesired stimulation of tissues, such as the skull periosteum, which would be unpleasant for the user.

The electrodes 1270a and 1270b are generally trapezoidal, where corners of the trapezoid are replaced by curves. As such, each electrode includes a first end or base 1272, a second end or base 1274, a first side 1276, and a second side 1278, a height (defined between the first and second sides), and a length (defined between the first and second bases).

The length of electrodes 1270a and 1270b, at a maximal point thereof ($D_N$), is in the range of 10 mm to 40 mm, 15 mm to 30 mm, or 20 to 25 mm. The height of the electrodes 1270a and 1270b is such that a minimal height $H_{min}$ defined between the first and second sides adjacent the first base, and a maximal height $H_{max}$ defined between the first and second sides adjacent the second base, fulfill the formula $$H_{max}/H_{min} \leq 2.$$

The electrodes 1270a and 1270b are configured to be arranged, when disposed adjacent the user's skin, horizontally alongside one another, such that a second base 1274a of the first electrode is adjacent, and in some embodiments parallel to, a first side 1276b of the second electrode with a distance S therebetween, S being in the range of 1-15 mm, 2-10 mm, or 4-8 mm. The parallel arrangement of second base 1274a and first side 1276b prevents the formation of areas of increased current density between the electrodes.

A length ($D_L$) consisting of the length of electrode 1270a, a width of electrode 1270b, and distance S, is in the range of 20 mm to 55 mm, 25 to 50 mm, or 30 to 45 mm. In some embodiments, the area A of electrodes 1270a and 1270b are equal.

An angle β, defined between second base 1274a and second side 1278a of electrode 1270a, is in the range of 45-110 degrees, 70-90 degrees, or 75-85 degrees. β characterizes the angle of second side 1278a relative to the base 1274a of the electrode. It is appreciated that electrodes 1270a and 1270b may be side to side symmetrical, such that also β characterizes the angle of first side 1276a relative to the base 1274a of the electrode.

It is appreciated that in some embodiments, electrodes 1270a and 1270b, taken together, may suitable for use in a single anterior electrode system 130 as shown in FIGS. 1A and 1B. Additionally, two pairs of electrodes 1270a and 1270b, arranged as a mirror image of one another, may be used on the symmetrically opposed side of the user's forehead, as illustrated in FIG. 10D. In some embodiments, each pair of electrodes 1270a and 1270b is configured to function as a separate stimulation channel, stimulating a branch of the supraorbital nerve and a corresponding branch of the supratrochlear nerve.

The distance D between two pairs of electrodes 1270a and 1270b configured to stimulate the supraorbital region may be in a range of 4-35 mm, 5-25 mm, or 6-15 mm.

Additional electrodes may be located on the headset in order to stimulate other nerves, for example, the zygomaticotemporal nerve or the auriculotemporal nerve at the sides of the head or to stimulate the temporal brain region. The headset may also include electrodes that are configured to stimulate the occiput region, as described further hereinbelow with reference to FIGS. 22A to 22B.

Figure 11A:
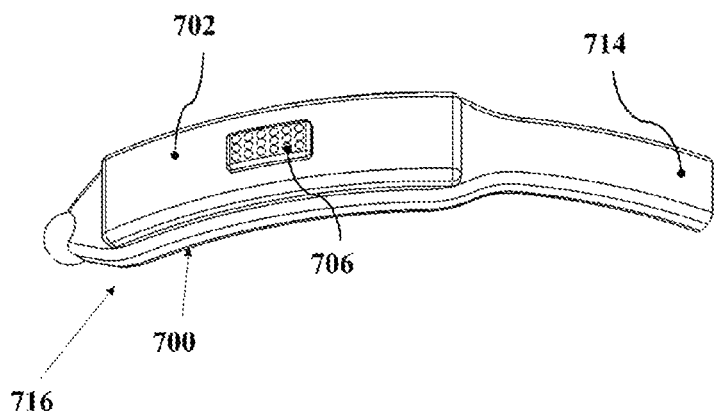
FIGS. 11A and 11B are perspective view illustrations of an embodiment of an inventive posterior member suitable for use with the inventive headset of FIGS. 1A and 1B.
Figure 11B:
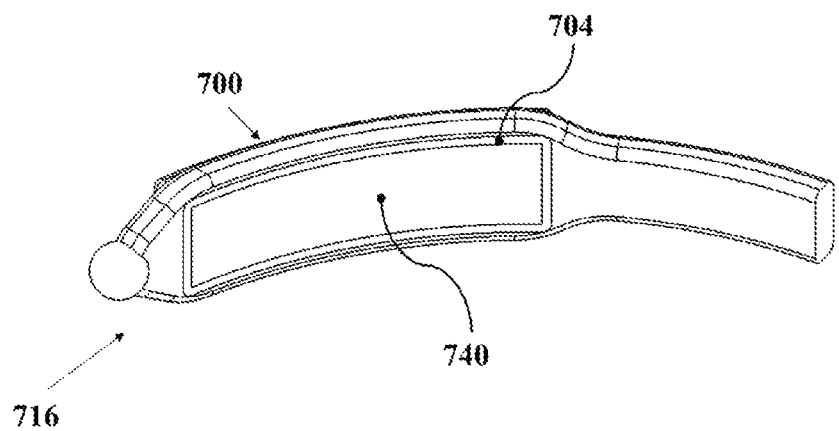
Figure 12A:
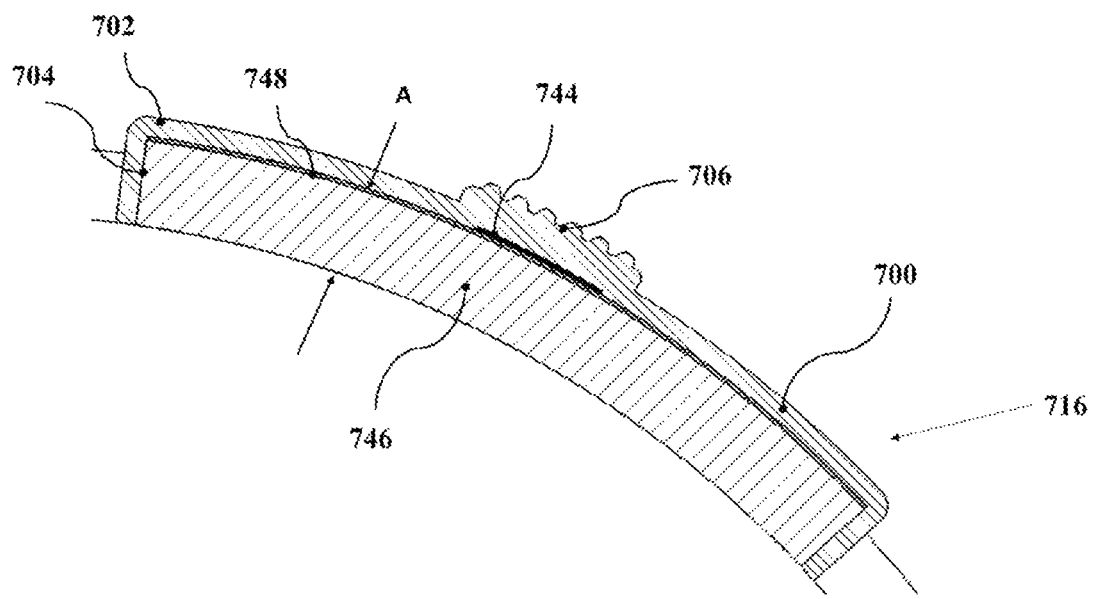
FIGS. 12A and 12B are schematic sectional illustrations of the posterior member of FIGS. 11A and 11B in a rest state and in a pressed state, respectively.
Figure 12B:
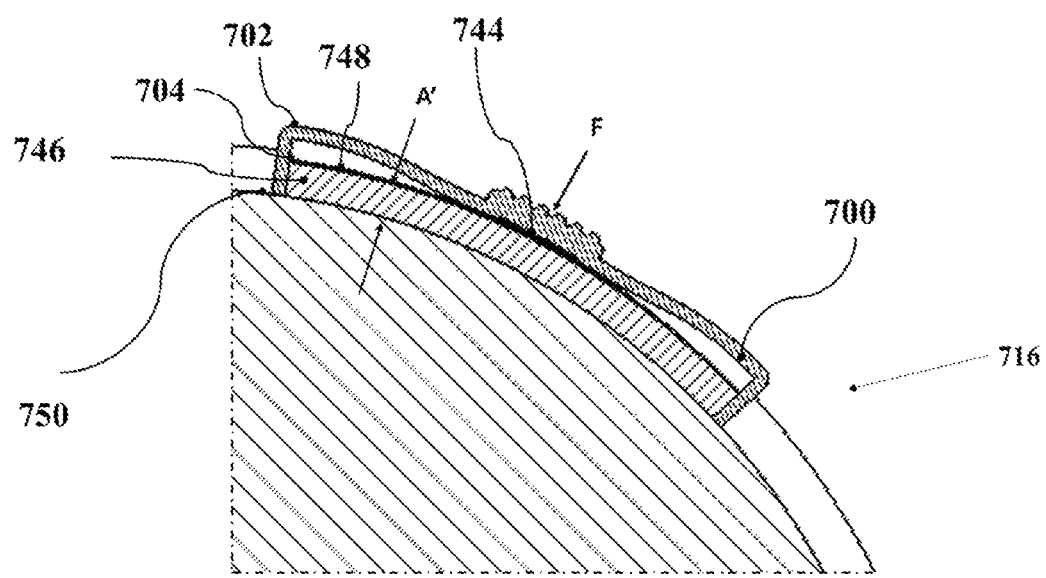

Reference is now made to FIGS. 11A and 11B, which are perspective view illustrations of an embodiment of an inventive posterior member suitable for use with the inventive headset 100 of FIGS. 1A and 1B, and to FIGS. 12A and 12B, which are schematic sectional illustrations of the posterior member of FIGS. 11A and 11B in a rest state and in a pressed state, respectively.

As seen in FIGS. 11A and 11B, a posterior member 716, which may be similar to posterior member 116 of FIGS. 1A and 1B, includes a posterior electrode housing 700 having adapted to house an occipital electrode system 740, similar to electrode systems 140 of FIGS. 1A and 1B. Posterior electrode housing 700 includes an outer surface 702 configured, when the headset is in use by a user, to face away from the skin of the user, and an inner surface 704, configured to engage the skin of the user when the headset is in use. In some embodiments, the electrode housing 700 is formed of a flexible material, such as a silicone rubber, polyurethane, polypropylene, and the like.

Electrode system 740 typically includes an electrode pad 746, which is adapted to electrically engage, a conductive backing layer 748, substantially as described hereinabove with reference to FIGS. 6A to 6C. The conductive backing layer 748 may be disposed within said posterior electrode housing 700, in some embodiments mounted onto inner surface 704, and is configured to electrically engage an electrical contact 744 disposed in or on the inner surface 704 of posterior electrode housing 700. Typically, the electrode pad 746 is disposable, and may be replaced by the user for each use or as necessary. In some embodiments, the conductive backing layer 748 is mounted onto the disposable electrode pad 746, and is replaced by the user when the electrode pad is replaced.

Disposed on outer surface 702, typically at a location parallel to the location of contact 744 on inner surface 704, is a pressure location guide 706 configured to guide a user wearing the headset as to a suitable location for applying pressure to the posterior electrode. In some embodiments, the pressure location guide 706 is textured, such that the user can tactilely feel its location at the posterior portion of the user's head when the headset is donned.

When the headset is in its rest state, or is not donned by the user, the electrode system 740 engages the entire inner surface 704 of the electrode housing 700, as illustrated in FIG. 12A. In this state, the electrode pad 746 has a first thickness indicated by A.

Following donning of the headset as described hereinabove, when the electrode system 740 is placed beneath the hair of the user at the posterior of the user's head, the user applies pressure to the electrode housing 700 at the location indicated by pressure location guide 706, in a direction indicated by arrow F in FIG. 12B. In some embodiments, the force F applied by the user is greater than 0.1 N, greater than 1.0 N, or greater than 3.0 N.

Due to the flexible nature of the electrode housing 700, pressure applied by the user at pressure location guide 706 results in deformation of the electrode housing 700 and in compression of the electrode pad 746 to a thickness of A', as seen in FIG. 12B. In some embodiments, the thickness A' of the electrode pad 746 in the pressed state is smaller than the thickness A of the pad in the rest state (A'<A).

The pressure applied by the user, together with the compression of the electrode pad 746, results in release of a conductive fluid, such as a water, saline, or conductive gel, from the electrode pad 746 into a gap between the electrode system 740 and the hair and/or scalp of the user. The released liquid reduces the impedance between the electrode system 740 and the scalp, which is caused by the presence of hair therebetween, and thus improves the efficacy of the treatment.

In some embodiments, the electrode housing 700 is not entirely formed of a flexible material, but rather include a layer formed of a flexible material, to which pressure is applied by the user.

In some embodiments, a rigid layer is disposed between the flexible electrode housing 700 or a flexible layer thereof and the electrode system 740. In such embodiments, pressure is applied by the user to the flexible electrode housing or to the flexible layer, and the pressure is distributed throughout the rigid layer resulting in the electrode backing 748, mounted onto the rigid layer, being in contact with an entire surface of the electrode pad 746. Additionally, more homogenous pressure may applied to the electrode pad 746. In such embodiments, the contact 744 and/or the electrode backing 748 is disposed on the rigid layer.

Figure 13A:
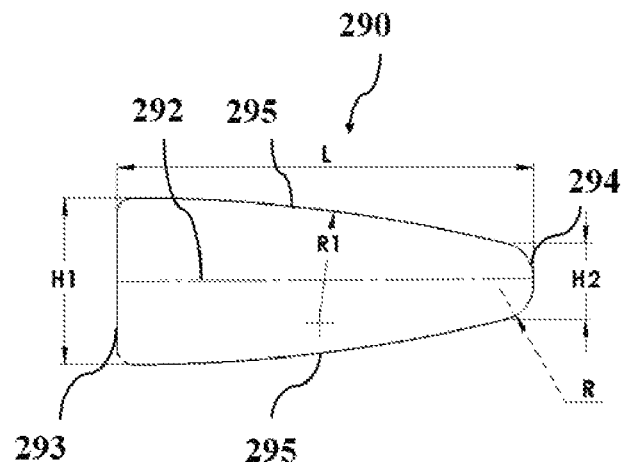
FIGS. 13A and 13B are schematic illustrations of the dimensions of a singular inventive electrode and of a split inventive electrode, both configured to selectively stimulate nerve branches in the occipital region.
Figure 13B:
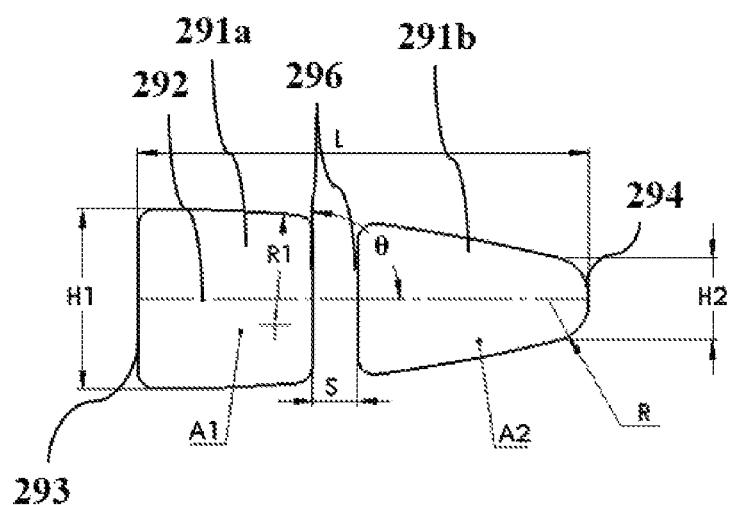

Reference is now made to FIGS. 13A and 13B, which are schematic illustrations of the dimensions of a singular inventive electrode and of a split inventive electrode, both configured to selectively stimulate nerve branches in the occipital region.

FIG. 13A is an illustration of an embodiment of an electrode 290 which may be configured for stimulation of the occipital region, such as one or more of electrode systems 140 of FIGS. 1A and 1B. FIG. 13B is an illustration of a pair of electrodes 291a and 291b, which together may have a similar outline to that of electrode 290, and which may be configured for stimulation of a specific nerve or nerve branches in the occipital region, such that electrodes 291a and 291b, together, may be similar in functionality to one or more of electrode systems 140 of FIGS. 1A and 1B.

Electrodes 290, 291a, and 291b may include a liquid-absorbent layer having a biocompatible contact surface, the contact surface adapted to be juxtaposed against the skin surface of the user, and an electrode backing, attached to the liquid-absorbent layer, the backing containing at least one electrically conductive material or element, the conductive material or element being electrically connected, in an operational mode, with the liquid-absorbent layer, when the liquid-absorbent layer is filled with liquid.

In some embodiments, electrodes 291a and 291b may both be attached to an additional, common non-conductive, electrode substrate layer the substrate including two contact portions each in electrical contact with the electrode backing of one of electrodes 291a and 291b.

Each of electrodes 290, 291a, and 291b is mirror-image symmetrical about a horizontal axis of symmetry 292.

Turning specifically to FIG. 13A, electrode 290 is narrow and elongated, and in some embodiments may have a tapered, curved, generally frusto-conical outline defining a first end 293 and a second end 294 which may be curved, connected by curves 295. In some embodiments, electrode 290 may be configured to have a conductive contact surface which may have the following dimensions:
(i) a long dimension (L) having a length of 10 mm to 55 mm, 15 mm to 50 mm, or 25 to 45 mm.
(ii) a narrow dimension ($H_1$) at base 293 having a length of 5 mm to 35 mm, 8 mm to 20 mm, or 10 mm to 15 mm.
(iii) a narrow dimension ($H_2$) at tip 294, such that a ratio between $H_1$ and $H_2$ is not greater than 2, not greater than 1.5, or not greater than 1.

In some embodiments, the curvature of curved tip 294 may be defined by an imaginary circle, partially circumscribed within curved tip 294, the imaginary circle having a radius R not greater than 10 mm, not greater than 8 mm, or not greater than 6 mm.

In some embodiments, the curvature of curves 295 may be defined by a second imaginary circle, partially circumscribed within each of curves 295, the imaginary circle having a radius $R_1$ of at least 50 mm, at least 100 mm, or at least 150 mm.

Turning to FIG. 13B, it is seen that electrodes 291a and 291b, taken together, have a similar outline to that of electrode 290. As such, electrode 291a may include base 293, electrode 291b may include tip 294, and imaginary curves 295 may extend from base 293 to tip 294, bridging the distance S between electrodes 291a and 291b.

The dimensions L, $H_1$, $H_2$, R, and $R_1$ shown in FIG. 13B are defined in substantially the same manner as the corresponding dimensions in FIG. 13A. Dimensions L, R, and $R_1$ of FIG. 13B are substantially the same lengths as the corresponding dimensions of FIG. 13A. However, dimension $H_1$ of FIG. 13B may have a length of 5 mm to 35 mm, 10 mm to 25 mm, or 12 mm to 20 mm. The ratio of dimensions $H_1$ and $H_2$ of FIG. 13B is substantially the same as the corresponding ratio of FIG. 13A.

As seen, the edges 296 of electrodes 291a and 291b which are adjacent one another may be parallel, and have a distance S therebetween, S being in the range of 1-10 mm, 2-8 mm, or 4-6 mm. It is appreciated that distance S may, in some embodiments, be selected to be suitable for each of electrodes 291a and 291b to stimulate a different one of the occipital nerve branches.

An angle θ, defined between edge 296 of electrode 291a and axis of symmetry 292, is in the range of 75-105 degrees, 80-100 degrees, or 85-95 degrees. The angle θ characterizes the angle at which the electrodes are split.

In some embodiments, the area $A_1$ of electrode 291a is equal to the area $A_2$ of electrode 291b. In other embodiments, the ratio of the areas $A_1/A_2$ is in the range of 0.5-2, 0.7-1.5, or 0.8-1.25.

It is appreciated that in some embodiments, electrodes 291a and 291b, taken together, may be suitable for use in a single posterior electrode system 140 as shown in FIGS. 1A and 1B. In some embodiments in which electrodes 291a and 291b are asymmetrical, as a pair, a corresponding pair of electrodes to be used on the opposed side of the user's occipital region, would be a mirror image replica of electrodes 291a and 291b.

Figure 14A:
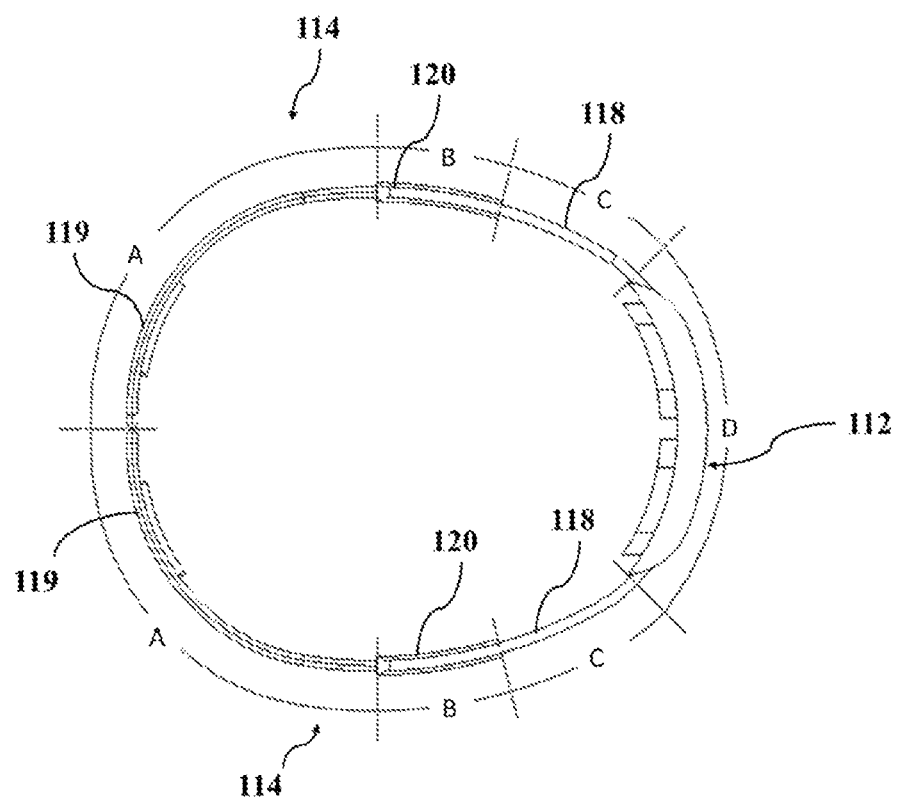
FIGS. 14A, 14B, and 14C are planar top view illustration of the headset of FIGS. 1A and 1B, demonstrating lengths of flexible arm members of the inventive headset.
Figure 14B:
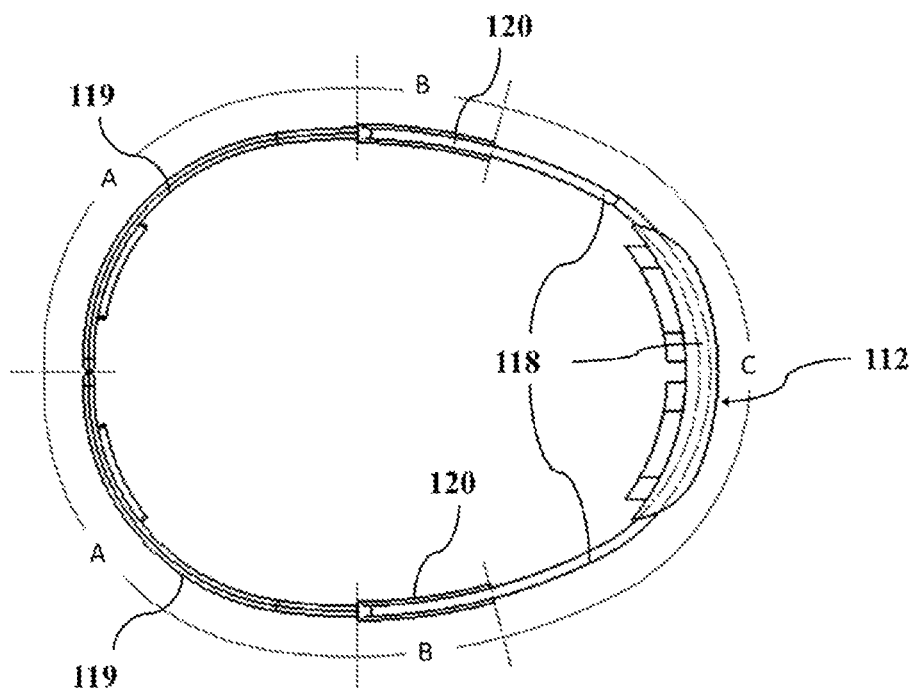
Figure 14C:
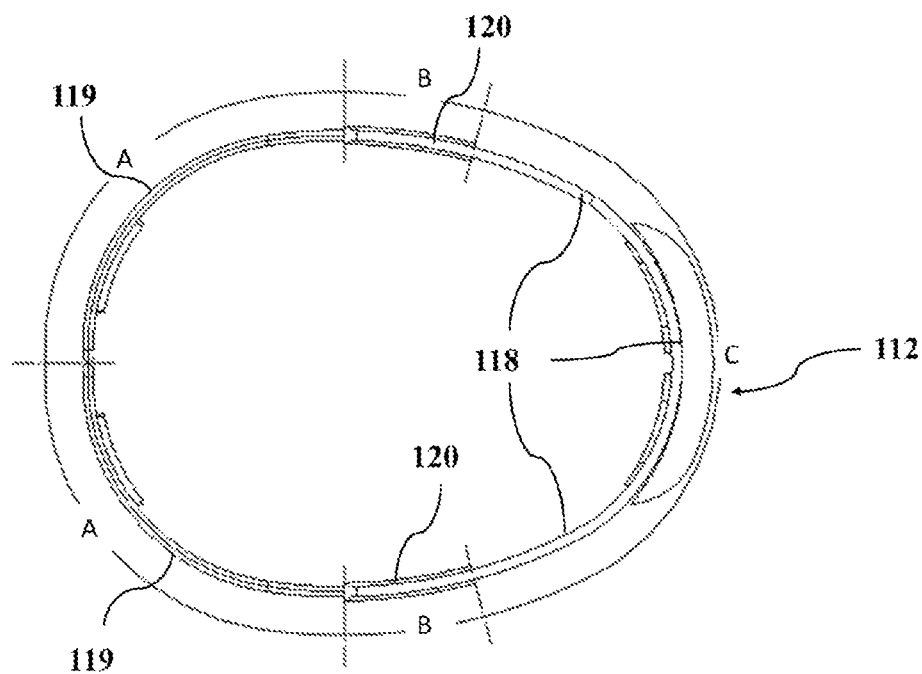

Reference is now made to FIGS. 14A, 14B, and 14C, which are planar illustrations of the inventive headset of FIGS. 1A and 1B, demonstrating lengths of flexible arm members 114 of the headset.

As mentioned hereinabove with reference to FIGS. 1A and 1B, each arm member 114 includes a flexible temple arm portion 118 adjacent the anterior member 112, a flexible posterior arm portion 119 including the posterior member 116, and a size adjustment mechanism 120 disposed therebetween.

Turning specifically to FIG. 14A, the length of flexible posterior arm portion 119, labeled by A, is smaller than 180 mm, 150 mm, or 130 mm. The length of the rigid adjustment mechanism 120, labeled by B, is smaller than 150 mm, 120 mm, or 100 mm. The length of temple arm portions 118, labeled by C, is smaller than 110 mm, 90 mm, or 75 mm. The length of anterior member 112, labeled by D, is smaller than 150 mm, 120 mm, or 100 mm.

In some embodiments, the dimensions A, B, C, and D are selected such that the total circumference of headset 100, which is given by the formula 2(A+B+C')+D is smaller than 700 mm, 680 mm, or 660 mm.

As discussed hereinabove with reference to FIGS. 3A to 3D, it is a particular feature of the teachings herein that temple arm portion 118 is resilient, and that arm member 114 has a predefined preload thereon, such that when the arm member 114 is pulled outwardly, temple arm portion 118 drives the arm member 114 back towards an axis of symmetry of the headset. The various factors that affect the preload, as well as the magnitude of the force applied by arm members under the driving force of the preload, are described hereinabove with reference to FIGS. 3A to 3D.

It is appreciated that the resilience of the temple arm portion 118 provides at least some of the flexibility and resilience required in order to drive the arm members 114 toward the axis of symmetry after they are pulled outwardly. The degree of flexibility of temple arm portion 118 affects the distance to which arm members 114 may be outwardly displaced, such that more flexible temple arm portions 118 allow for greater displacement of arm member 114. It is appreciated that in embodiments in which anterior member 112 is also flexible or semi-flexible, the flexibility thereof may also contribute to the extent to which arm members 114 may be outwardly displaced.

The length A of posterior arm portions 119 is selected such that it will be adapted to span the entire rear portion of the user's head, regardless of the size of the user's head. Specifically, if posterior arm portions 119 are too short, the headset 100 may be not able to close on a person with a large head. Additionally, if posterior arm portions 119 are too short, they may not be able to align with the contour of the rear portion of the user's head while donning the headset, and thus the angle α (FIGS. 3B and 3C) between the closure mechanism 128 and the user's head may be changed, and plowing between the user's hairs may be disrupted.

The size adjustment mechanism 120 may be any suitable size-adjustment mechanism, such as, for example, a slidable mechanism or a ratchet mechanism as known in the art. The length B of size adjustment mechanism 120, as well as the extent to which size adjustment mechanism 120 can change the length of arm member 114 is selected so as to enable a suitable range of circumferences of the headset, while ensuring that the circumference of headset 100, in the closed state, will be fitted to the circumference of the user's head.

Turning to FIG. 14B it is seen that in some embodiments, though posterior arm members 119 and size adjustment mechanism 120, and the lengths thereof, remain the same as in the embodiment of FIG. 14A, the flexible temple arm portion 118 extends through the anterior member 112, for example through a dedicated slot therein, such that it forms an arc extending along approximately half of the circumference of the headset. In some such embodiments, the length of flexible arm portion 118, labeled by C, is smaller than 220 mm, smaller than 180 mm, or smaller than 120 mm. In such embodiments, a longer section of the circumference of headset 100 is flexible and resilient, and contributes to the preload on the arm members 114, as well as to the resilience of arm members 114 and to the extent to which the arm members can be outwardly displaced.

It is appreciated that in embodiments such as that shown in FIG. 14B, anterior member 112 must be structured such that flexible arm portion 118 extending along the anterior member is able to flex, when necessary. For example, anterior member 112 may be at least partially flexible and have arm portion 118 extending through a channel therein, such that arm portion 118 can flex, when necessary. As another example, anterior member 112 may be rigid, and may have arm portion 118 extending along an exterior surface thereof and anchored to the anterior member 112 at a single point in the center, such that arm portion 118 can flex as necessary, without requiring any flexibility of anterior member 112.

FIG. 14C illustrates an embodiment similar to the embodiment of FIG. 14B, in which the flexible temple arm portion 118 extends outside of the anterior member 112, for example internally thereto. In some such embodiments, the length of flexible arm portion 118, labeled by C, is smaller than 220 mm, smaller than 180 mm, or smaller than 120 mm, substantially as described hereinabove with reference to FIG. 14B.

Figure 15:
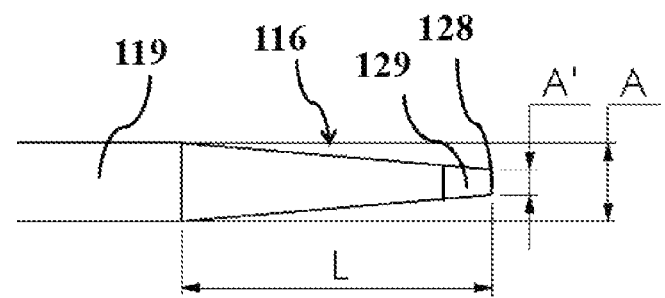
FIG. 15 is a schematic planar top view illustration of a posterior member of an inventive headset suitable for plowing through the hair according to the teachings herein.

It is appreciated that in embodiments such as that shown in FIG. 14C, anterior member 112 must be structured such that flexible arm portion 118 extending along the anterior member is able to flex, when necessary. For example, anterior member 112 may have arm portion 118 anchored to the anterior member 112 at a single point in the center, such that arm portion 118 can flex as necessary, without requiring any flexibility of anterior member 112. Reference is now made to FIG. 15, which is a schematic planar top view illustration of a posterior member of an inventive headset suitable for plowing through the hair according to the teachings herein.

As seen in FIG. 15, in some embodiments, posterior member 116 is tapered, such that the width of the posterior member 116 at the end which is connected to the posterior arm portion 119, indicated by A, is greater than the width of the posterior member 116 at the open end of headset 100 adjacent closure mechanism 128, indicated by A', such that A>A'. In other embodiments, not illustrated herein, the width of posterior member 116 may be fixed throughout the length thereof, such that A=A'. The narrow, and preferably tapered, structure of posterior member 116 allows the posterior member 116 to effectively plow under and/or through the hair and between the roots of the hair in order to reach the scalp surface while pushing the hair away from under the posterior member 116 and electrodes associated therewith and/or disposed at locations where hair is present.

In some embodiments, the width A of posterior member 116 at its widest point is not greater than 40 mm, not greater than 30 mm, or not greater than 20 mm. In some embodiments, the length of posterior member 116, indicated by L, is not greater than 100 mm, not greater than 80 mm, not greater than 60 mm, or not greater than 50 mm. In some embodiments, the length of posterior member 116, indicated by L, is not less than 5 mm, not less than 10 mm, or not less than 20 mm.

It is appreciated that in embodiments in which posterior member 116 has an electrode system disposed thereon, such as that illustrated in FIGS. 1A and 1B, the dimensions of the posterior member 116 must be sufficiently large to house the electrode system, and therefore are restricted by the minimal electrode dimensions. In embodiments in which no electrode is disposed on the posterior member 116, any suitable dimensions may be used, and the dimensions may be determined based on other parameters, such as ease of use when donning the headset, effectiveness of the posterior member in plowing away the hair, and the like.

It is further appreciated that in some embodiments, such as embodiments in which posterior member 116 includes an electrode system, the tapering of the width of posterior member 116 need not be linear along the length of the posterior member, and/or the posterior member need not be tapered along the entirety of its length. For example the posterior member may include an electrode portion having a fixed width or tapering very slightly, and may taper at a greater angle in a second portion, distal to the electrode, to reach width A' at the closure mechanism.

Figure 16A:
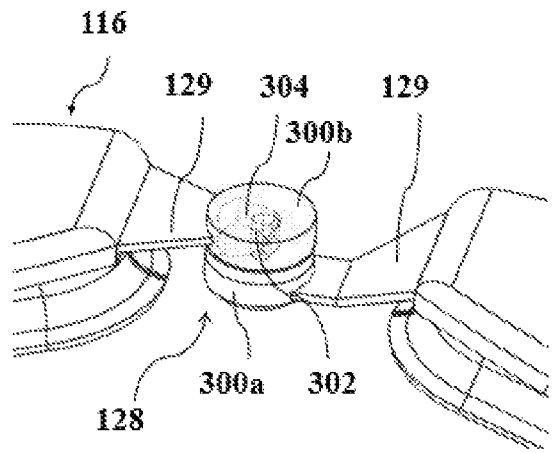
FIGS. 16A and 16B are perspective view illustrations of two embodiments of a closure mechanism for closing the inventive headset of FIGS. 1A and 1B according to the teachings herein.
Figure 16B:
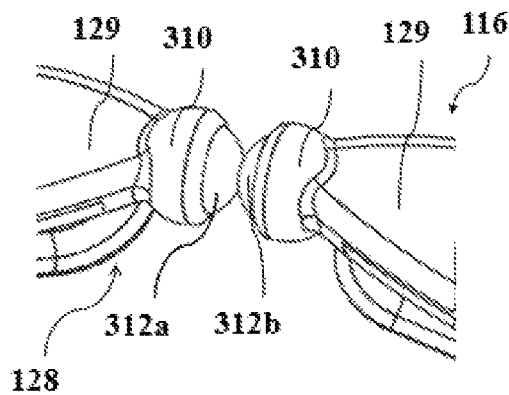

Reference is now made to FIGS. 16A and 16B, which are perspective view illustrations of two embodiments of a magnetic closure mechanism 128 for closing the inventive headset of FIGS. 1A and 1B according to the teachings herein.

It is appreciated that a magnetic closure mechanism 128 is advantageous over use of other types of closure mechanisms, as the two portions of the closure mechanism may attract one another and thus close without requiring the user donning headset 100 to directly interact with or manipulate closure mechanism 128. This is particularly useful in the donning method of the inventive headset 100, since the user's hands typically hold the headset at side portions thereof during the donning process, as shown in FIGS. 3A to 3D, and thus are not free to manipulate the closure mechanism.

FIG. 16A illustrates a closure mechanism 128 based on use of one or more magnets. As seen, in some embodiments, posterior members 116 each have a tapered end 129 terminating in a magnetically attractable portion 300. In some embodiments, both magnetically attractable portions 300*a* and 300*b* are magnets. In other embodiments, one of magnetically attractable portions 300*a* and 300*b* is a magnet, while the other is formed of a metal which is attracted to the magnet.

One magnetically attractable portion 300*a* includes a pin 302, whereas the other magnetically attractable portion 300*b* includes a bore 304 suitable for housing pin 302. Magnetically attractable portions 300 are arranged so as to attract one another when disposed adjacent one another, thereby directing pin 302 to engage bore 304 and to secure the headset on the user's head. In some embodiments, not shown in FIG. 16A, the magnets 300 may lie generally perpendicular to tapered ends 129, such that there is no need to overlap the magnetically attractable portions one over the other in order to secure the pin 302 in bore 304. In some embodiments, the one or more magnets comprise Neodymium magnets.

FIG. 16B illustrates another closure mechanism 128 based on use of magnetic attraction. As seen, posterior members 116 each have a tapered end 129 terminating in a housing 310, housing a magnetically attractable portion 312 comprising at least a section of a sphere defining at least one spherical surface. In some embodiments, both magnetically attractable portions 312*a* and 312*b* are magnets. In other embodiments, one of magnetically attractable portions 312*a* and 312*b* is a magnet, while the other is formed of a metal which is attracted to the magnet.

In some embodiments, the magnetically attractable portions 312 comprise a section of a sphere, such as a spherical cap or half a sphere. In other embodiments, the magnetically attractable portions 312 comprise a sphere. In some embodiments, the spherical surface of the magnetically attractable portions 312 has a radius in the range of 2 to 20 mm, in the range of 3 to 15 mm, or in the range of 4-10 mm. In some embodiments the holding force of one or more magnets of magnetically attractable portions 312 is in the range of 0.5 to 15 N, in the range of 1 to 10 N, or in the range of 1.5 to 7 N.

Magnetically attractable portions 312 are adapted to engage one another at the spherical surface thereof, thereby to close headset 100. Due to the spherical shape of the engagement surface of magnetically attractable portions 312, the contact point between the two magnetically attractable portions 312 is minimal and is substantially a single point, thereby preventing pinching of the user's hair within the closure mechanism 128.

In some embodiments, magnetically attractable portions 312 are rotatable within housing 310 and are arranged so as to attract one another when disposed at a small distance from one another so as to make it easier for the user to close the headset 100 while donning the headset, without seeing the closure mechanism 128, as explained hereinabove with reference to FIGS. 3A to 3D. In some embodiments, the magnetically attractable portions are arranged so as to attract one another when they are at a distance not greater than 10 mm, not greater than 20 mm, or not greater than 30 mm. Furthermore, due to the magnetically attractable portions' ability to rotate within housing 310, the polar orientation of the one or more magnets of the magnetically attractable portions may adjust itself to an optimal orientation or alignment between the two magnets at a given alignment of or angle between posterior members 116. In some embodiments, the magnets comprise Neodymium magnets.

It is appreciated that any suitable closure mechanism may be used for securing headset 100 so that it does not fall or move when donned. However, it is a particular feature of the teachings herein that in all of the embodiments illustrated in FIGS. 16A and 16B, the footprint of closure mechanism 128, and specifically the footprint of surfaces of closure mechanism 128 that contact each other when the closure mechanism is closed, is small, thereby reducing, and in some cases even preventing, hair from being caught in and/or pulled by elements of the closure mechanism 128 while closing the headset on the user's head.

Figure 17A:
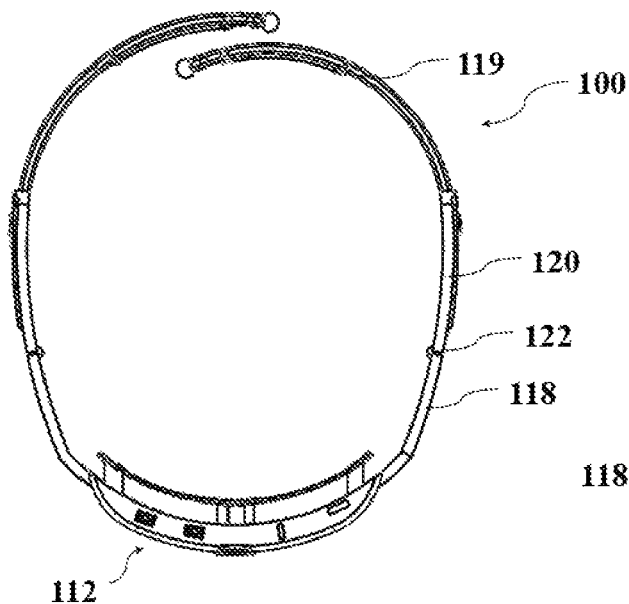
FIGS. 17A and 17B provide top plan view illustrations of the inventive headset of FIGS. 1A and 1B in a rest state, in an open and a folded position, respectively.
Figure 17B:
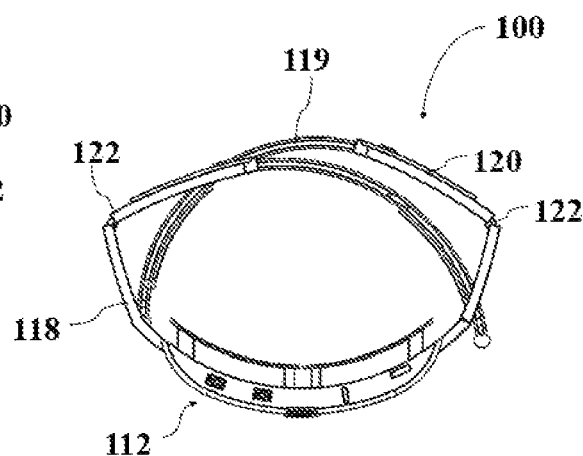

Reference is now made to FIGS. 17A and 17B, which provide top plan view illustrations of inventive headset of FIGS. 1A and 1B in a rest state and in a folded position, respectively. FIG. 17A shows headset 100 in the rest state, as described hereinabove with reference to FIGS. 1A and 1B.

FIG. 17B shows headset 100 in a folded position, where arm members 114 are folded at hinges 122 in a similar manner to that in which eyeglasses fold. Any suitable type of hinge mechanism 122 may be used for folding arm members 114, such as a spring hinge, a barrel hinge, an interlocking hinge, and an integrated hinge built into arm members 114. Further, the hinge mechanism 122 may be formed of any suitable type of material, including plastic and metal such as stainless steel. However, as described hereinbelow with reference to FIGS. 18A and 18B, in some embodiments in which electrical conductors are required to pass through the hinge, certain types of hinges, such as integral hinges, are less suitable.

Reference is now made to FIGS. 18A and 18B, which are schematic illustrations of an embodiment of electrical conductors embedded in a hinged arm member 114, which electrical conductors are suitable for use in inventive headsets according to the teachings herein, FIG. 18A illustrating the arm member 114 in a folded position, and FIG. 18B illustrating the arm member 114 in an open position, respectively.

As seen, and as discussed hereinabove with respect to FIGS. 17A and 17B, in some embodiments the arm members 114 of headset 100 include a hinge portion 320, including hinge 122 disposed between an first end surface 324 and a second end surface 326 of arm member 114, such that in a folded position of the hinge portion 320, illustrated in FIG. 18A, end surfaces 324 and 326 do not engage one another other than by hinge 122, and in the open position of hinge portion illustrated in FIG. 18B, first end surface 324 engages the second end surface 326 of arm member 114.

It is appreciated that in certain embodiments, particularly ones in which the power supply and/or the processing unit of headset 100 are disposed in anterior member 112 and need to provide power and/or processing instructions to posterior electrodes 140, electric conductors must extend along at least one of arm members 114 through at least one hinge portion 320.

In some such embodiments, the a first electrical conductor 330 electrically connected to anterior member 112 terminates, at the first end surface 324 in a metal contact bore 332, and a second electrical conductor 334 electrically connected to posterior member 116 terminates, at second end surface 326 of arm member 114, in a metal contact pin 336.

As illustrated in FIG. 18A, when hinge portion 320 is in the folded position, metal contact pin 336 is disengaged from metal contact bore 322, such that anterior member 112 is electrically disconnected from arm member 114 and/or from posterior member 116. By contrast, when hinge portion 320 is in the open position, shown in FIG. 18B, metal contact pin 336 is disposed within metal contact bore 332 and is in electrical contact therewith. As such, when the hinge portion 320 is in the open position, current and processing instructions can be conducted between the anterior member 112, arm members 114, and posterior members 116.

Reference is now made to FIG. 19, which is schematic illustration of an embodiment of electrical conductors embedded in a size adjustment mechanism, which electrical conductors are suitable for use in inventive headsets according to the teachings herein.

As discussed hereinabove with reference to FIGS. 14A and 14B, arm members 114 include a size adjustment mechanism 120. As mentioned herein, the size adjustment mechanism 120 is disposed between the anterior member 112 and the posterior member 116, such that for current to be conducted between the anterior member 112 and the posterior member 116, electrical conductors must extend through arm members 114 and through size adjustment mechanism 120.

In some embodiments, the size adjustment mechanism 120 comprises a sliding and/or ratcheting adjustment mechanism, including a slot 340 formed in temple arm portion 118, and a flexible arm portion 342 extending from posterior arm portion 119 and disposed within slot 340 and slidably movable therein.

A first, flat electrical conductor 344, extends from anterior member 112, along temple arm portion 118 and along slot 340. A second electrical conductor 346 extends along posterior arm portion 119 and along flexible arm portion 342 thereof, and terminates in a contact spring 348 within slot 340, such that contact spring 348 is in electrical contact with flat electrical conductor 344 within the slot. Thus, electrical conduction through size adjustment mechanism 120 is accomplished by electrical contact between the flat electrical conductor 344 and the contact spring 348, regardless of the position of flexible arm portion 342 within slot 340.

It is appreciated that any other mechanism for conducting electricity through the size adjustment mechanism 120 is also considered within the scope of the invention, provided that current can be transferred from the anterior member 112 to the posterior member 116 without causing harm or risk to the user.

Figure 20:
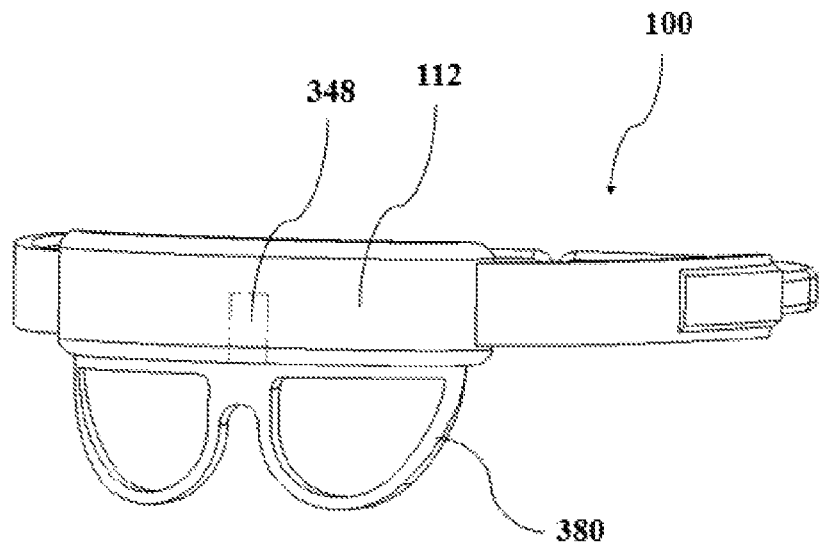
FIG. 20 is a perspective anterior view illustration of an embodiment of an inventive headset according to the teachings herein including associated eyeglasses.

Reference is now made to FIG. 20, which is a perspective anterior view of the inventive headset 100, including associated eyeglasses 380.

Eyeglasses 380 may be configured to be located in the central area of anterior member 112. Positioning the eyeglasses 380 over the nose and eyes may allow the user to determine the rotational and longitudinal placement of headset 100, for example while donning the headset.

Eyeglasses 380 may also be configured to further support anterior member 112 against gravity, thereby enabling the user to more easily don headset 100, substantially as described hereinabove with reference to nose bridge 170 of FIG. 1C. In some embodiments, eyeglasses 380 are removably attached to anterior member 112 by at least one tab 384, configured to be inserted into at least one corresponding slot in anterior member 112, and may be detached from the anterior member 112 by pulling tab(s) 384 out of the slot(s) in which they are housed. In some embodiments, tab(s) 384 of eyeglasses 380 and tab(s) 174 of nose bridge 170 (FIG. 1C) are similarly sized, such that the nose bridge 170 and eyeglasses 380 may be interchangeably connected to anterior member 112 using the same slot.

In some embodiments, eyeglasses 380 may comprise optical lenses for improved eyesight, dark lenses suitable to be used as sunglasses, non-optical transparent lenses, or highly dark lenses that may be used to block external light, for example, in order to assist during migraine attack or for relaxation.

It is appreciated that in some embodiments, eyeglasses 380 may be replaced with any suitable optical or ocular element, such as goggles and the like.

Figure 21:
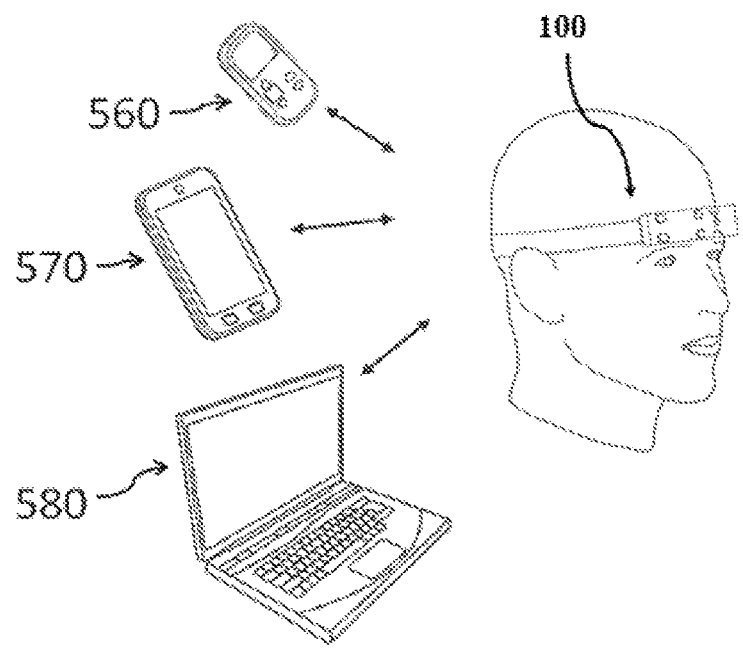
FIG. 21 provides a perspective view illustration of a donned, inventive headset adapted to communicate with a remote control unit, mobile phone, and computer.

FIG. 21 illustrates a perspective view of headset 100 along with a remote control or remote control handset 560, a mobile phone 570 and a laptop/PC 580.

In some embodiments, headset 100 may be configured to communicate wirelessly with remote control 560. Remote control 560 may be used by the user to send commands to headset 100, such as stimulation initiation or cessation commands, or commands to increase or decrease the stimulation intensity. Remote control 560 may also present various visual and audio indications for the user regarding the status of headset 100.

Headset 100 may be configured to wirelessly communicate with a mobile phone 570. The mobile phone interface may be used to present various data sent wirelessly by headset 100, for example, visual and audio indications regarding the status of headset 100 and usage logs.

Headset 100 may be configured to wirelessly communicate with laptop/PC 580. The mobile phone interface may be used to present various data sent wirelessly by headset 100, such as visual and audio indications regarding the status of headset 100 and usage logs.

Communication between headset 100 and remote control 560, mobile phone 570 and laptop 580 may be performed in various ways, known to those of ordinary skill in the art, for example by Bluetooth communication.

Figure 22A:
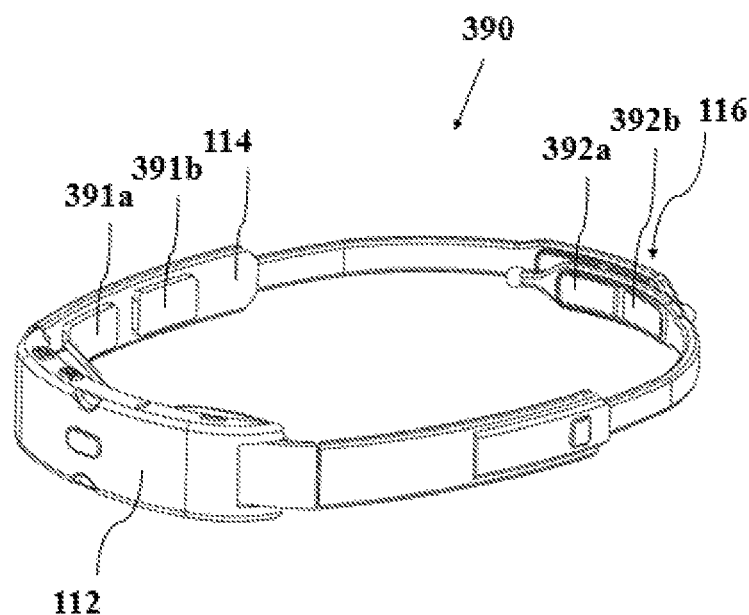
FIGS. 22A and 22B are perspective view illustrations of an embodiment of the inventive headset of FIGS. 1A and 1B, including side electrodes, as well as split anterior and posterior electrodes.
Figure 22B:
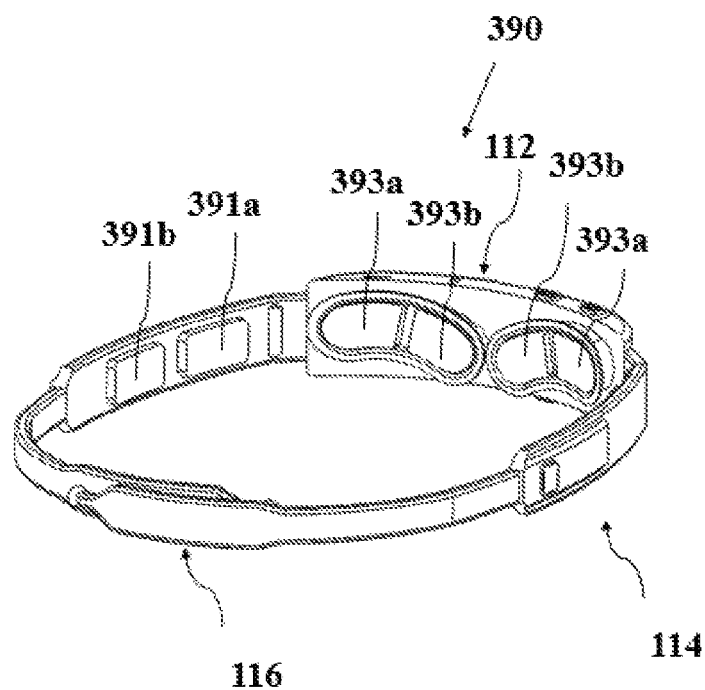
Figure 23A:
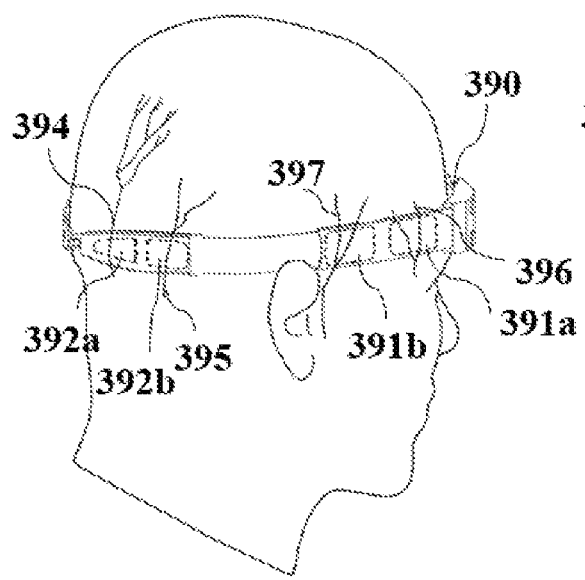
FIGS. 23A and 23B are schematic illustrations of the headset of FIGS. 22A and 22B positioned on the head of a user, such that electrodes included therein stimulate specific nerve junctions in the head of the user.
Figure 23B:
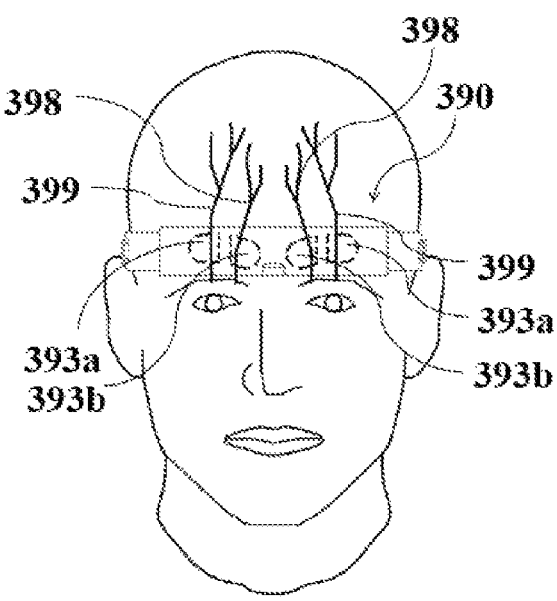
Figure 23C:
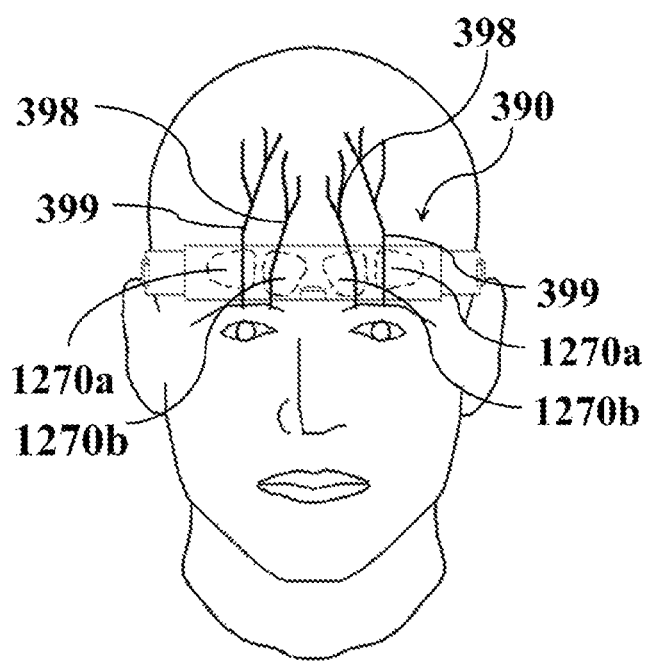
FIG. 23C is a schematic illustration of a headset including the electrodes of FIG. 10D positioned on the head of a user, such that electrodes included therein stimulate specific nerve branches in the head of the user.

Reference is now made to FIGS. 22A and 22B, which are perspective view illustrations of an embodiment of an inventive headset 390, similar to the inventive headset 100 of FIGS. 1A and 1B, including side electrodes as well as split anterior electrodes and split posterior electrodes, to FIGS. 23A and 23B, which provide schematic illustrations of the headset 390 positioned on the head of the user, such that electrodes included therein stimulate specific nerve branches in the head of the user, and to FIG. 23C, which is a schematic illustrations of a headset including the electrodes 1270a and 1270b of FIG. 10D positioned on the head of a user, such that electrodes included therein stimulate specific nerve junctions in the head of the user.

As seen in FIGS. 22A and 22B, in some embodiments, one or more side electrodes 391 are mounted on each of flexible arm members 114. In the illustrated embodiments, each arm member 114 may include a proximal side electrode 391a disposed on the arm member 114 near anterior member 112, and a distal side electrode 391b disposed on the arm member 114 near the distal end of arm member 114. In some embodiments, when headset 390 is donned by the user, some or all of side electrodes 391 are located at areas including hair, and are in direct contact with the skin due to plowing away of the hair by closure mechanism 128 as described hereinabove.

It is appreciated that side electrodes 391 are constructed and operative similar to electrodes 130 and 140 described hereinabove with respect to FIGS. 1A and 1B. It is appreciated that in some embodiments (not illustrated), the side electrodes 391 may be the main or the only electrodes included in headset 390, and thus electrodes 130 and/or 140 may be obviated. It is further appreciated that in some embodiments some or all of side electrodes 391 may be sensing electrodes, such as electroencephalogram (EEG) electrodes, skin conductance response (SCR) electrodes, impedance plethysmograph (IPG) electrodes, or electromyograph (EMG) electrodes.

Additionally, as seen with particular clarity in FIG. 22A, headset 390 includes split posterior electrode systems including electrodes 392a and 392b, structured substantially as described hereinabove with reference to FIG. 13B, and configured to operate similarly to electrode systems 140 of FIGS. 1A and 1B.

Turning specifically to FIG. 22B, it is seen that headset 390 includes split anterior electrode systems including electrodes 393a adjacent arm members 114 and 393b adjacent the center of the anterior member, structured substantially as described hereinabove with reference to FIG. 10B, and configured to operate similarly to electrode systems 130 of FIGS. 1A and 1B.

As seen in FIGS. 23A and 23B, each of the electrodes included in headset 390 and/or in headset 100 of FIGS. 1A and 1B is configured to be positioned, when the headset is donned on the head of a user, above one or more specific nerves or brain regions for stimulation thereof.

Turning to FIG. 23A, it is seen that posterior electrode system 392a may be positioned to stimulate the greater occipital nerve, indicated by reference numeral 394, and posterior electrode system 392b may be positioned to stimulate the lesser occipital nerve, indicated by reference numeral 395, and/or the third occipital nerve (not illustrated). Alternatively, posterior electrode systems 140 may be positioned to simulate at least one of the greater occipital nerve 394 the lesser occipital nerve 395, and the third occipital nerve (not illustrated). In some embodiments, such as when conducting transcranial stimulation, at least one of posterior electrodes 140 or 392a and 392b may be activated simultaneously with at least one anterior electrode 130 or 393a and 393b or with at least one side electrode 391, thereby to stimulate regions of the frontal, temporal, and/or occipital lobes of the user's brain.

In some embodiments, proximal side electrodes 391a may be positioned to stimulate the zygomaticotemporal nerve indicated by reference numeral 396, and distal side electrodes 391b may be positioned to stimulate the auriculotemporal nerve, indicated by reference numeral 397. In some embodiments, such as when conducting transcranial stimulation, at least one of side electrodes 391 may be activated simultaneously with at least one anterior electrode 130 or 393a and 393b, with at least one contralateral side electrode 391, or with at least one posterior electrode 140 or 392a and 392b, thereby to stimulate regions of the frontal, temporal, and/or occipital lobes of the user's brain.

Turning to FIGS. 23B and 23C, it is seen that anterior electrode systems 130 disposed on anterior member 112 may be positioned to stimulate the right and left branches of the supratrochlear nerve, indicated by reference numeral 398, and/or the right and left branches of the supraorbital nerve, indicated by reference numeral 399. Alternatively, anterior electrode system 393a may be positioned to stimulate a branch of the supraorbital nerve 399 and anterior electrode system 393b may be positioned to stimulate the supratrochlear nerve 398. In the embodiment of FIG. 23C, the electrode systems 393a and 393b are shaped and configured similarly to respective electrodes 1270a and 1270b, described hereinabove with respect to FIGS. 10C and 10D.

As is known in the art, major challenge in stimulation of nerves in the head region is reaching sufficient nerve excitation without causing sensory discomfort or pain. The supraorbital and supratrochlear nerve branches (trigeminal nerve—ophthalmic division) are located superficially at the supraorbital region in close proximity to the periosteum of the skull bone which is densely innervated by nociceptive nerve fibers. Due to this unique anatomical proximity, attempts to conventionally stimulate the supraorbital and supratrochlear nerve branches typically result in concurrent excitation of the periosteum's nociceptive nerves which elicit a pain sensation. The inventors discovered that it is possible to effectively stimulate the supraorbital and supratrochlear nerve branches without causing pain by confining the stimulating electrodes to be located over a very specific anatomical region and by using an array of two pairs of electrodes. The electrodes in each pair are adapted to be in contact with the user's forehead above the target nerves while their lower edge is placed in close proximity to the user's eyebrows, the electrodes having a small distance between them. The current is confined to flow between the two electrodes of each pair, such that one pair is adapted to stimulate the left supratrochlear and supraorbital nerves and the second pair is adapted to stimulate the right supratrochlear and supraorbital nerve branches. The inventors discovered that this specific electrode arrangement and configuration facilitates effective isolated excitation of the target nerves while preventing deeper penetration of the electrical current to the pain conducting nerves located in the periosteum of the skull bone as well as to other areas of the forehead which were found to elicit painful sensation.

The inventors have further discovered that a similar electrode arrangement and configuration in the occipital region of the user's head facilitates effective isolated excitation of the target nerves while preventing stimulation of nociceptive nerve fibers in the periosteum.

Figure 24:
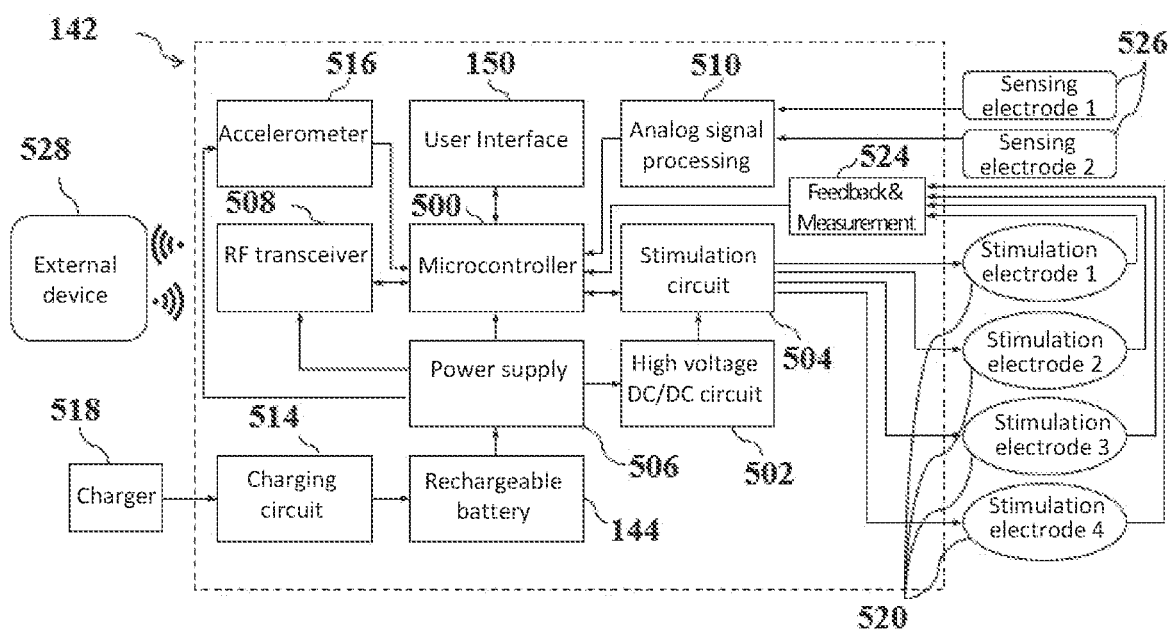
FIG. 24 is a schematic block diagram of an embodiment of an electronic circuit usable in an inventive headset according to any of the embodiments described herein.

Reference is now made to FIG. 24, which provides a schematic block diagram of an embodiment of an electronic circuit usable in an inventive headset according to any of the embodiments described herein, such as headset 100 of FIGS. 1A and 1B or headset 390 of FIGS. 22A to 23B.

As seen, an electronic circuit, such as electronic circuit 142 described hereinabove with reference to FIGS. 1A and 1B, may include any one or more of a microcontroller 500, a high voltage circuit 502, a stimulation circuit 504, an internal power supply 506, a radio-frequency (RF) transceiver 508, an analog signal processing circuit 510, a rechargeable battery electrically associated with circuit 340, such as battery 144 of FIG. 1A, a charging circuit 514, an accelerometer 516, and a user interface 150, for example as described hereinabove with reference to FIG. 1A. In some embodiments, electronic circuit 142 may include additional sensors, not shown, as described hereinbelow.

As mentioned hereinabove, the electronic circuit 142 may be electrically associated with, and powered by rechargeable battery 144 that is electrically connected to internal power supply 506. In some embodiments, the internal power supply 506 provides power to high voltage circuit 502, which in turn is electrically connected to stimulation circuit 504. The charging circuit 514 is electrically associated with rechargeable battery 144, and may interface with an external power supply, such as a charger 518. The high voltage circuit 502 provides to stimulation circuit 504 current with voltage measuring up to 120.

In some embodiments, the stimulation circuit 504 receives information and/or commands from the microcontroller 500. The stimulation circuit 504 is configured to provide electrical stimulation pulses to the user's nerve tissues via one or more stimulation electrodes 520 disposed on the headset, such as stimulation electrodes 130 and/or 140 of FIG. 1, and stimulation electrodes 391, 392, and 393 of FIGS. 22A and 22B.

In some embodiments, electronic circuit 142 may include two or more high voltage circuits (not shown) similar to circuit 502, each high voltage circuit providing current at a voltage of up to 120 volts to at least two of stimulation electrodes 520. In some embodiments, electronic circuit 142 may include at least two galvanic isolated output channels (not shown), each output channel providing output to at least two of stimulation electrodes 520.

In some embodiments, the electronic circuit 142 also includes a feedback & measurements circuit 524, which collects voltage or current level information from the stimulation electrodes 520, and provides the collected information to the microcontroller 500. The microcontroller 500 uses the provided feedback to monitor and control the voltage and current levels in stimulation electrodes 520 in order to maintain the desired stimulation level, to optimize energy consumption, and to ensure the user's safety. In some embodiments, the microcontroller 500 may alert the user, for example by providing an audible or tactile indication, or may halt the provision of current for stimulation in the case of an emergency or of incorrect function of the headset. For example, microcontroller 500 may alert the user and may halt the provision of current for stimulation if a reduction of current level is detected as a result of improper contact of one or more of electrodes 520 with the user's skin.

In some embodiments, the microcontroller 500 may instruct the stimulation circuit 504 to output electrical current in various patterns and/or for various periods of time. For example, the microcontroller 500 may instruct the stimulation circuit 502 to provide electrical current having an amplitude that ramps up, ramps down, or remains stable. In some embodiments the microcontroller 500 instruct the stimulation circuit 504 with regards to various stimulation parameters, such as the current amplitude, pulse frequency, phase duration, and amplitude of the current output by the stimulation circuit. In some embodiments, the microcontroller instructs the stimulation circuit 504 to provide an output having a constantly changing pattern of at least one of the stimulation parameters.

In some embodiments, the microcontroller 500 may instruct the stimulation circuit 504 to provide an output signal having a different pattern for each of a plurality of activated pairs of electrodes. For example, the stimulation circuit 504 may stimulate one pair of electrodes at a pulse frequency of 50 Hz and a phase duration of 300 μsec and another pair of electrodes at a pulse frequency of 100 Hz and a phase duration of 200 μsec. In some embodiments, at any given time the microcontroller 500 may activate only one pair of electrodes, may activate a combination of electrodes, may activate several electrodes simultaneously, sequentially, or alternately.

In some embodiments, some electrodes 520 may provide as output an alternating current signal, whereas other electrodes 520 may provide as output a direct current. In some embodiments, at least two electrodes 520 may alternate the type of current provided as output between alternating current and direct current.

In some embodiments, during direct current stimulation in which excitation of a certain region of the brain is determined based on the polarity of an electrode which is positioned above that region of the brain, at least one electrode 520 may be assigned by the microcontroller 500 to be the anode, or positively charged electrode, and at least one other electrode 520 may be assigned to be the cathode, or negative charged electrode.

In some embodiments, stimulation patterns determined by or assigned by the microcontroller 500 as described above may be stored in the microcontroller 500 or in a volatile or non-volatile memory (not shown) associated therewith, and may activated by the user. In some embodiments, the stored stimulation patterns may be modified by the user, for example using user interface 150 included in the headset, or using an external user interface. In some embodiments, a clinician may modify the stored stimulation pattern for a patient physically when the patient visits the clinician, or remotely, such as via a remote cloud base portal which is in communication with the patient's external interface.

In some embodiments, electronic circuit 142 may be configured to receive analog signal input, such as electroencephalogram (EEG) signals, skin conductance response (SCR) signals, impedance plethysmograph (IPG) signals, electromyograph (EMG) signals, or other bio-signals, from one or more sensors, such as sensing electrodes 526. The analog signal input received from sensing electrodes 526 may be processed by analog signal processing circuit 510, and may be transferred therefrom to microcontroller 500. In some embodiments, electronic circuit 142 may be configured to receive digital, analog, or other input from additional sensors disposed on or within the headset, or located elsewhere in the vicinity of the user. In some embodiments, one or more stimulation parameters may be altered by the microcontroller 500 due to inputs received from one or more of the additional sensors. For example, upon receiving certain EEG input from the analog signal processing circuit 510, the microcontroller 500 may modify one or more parameters of the stimulation current which is provided by the stimulation circuit 504, such as current amplitude, pulse frequency, and the like. In some embodiments, upon receiving input from the analog signal processing circuit 510, the microcontroller 500 may activate a specific combination and/or sequence of electrodes and/or may modify the duration of stimulation provided by certain electrodes.

In some embodiments, accelerometer 516, or any other suitable orientation sensor, may be configured to sense the angular position of the headset and thereby to provide an indication for proper placement of the headset on the user's head. For example, in case that the user positions the headset upside down on his head, the accelerometer may transfer headset orientation data sensed thereby to microcontroller 500, which may detect the misplacement of the headset and may prevent activation of the electrodes as long as the undesired position of the headset maintained. The user may be alerted to the misplacement of the headset, for example by user interface 150 or by a remote interface, and may be instructed to correct the headset position.

In some embodiments, input received from the additional sensors and/or from sensing electrodes 526 may be transferred directly to the patient's clinician or care giver, for example via and external interface and a cloud based portal, allowing the clinician or care giver to monitor the patient's condition, and to alter the patient's treatment program and stimulation pattern accordingly.

In some embodiments, RF transceiver 508 may enable the microcontroller 500 to communicate with an interface of an external device 528, such as a mobile phone, a tablet, or a computer by way of radio frequency. The RF transceiver 508 may transmit digital information to and may receive digital information from the microcontroller 500.

The interface of device 528 may comprise a software application that may be downloadable from a readily accessible resource, such as from the Internet. The interface may provide to a user thereof an indication, for example by way of a display, of the status of the headset, including, for example, information relating to active stimulation channels, stimulation intensity, active program, treatment time, headset battery status, and RF communication status, as well as various alerts such as alerts relating to electrode contact quality and to proper or improper headset alignment on the head. Additionally, the interface may provide to the user, for example by way of a display, usage logs and/or reports, such as information relating to daily stimulation time, stimulation parameters which were used during stimulation, and treatment programs which were used. The interface may also display, or otherwise provide, to the user raw or processed information received from sensors included in or associated with the headset.

In some embodiments, the headset may be controlled remotely via the interface of external device 528. For example, the external interface may enable a user thereof to activate or turn off the headset, start or pause stimulation, adjust the stimulation intensity for one or more channels, and select a treatment program. In some embodiments, information collected by the microprocessor 500 may be transmitted, via the external interface, to a remote location, such as a cloud based portal, where the information may be stored or may be analyzed and/or monitored, for example by a clinician or care taker. In some embodiments, patients undergoing treatment using the headset may use the interface of external device 528 to provide input or information regarding their condition, thereby enabling a clinician to monitor the patient's condition and provide recommendations for a modified treatment program or actively modify the patient's stimulation parameters remotely in real time. The patient may also use the external interface to download new treatment programs to the headset.

In some embodiments, user interface 150 located on the headset and the external user interface may enable parallel control of the headset, allowing the user to operate the headset by either of the interfaces. In some embodiments, the external interface serves as a display only and does not provide active control of the headset. In some embodiments, user interface 150 on the headset is obviated, and all interaction with the headset is carried out via the external interface. In some embodiments, the external interface comprises a proprietary electronic device. In some embodiments, the external interface may communicate with electronic circuit 142 via a cable, such as a USB cable.

Figure 25:
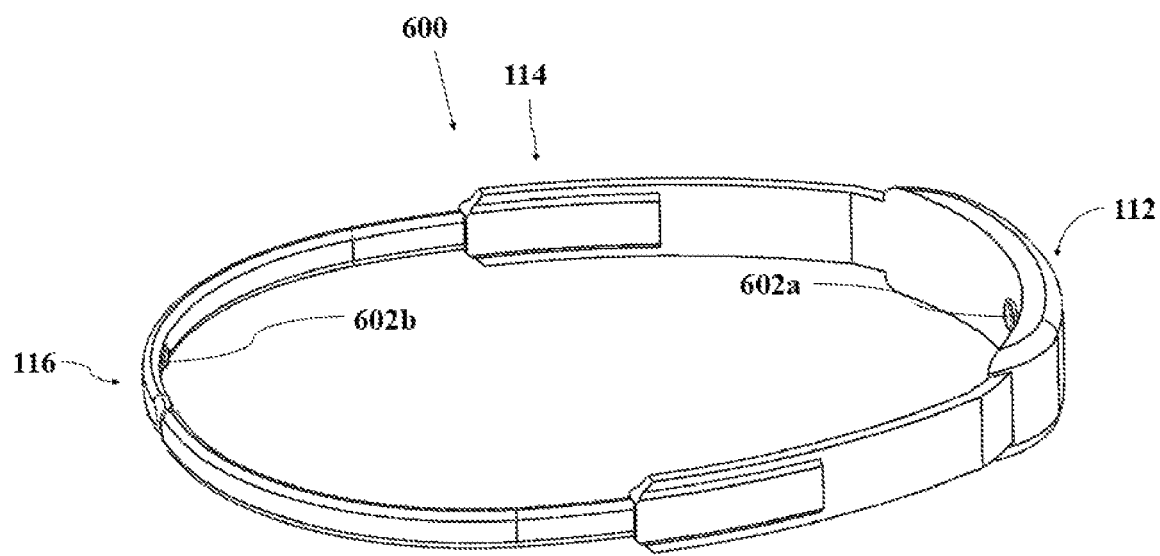
FIG. 25 is a perspective view of an embodiment of an inventive headset, similar to the inventive headset of FIGS. 1A and 1B, including sensors of body parameters.

Reference is now made to FIG. 25, which is a perspective view of an embodiment of an inventive headset 600, similar to the inventive headset 100 of FIGS. 1A and 1B, including sensors 602.

As seen in FIG. 25, in some embodiments, one or more sensors 602 are mounted on headset 600, and are configured to sense various body parameters of the user when the headset is donned. In the illustrated embodiments, one or more anterior sensors 602a are disposed on anterior member 112, and one or more posterior sensors 602b are disposed on posterior members 116. However, it is appreciated that sensors 602 may be disposed at any suitable location on headset 600, for example on arm members 114. In some embodiments, headset 600 may include stimulating or sensing electrodes, such as electrodes 130 and 140 of FIGS. 1A and 1B, in addition to sensors 602.

The sensors 602 may include any suitable type of sensor, such as temperature sensors, orientation sensors, blood pressure sensors, pulse oximetry sensors, electrical conductivity sensors such as sensors for measuring skin conductance response (SCR) and impedance plethysmograph (IPG), electroencephalogram (EEG) and electromyograph (EMG).

The user dons headset 600 in a similar manner to that described hereinabove with reference to FIGS. 3A to 3D, such that closure mechanism 128 plow through the hair and enable posterior sensors 602b to directly engage the skin of the scalp, and not to be obstructed by layers of hair located thereunder.

As used herein in the specification and in the claims section that follows, the term "or" is considered as inclusive, and therefore the phrase "A or B" means any of the groups "A", "B", and "A and B".

As used herein in the specification and in the claims section that follows, the term "circumferential" means forming a closed shape encompassing 360 degrees of a circle.

As used herein in the specification and in the claims section that follows, the term "operational mode", or the like, with respect to a headset or headset component, refers to a headset or headset component that is fitted onto the head of the user, in a suitable rotational and longitudinal disposition, with electrical stimulation being applied.

As used herein in the specification and in the claims section that follows, the term "donned mode", "donned", or the like, with respect to a headset or headset component, refers to a headset or headset component that is fitted onto the head of the user, in a suitable rotational and longitudinal disposition, with electrical stimulation being applied.

As used herein in the specification and in the claims section that follows, the term "integral" refers to a structure behaving as a single, whole structure. The term may be applied in particular to flexible structures such as an electrode pad.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Similarly, the content of a claim depending from one or more particular claims may generally depend from the other, unspecified claims, or be combined with the content thereof, absent any specific, manifest incompatibility therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A headset comprising:
an elongate body member configured to fully encircle the head of a user, said elongate body member having a monolithic structure and having a rest state and a closed state and comprising:
(i) an anterior section; and
(ii) a pair of arm sections configured to be positioned above the user's ears, each arm section being flexible and resilient, and extending away from said anterior section and terminating in a posterior section which terminates in a posterior end;
at least one size-adjustment mechanism configured to enable adjustment of the circumference of said body member to comfortably fit circumferentially about heads having different circumferences, at different times:
a closure mechanism associated with said posterior ends of said arm sections, said closure mechanism having an open position and a closed position, wherein, when said closure mechanism is in said closed position, said body member is in said closed state whereby said headset is fully circumferential; and
a processing unit,
a pair of posterior electrodes configured to be positioned against the skin of the head of said user, each mounted on an inner surface of one of said posterior sections, each posterior electrode of said pair being adapted to electrically communicate with the processing unit,
wherein, in said closed state of said headset, a distance between said posterior electrodes is fixed regardless of an adjusted size of said headset,
wherein the headset is configured, when said headset is donned on the head of the user, to urge said posterior electrodes to be positioned against the skin of the head of said user,
wherein said arm sections have a predefined preload such that when said arm sections are outwardly displaced, said preload drives said arm members toward each other, and
wherein, following placement of said posterior ends above the user's ears, while said headset is pushed rearwardly, said posterior ends are configured to apply a force to the head such that said posterior ends continuously engage the head.

2. The headset of claim 1, wherein, in said rest state, said posterior sections of said arm sections at least partially overlap one another, and in said closed state, said posterior sections and said posterior ends of said arm sections do not radially overlap one another.

3. The headset of claim 1, wherein said predefined preload is adapted to ensure that said posterior ends are configured to engage the scalp of said user and to plow between the hair while said headset is pushed rearwardly during donning thereof, such that when said headset is donned, said posterior electrodes are configured to be in direct physical contact with said scalp of said user.

4. The headset of claim 3, wherein when said headset is donned, said posterior electrodes are also configured to be in direct electrical contact with said scalp of said user.

5. The headset of claim 1, wherein said arm sections are configured such that during donning of said headset, each said posterior end engages a respective sides of the head of said user forming an angle between said posterior end and said respective side of the head of said user, which angle contributes to contact between each said posterior ends and the scalp throughout said donning of the headset.

6. The headset of claim 1, wherein said closure mechanism comprises a magnetic closure mechanism including a magnetically attractable element at each of said posterior ends of said arm sections, said magnetically attractable elements being adapted to attract and engage one another, thereby to close said headset.

7. The headset of claim 6, wherein each of said magnetically attractable elements has at least a portion which defines a spherical surface and is disposed in a housing, wherein said spherical surfaces of said magnetically attractable elements are adapted to engage one another at a single point, thereby to close said headset.

8. The headset of claim 1, wherein each said posterior electrode has a resilient, flexible, sealing rim disposed therearound, such that when said posterior electrode engages a skin surface of said user, said sealing rim seals around said posterior electrode.

9. The headset of claim 1, further comprising at least one anterior electrode mounted on an inner surface of said anterior section, the headset having at least one of the following structural features:
at least one of said at least one anterior electrode is configured, when said headset is donned, to be disposed above at least one of the supratrochlear nerves or the supraorbital nerves of said user; and
at least one of said at least one anterior electrode comprising a transcranial stimulation electrode configured, when said headset is donned, to be disposed above an anterior brain region of said user.

10. The headset of claim 9, wherein:
said at least one anterior electrode comprises a first anterior electrode and a second anterior electrode, each of said first and second anterior electrodes having a first end, a second end, a height, and a length,
said heights of said first and said second anterior electrodes, at a maximal point thereof, being in the range of 10 mm to 40 mm,
said first and second anterior electrodes arranged alongside one another on said elongate body member such that said second end of said first anterior electrode is adjacent said first end of said second anterior electrode with a first distance therebetween, said first distance being in the range of 1 mm to 15 mm, and
a cumulative length consists of the sum of said length of said first electrode, said length of said second electrode, and said first distance, said cumulative length being in the range of 20 mm to 55 mm,
wherein said first anterior electrode is configured, when said headset is donned, to be disposed above the supratrochlear nerve on one side of the user's head, and said second anterior electrode is configured, when said headset is donned, to be disposed above the supraorbital nerve on said one side of the user's head.

11. The headset of claim 1, further comprising at least one compressible portion mounted onto an inner surface of said body member and configured to engage the skin of said user, said compressible portion extending radially toward the center of said headset,
wherein said at least one compressible portion is configured, when said headset is donned by said user, to be urged against skin of said user and to compress against the skin, such that said compressible portion extends radially toward the center of said headset to a greater degree when said headset is not donned by said user, than when said headset is donned by said user.

12. The headset of claim 11, wherein said at least one compressible portion comprises a compressible portion mounted onto a flexible leaf connected to said anterior section, said flexible leaf having a rest state and an extended state, and wherein, in said extended state, a curvature of said flexible leaf corresponds to a curvature of the scalp of a user donning said headset.

13. The headset of claim 12, wherein said at least one compressible portion further includes at least one anterior electrode and an electrode housing surrounding said at least one anterior electrode, said electrode housing including at least one hollow chamber adapted for trapping liquid emitted from said at least one anterior electrode when said at least one compressible portion and said at least one anterior electrode are compressed.

14. The headset of claim 1, further having at least one of the following structural features:
  at least one of said posterior electrodes is configured, when said headset is donned, to be disposed above at least one occipital nerve branch of said user, and
  at least one of said posterior electrodes comprises a transcranial stimulation electrode configured, when said headset is donned, to be disposed above an occipital brain region of said user.

15. The headset of claim 14, wherein each of said posterior sections includes a posterior section housing having at least one flexible surface and having said posterior electrode housed therein.

16. The headset of claim 15, wherein said at least one flexible surface is configured such that, when said headset is donned by a user and said posterior electrodes engage the scalp of said user, pressure applied to said at least one flexible surface causes deformation of said at least one flexible surface resulting in a conductive fluid being emitted from at least one of said posterior electrodes toward the scalp of the user, thereby to reduce the impedance between said at least one said posterior electrode and the scalp of the user.

17. The headset of claim 1, further comprising at least one side electrode mounted on an inner surface of said body member, the headset having at least one of the following structural features:
  said at least one side electrode is configured to be disposed, when said headset is donned, above at least one of the zygomaticotemporal nerve and the auriculotemporal nerve of said user; and
  said at least one side electrode comprises a transcranial stimulation electrode configured to be disposed, when said headset is donned, above the temple of said user and anterior to the ear of said user or immediately behind the ear of said user.

18. The headset of claim 1, further comprising a spatial orientation sensor configured to sense an angular position of said headset, when donned.

19. The headset of claim 1, wherein in said closed state, said posterior ends of said arm sections engage one another only along short lateral end edges of said elongate body member.

20. The headset of claim 1, wherein, in said rest state, a curvature of each of said arm sections, adjacent a corresponding one of said posterior ends, is defined by a partially circumscribed imaginary circle having a first radius, and
  wherein, in a donning state of said headset during donning thereof on the head of the user, force applied to each side of the user's head by said closure mechanism affects said curvature of each of said arm sections adjacent said corresponding one of said posterior ends, such that during said donning state said curvature of each of said arm sections is defined by a partially circumscribed imaginary circle having a second radius, said second radius being greater than said first radius.

21. A method of donning a headset on the head of a user, the method comprising:
  providing a headset according to claim 1, said headset being in said rest state;
  positioning said headset adjacent the head of said user, such that said posterior ends of said arm members engage sides of the head of said user, while said body member is in an open state; and
  pushing said headset rearward, until said closure mechanism closes said body member into said closed state, such that the headset fully encircles the head of said user while said anterior section engages the forehead of the user.

22. The method of claim 21, wherein said pushing further includes, during motion of said headset rearward, said posterior ends of said arm sections plowing through said hair and clearing an area of said scalp of said user for physical contact of said posterior electrodes therewith.

23. The method of claim 21, further comprising, when said body member is in said closed state, adjusting a size of said body member by simultaneously pushing against said anterior section and said posterior sections of said body member, so as to adjust the length of said at least one size-adjustment mechanism.

24. The method of claim 21, further comprising, subsequent to said pushing said headset rearward, applying pressure to a flexible surface adjacent said posterior electrodes and compressing said posterior electrodes to release a conductive fluid from said posterior electrodes to an area between said posterior electrodes and said scalp of said user, thereby to reduce the impedance between said posterior electrodes and said scalp.

* * * * *